(12) United States Patent
Alon et al.

(10) Patent No.: US 10,952,848 B2
(45) Date of Patent: Mar. 23, 2021

(54) METHODS OF LOADING A PROSTHETIC VALVE IN A DELIVERY APPARATUS

(71) Applicant: Edwards Lifesciences Corporation, Irvine, CA (US)

(72) Inventors: David Alon, Zichron Yaacov (IL); Netanel Benichou, D.N. Hof HaCarmel (IL); Oded Meiri, Moshav Ram-On (IL)

(73) Assignee: Edwards Lifesciences Corporation, Irvine, CA (US)

( * ) Notice: Subject to any disclaimer, the term of this patent is extended or adjusted under 35 U.S.C. 154(b) by 219 days.

(21) Appl. No.: 15/953,991

(22) Filed: Apr. 16, 2018

(65) Prior Publication Data
US 2018/0228606 A1 Aug. 16, 2018

Related U.S. Application Data

(63) Continuation of application No. 15/181,243, filed on Jun. 13, 2016, now Pat. No. 10,238,487, which is a
(Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/2439* (2013.01);
(Continued)

(58) Field of Classification Search
CPC ...... A61F 2/2427; A61F 2/243; A61F 2/2436; A61F 2/2439; A61F 2/2466; A61F 2/95;
(Continued)

(56) References Cited

U.S. PATENT DOCUMENTS 3,409,013 A 11/1968 Berry
3,548,417 A 12/1970 Kisher
(Continued)

FOREIGN PATENT DOCUMENTS

CA 2767527 A1 1/2011
DE 2246526 A1 3/1973
(Continued)

OTHER PUBLICATIONS

Chinese Office Action, 2009-80142271 dated Jun. 2013.
(Continued)

*Primary Examiner* — Thomas McEvoy
(74) *Attorney, Agent, or Firm* — Edwards Lifesciences; Hans P. Smith

(57) ABSTRACT

Embodiments of the present disclosure provide methods of loading a prosthetic heart valve within a delivery apparatus such that it can be used for delivery of the prosthetic heart valve to a native valve site via the human vasculature. The methods can include attaching the prosthetic heart valve to a valve-retaining mechanism at a distal end of the catheter and causing a torque shaft of the delivery apparatus to rotate relative to the catheter, wherein the torque shaft extends within the catheter and is coupled to the valve delivery sheath. Rotation of the torque shaft relative to the catheter can cause relative longitudinal movement between the valve sheath and the prosthetic heart valve such that the prosthetic heart valve is covered by the valve sheath.

16 Claims, 37 Drawing Sheets

Related U.S. Application Data continuation of application No. 14/182,169, filed on Feb. 17, 2014, now Pat. No. 9,364,325, which is a continuation of application No. 12/429,040, filed on Apr. 23, 2009, now Pat. No. 8,652,202.

(60) Provisional application No. 61/091,293, filed on Aug. 22, 2008.

(52) U.S. Cl.
CPC ........... *A61F 2/9517* (2020.05); *A61F 2/9522* (2020.05); *A61F 2002/9528* (2013.01); *A61F 2002/9534* (2013.01); *A61F 2210/0076* (2013.01); *A61F 2220/005* (2013.01); *A61F 2220/0075* (2013.01); *A61F 2230/001* (2013.01); *A61F 2230/0054* (2013.01); *A61F 2230/0076* (2013.01); *A61F 2250/0039* (2013.01)

(58) Field of Classification Search
CPC .. A61F 2/962; A61F 2/966; A61F 2002/9505; A61F 2002/9534; A61F 2002/9665
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,901 A | 11/1988 | Baykut |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,906 A | 11/1989 | Lindemann et al. |
| 4,883,458 A | 11/1989 | Shiber |
| 4,922,905 A | 5/1990 | Strecker |
| 4,979,939 A | 12/1990 | Shiber |
| 4,986,830 A | 1/1991 | Owens et al. |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,201,757 A | 4/1993 | Heyn et al. |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,397,351 A | 3/1995 | Pavcnik et al. |
| 5,411,055 A | 5/1995 | Kane |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,549,665 A | 8/1996 | Vesely et al. |
| 5,571,175 A | 11/1996 | Vanney et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,800,508 A | 9/1998 | Goicoechea et al. |
| 5,843,162 A | 12/1998 | Inoue |
| 5,855,601 A | 1/1999 | Bessler et al. |
| 5,855,602 A | 1/1999 | Angell |
| 5,957,949 A | 9/1999 | Leonhardt et al. |
| 6,027,525 A | 2/2000 | Suh et al. |
| 6,132,458 A * | 10/2000 | Staehle ............... A61F 2/95 623/1.11 |
| 6,132,473 A | 10/2000 | Williams et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,231,602 B1 | 5/2001 | Carpentier et al. |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,352,547 B1 | 3/2002 | Brown et al. |
| 6,440,764 B1 | 8/2002 | Focht et al. |
| 6,468,660 B2 | 10/2002 | Ogle et al. |
| 6,488,704 B1 | 12/2002 | Connelly et al. |
| 6,569,196 B1 | 5/2003 | Vesely |
| 6,605,112 B1 | 8/2003 | Moll et al. |
| 6,689,123 B2 | 2/2004 | Pinchasik |
| 6,716,244 B2 | 4/2004 | Klaco |
| 6,769,161 B2 | 8/2004 | Brown |
| 6,783,542 B2 | 8/2004 | Eidenschink |
| 6,878,162 B2 | 4/2005 | Bales et al. |
| 6,911,039 B2 | 6/2005 | Shiu et al. |
| 6,936,067 B2 | 8/2005 | Buchanan |
| 7,096,554 B2 | 8/2006 | Austin et al. |
| 7,225,518 B2 | 6/2007 | Eidenschink et al. |
| 7,563,280 B2 | 7/2009 | Anderson et al. |
| 7,618,447 B2 | 11/2009 | Case et al. |
| 7,655,034 B2 | 2/2010 | Mitchell et al. |
| 7,749,266 B2 | 7/2010 | Forster et al. |
| 7,993,394 B2 | 8/2011 | Hariton et al. |
| 8,291,570 B2 | 10/2012 | Eidenschink et al. |
| 8,454,685 B2 | 6/2013 | Hariton et al. |
| 8,652,145 B2 | 2/2014 | Maimon et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 9,155,619 B2 | 10/2015 | Liu et al. |
| 9,168,131 B2 | 10/2015 | Yohanan et al. |
| 9,867,700 B2 | 1/2018 | Bakis et al. |
| 2001/0021872 A1 | 9/2001 | Bailey et al. |
| 2001/0034549 A1* | 10/2001 | Bartholf ................ A61F 2/95 623/1.12 |
| 2002/0026094 A1 | 2/2002 | Roth |
| 2002/0032481 A1 | 3/2002 | Gabbay |

(56) References Cited

U.S. PATENT DOCUMENTS

| | | |
|---|---|---|
| 2002/0173842 A1 | 11/2002 | Buchanan |
| 2003/0040792 A1 | 2/2003 | Gabbay |
| 2003/0074628 A1 | 4/2003 | Lee |
| 2003/0158597 A1 | 8/2003 | Quiachon et al. |
| 2004/0039436 A1 | 2/2004 | Spenser et al. |
| 2004/0210304 A1 | 10/2004 | Seguin et al. |
| 2004/0236411 A1 | 11/2004 | Sarac et al. |
| 2005/0075728 A1 | 4/2005 | Nguyen et al. |
| 2005/0075731 A1 | 4/2005 | Artof et al. |
| 2005/0113910 A1 | 5/2005 | Paniagua et al. |
| 2005/0137688 A1 | 6/2005 | Salahieh et al. |
| 2005/0137693 A1 | 6/2005 | Haug et al. |
| 2005/0137697 A1 | 6/2005 | Salahieh et al. |
| 2005/0143809 A1 | 6/2005 | Salahieh et al. |
| 2005/0149159 A1 | 7/2005 | Andreas et al. |
| 2005/0149160 A1 | 7/2005 | McFerran |
| 2005/0154252 A1 | 7/2005 | Sharkey et al. |
| 2005/0188525 A1 | 9/2005 | Weber |
| 2005/0203614 A1 | 9/2005 | Forster et al. |
| 2006/0004469 A1 | 1/2006 | Sokel |
| 2006/0030881 A1 | 2/2006 | Sharkey et al. |
| 2006/0142837 A1 | 6/2006 | Haverkost et al. |
| 2006/0149360 A1 | 7/2006 | Schwammenthal et al. |
| 2006/0155358 A1 | 7/2006 | LaDuca et al. |
| 2006/0178740 A1 | 8/2006 | Stacchino et al. |
| 2006/0183383 A1 | 8/2006 | Asmus et al. |
| 2006/0229491 A1 | 10/2006 | Sharkey et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0264980 A1 | 11/2006 | Khairkhahan et al. |
| 2006/0276813 A1 | 12/2006 | Greenberg |
| 2006/0281965 A1 | 12/2006 | Khairkhahan et al. |
| 2006/0282150 A1 | 12/2006 | Olson et al. |
| 2006/0287719 A1 | 12/2006 | Rowe et al. |
| 2007/0010876 A1 | 1/2007 | Salahieh et al. |
| 2007/0010877 A1 | 1/2007 | Salahieh et al. |
| 2007/0073389 A1 | 3/2007 | Bolduc et al. |
| 2007/0088431 A1 | 4/2007 | Bourang et al. |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2008/0071361 A1 | 3/2008 | Tuval et al. |
| 2008/0097397 A1 | 4/2008 | Vrba |
| 2008/0125853 A1 | 5/2008 | Bailey et al. |
| 2008/0147182 A1 | 6/2008 | Righini et al. |
| 2008/0154355 A1 | 6/2008 | Benichou et al. |
| 2008/0161902 A1 | 7/2008 | Poulsen |
| 2008/0161911 A1 | 7/2008 | Revuelta et al. |
| 2008/0183271 A1 | 7/2008 | Frawley et al. |
| 2008/0255651 A1* | 10/2008 | Dwork ............... A61F 2/95 623/1.11 |
| 2008/0275537 A1 | 11/2008 | Limon |
| 2008/0319526 A1 | 12/2008 | Hill et al. |
| 2009/0099638 A1 | 4/2009 | Grewe |
| 2009/0125118 A1 | 5/2009 | Gong |
| 2009/0276039 A1 | 11/2009 | Meretei |
| 2009/0299452 A1 | 12/2009 | Eidenschink et al. |
| 2010/0049313 A1 | 2/2010 | Alon et al. |
| 2010/0168844 A1 | 7/2010 | Toomes et al. |
| 2010/0191326 A1 | 7/2010 | Alkhatib |
| 2010/0204781 A1 | 8/2010 | Alkhatib |
| 2011/0040374 A1 | 2/2011 | Goetz et al. |
| 2011/0319991 A1 | 12/2011 | Hariton et al. |
| 2012/0071969 A1 | 3/2012 | Li et al. |
| 2012/0259409 A1 | 10/2012 | Nguyen et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0157455 A1 | 6/2015 | Hoang et al. |
| 2017/0056149 A1 | 3/2017 | Rajpara et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |

FOREIGN PATENT DOCUMENTS

| | | |
|---|---|---|
| DE | 0144167 C | 6/1985 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| EP | 1806114 A2 | 7/2007 |
| EP | 2218403 A1 | 8/2010 |
| EP | 2247263 B1 | 8/2011 |
| EP | 2363099 A2 | 9/2011 |
| EP | 3398560 A1 | 11/2018 |
| FR | 2788217 A1 | 7/2000 |
| FR | 2815844 A1 | 5/2002 |
| GB | 2056023 A | 3/1981 |
| JP | 2007516055 A | 6/2007 |
| JP | 2007181702 A | 7/2007 |
| SU | 1271508 A1 | 11/1986 |
| WO | 91/17720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 05/034812 | 4/2005 |
| WO | 2005084595 A1 | 9/2005 |
| WO | 2006014233 A2 | 2/2006 |
| WO | 2006034008 A2 | 3/2006 |
| WO | 2006111391 A1 | 10/2006 |

(56) References Cited

FOREIGN PATENT DOCUMENTS

| | | |
|---|---|---|
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007054015 A1 | 5/2007 |
| WO | 2007067942 A1 | 6/2007 |
| WO | 2007097983 A2 | 8/2007 |
| WO | 2007112029 A2 | 10/2007 |
| WO | 2008005405 A2 | 1/2008 |
| WO | 2008015257 A2 | 2/2008 |
| WO | 2008028569 A1 | 3/2008 |
| WO | 2008035337 A2 | 3/2008 |
| WO | 2008091515 A2 | 7/2008 |
| WO | 2008124844 A1 | 10/2008 |
| WO | 2008147964 A1 | 12/2008 |
| WO | 2008150529 A1 | 12/2008 |
| WO | 2009033469 A1 | 3/2009 |
| WO | 2010121076 A2 | 10/2010 |

OTHER PUBLICATIONS

Chinese Search Report, 2009-80142271, dated Jun. 13, 2013.
Mexican Office Action, MX/a/2011/001841, dated Jun. 18, 2013.
Mexican Office Action, dated Jun. 18, 2013.
EPO Office Action_EP09808759_dated Apr. 20, 2017.
EPO Office Action_EP09808759_dated Dec. 13, 2017.
EP Search Report_EP09808759_dated Dec. 19, 2013.
ISR_PCTUS2009054290_Mar. 19, 2010.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications;" European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

\* cited by examiner

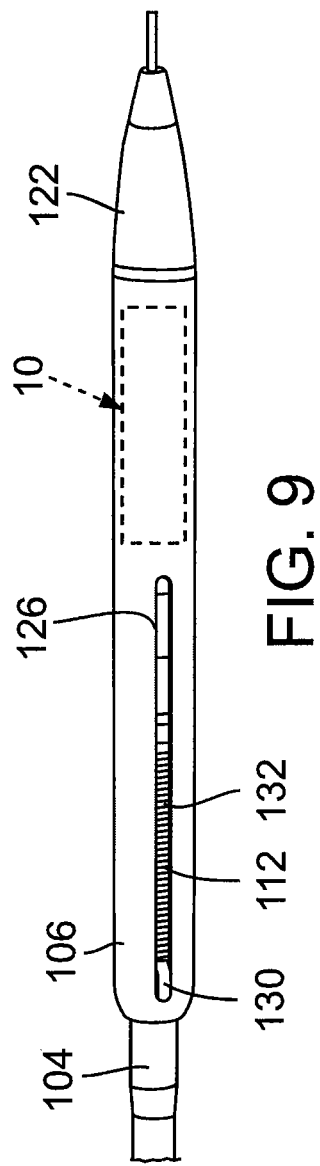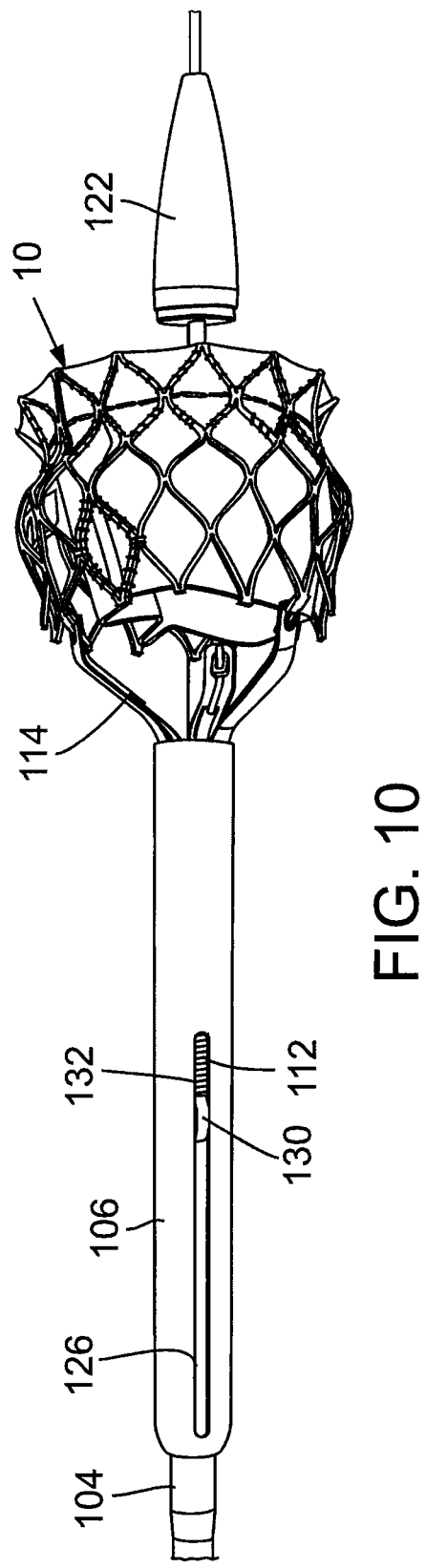
FIG. 9
FIG. 10

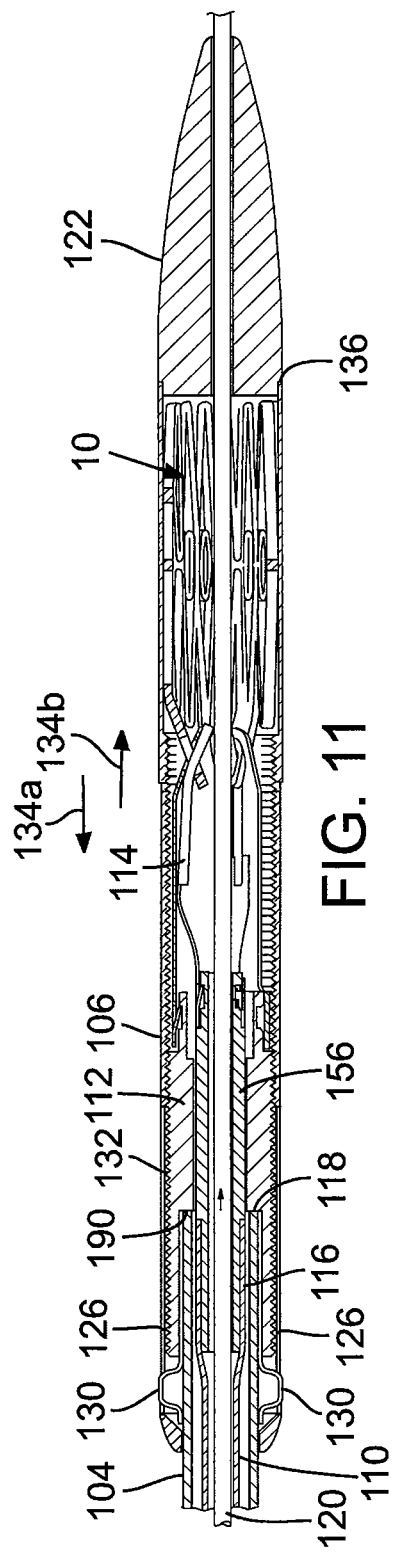
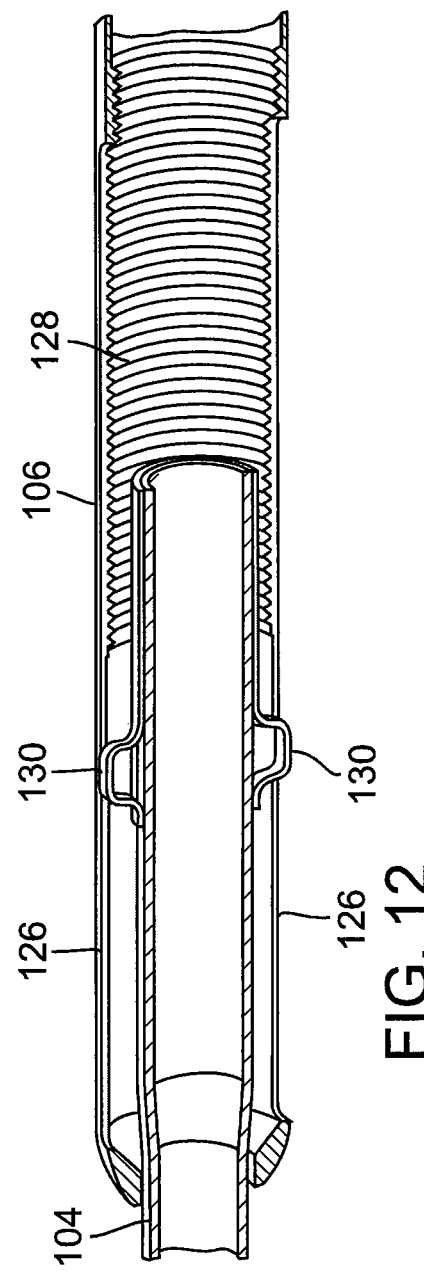

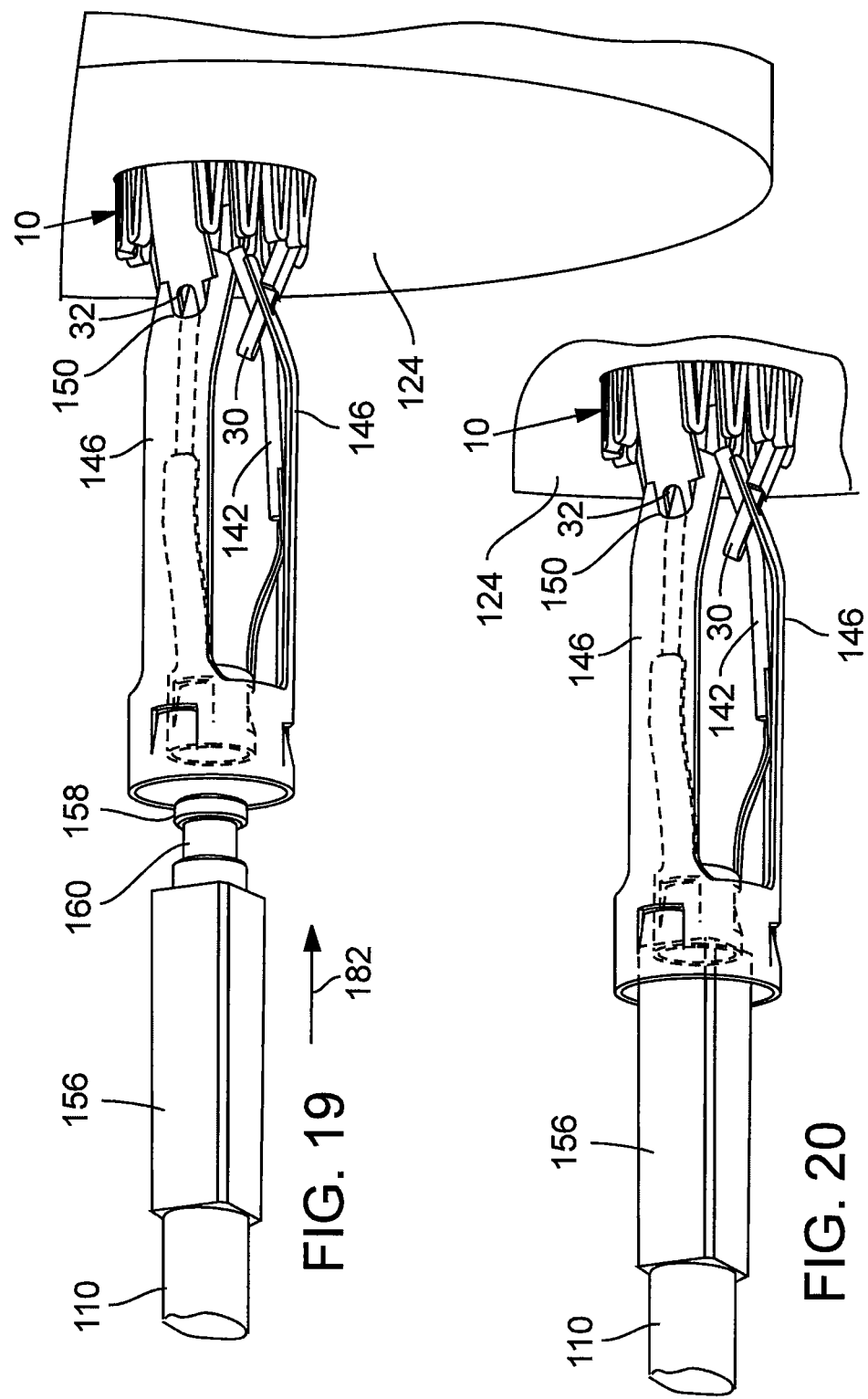

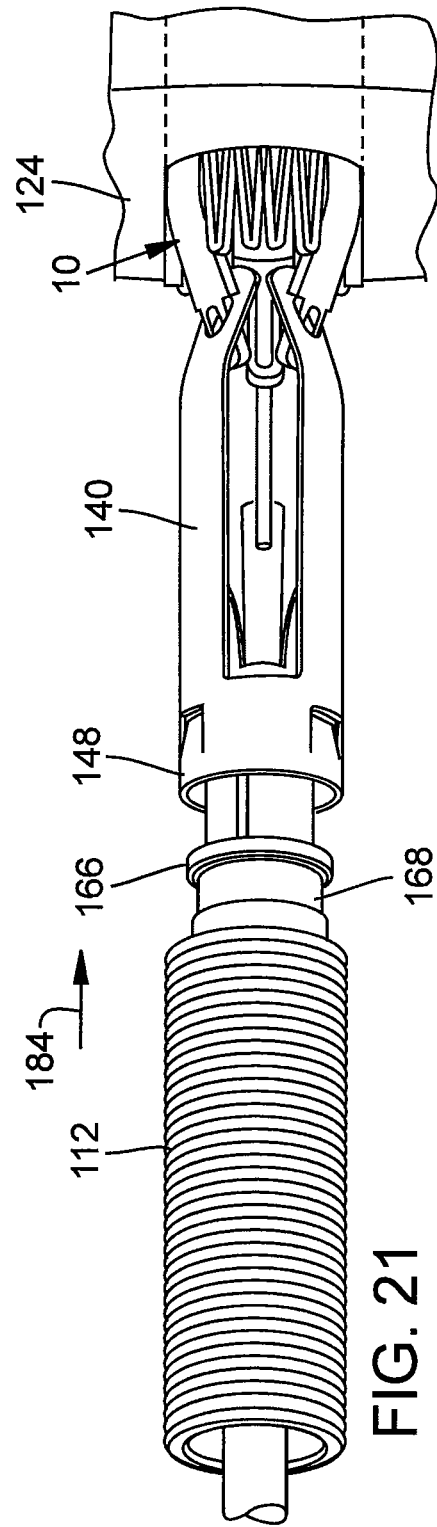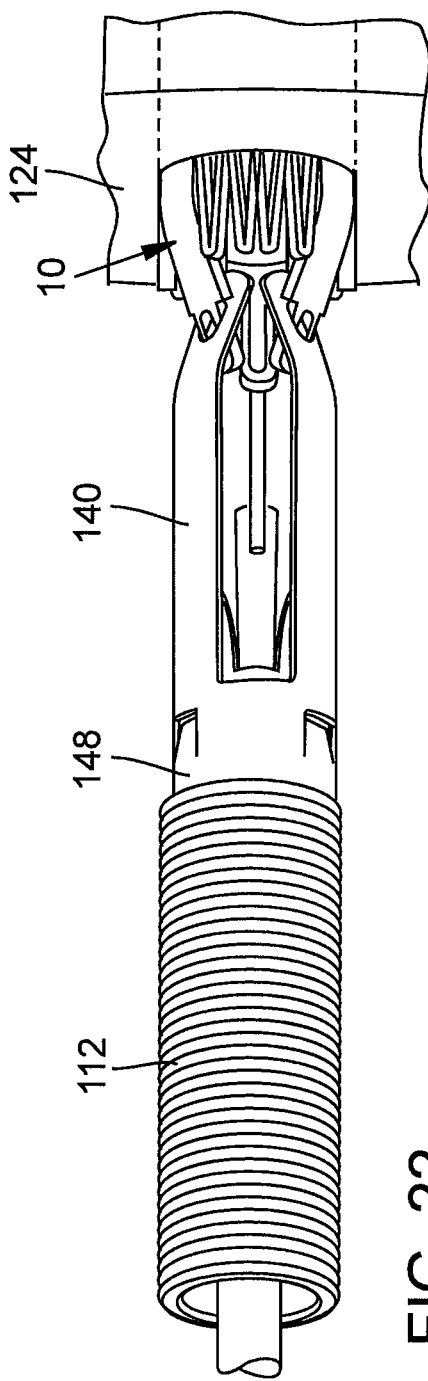

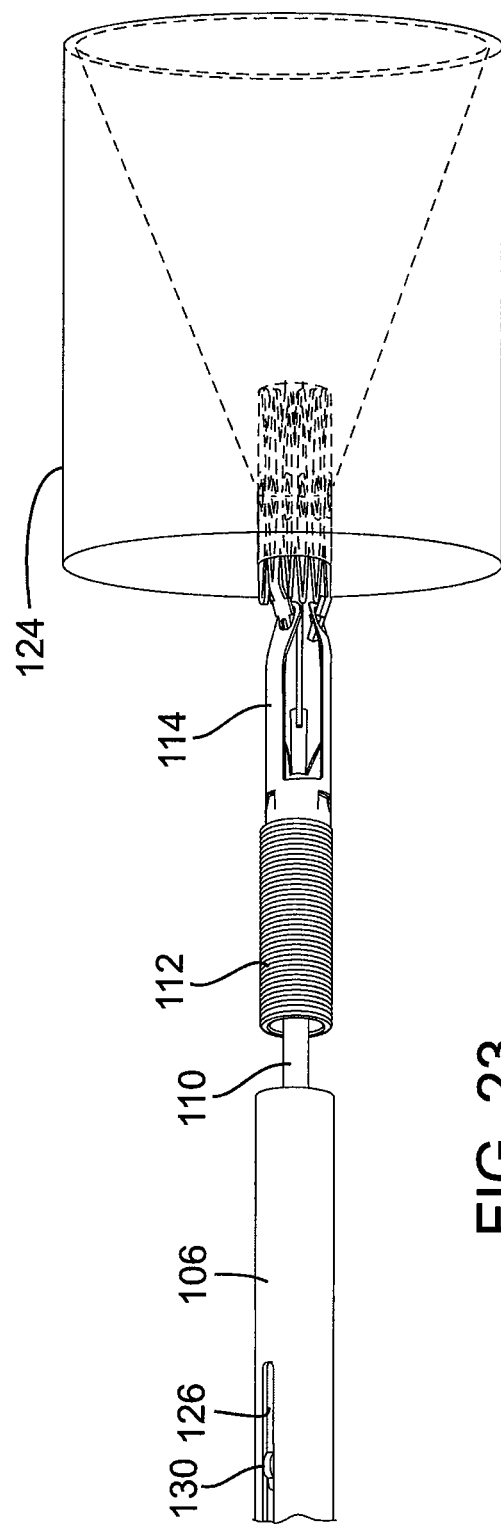

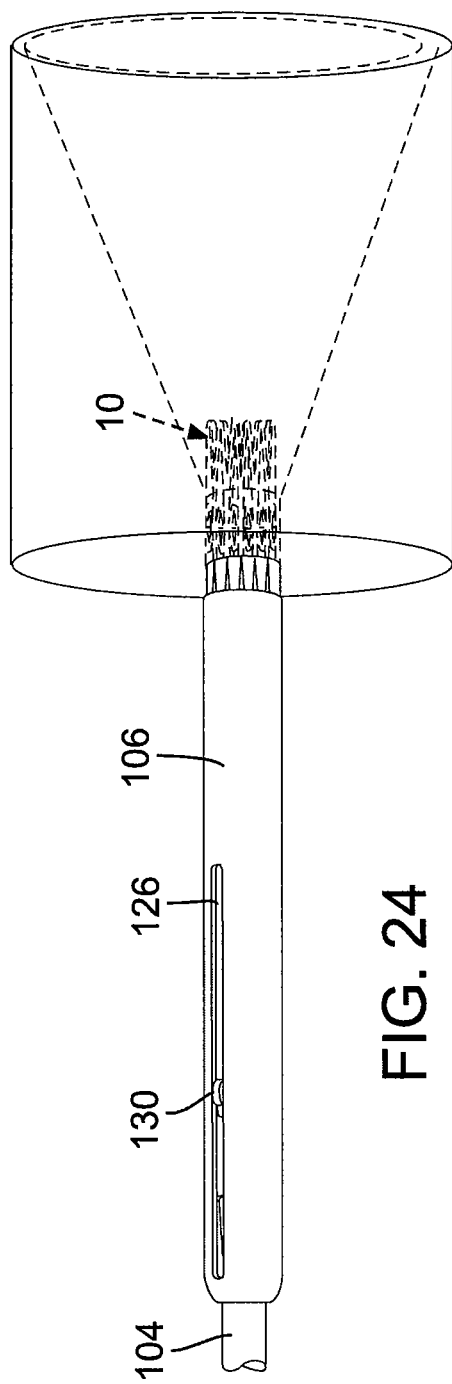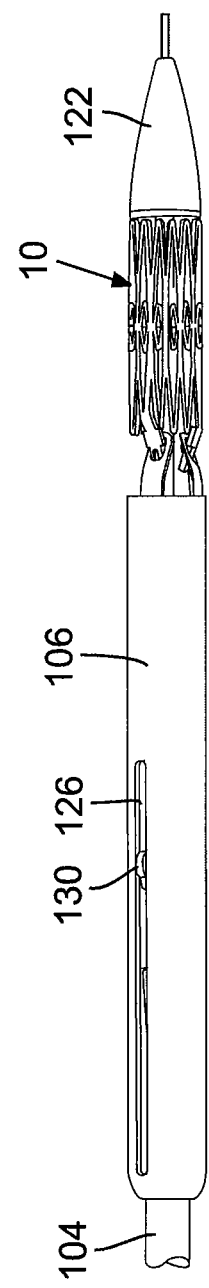
FIG. 24
FIG. 25

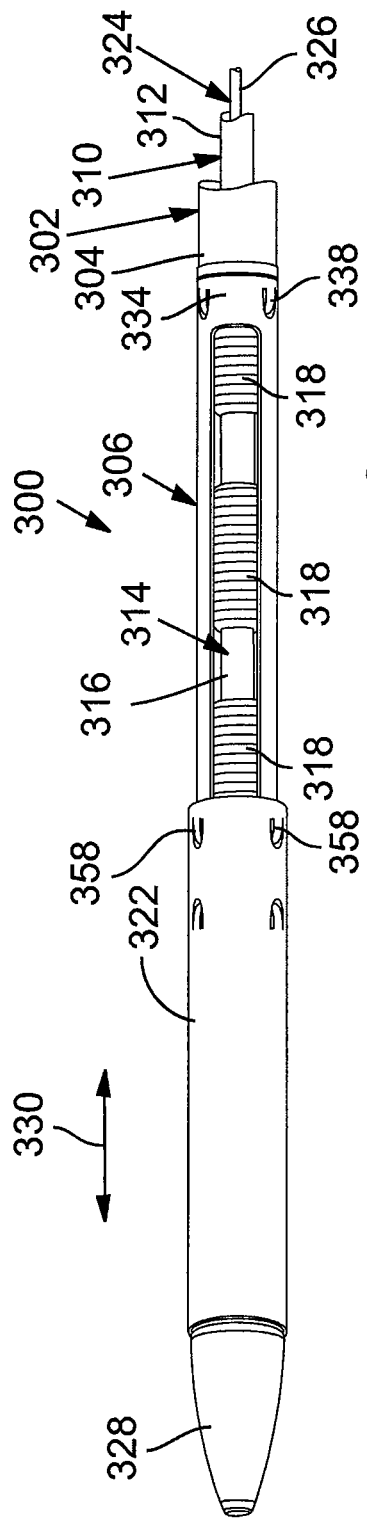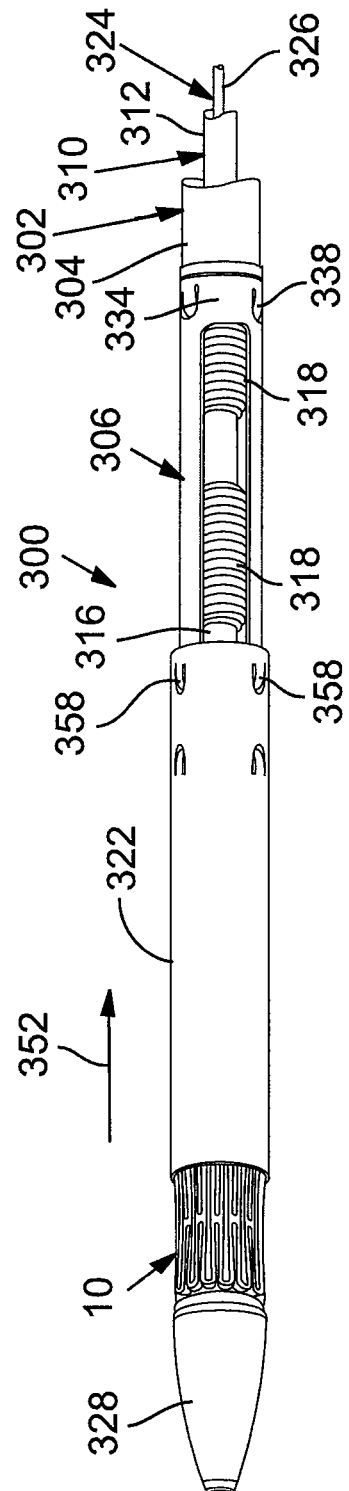

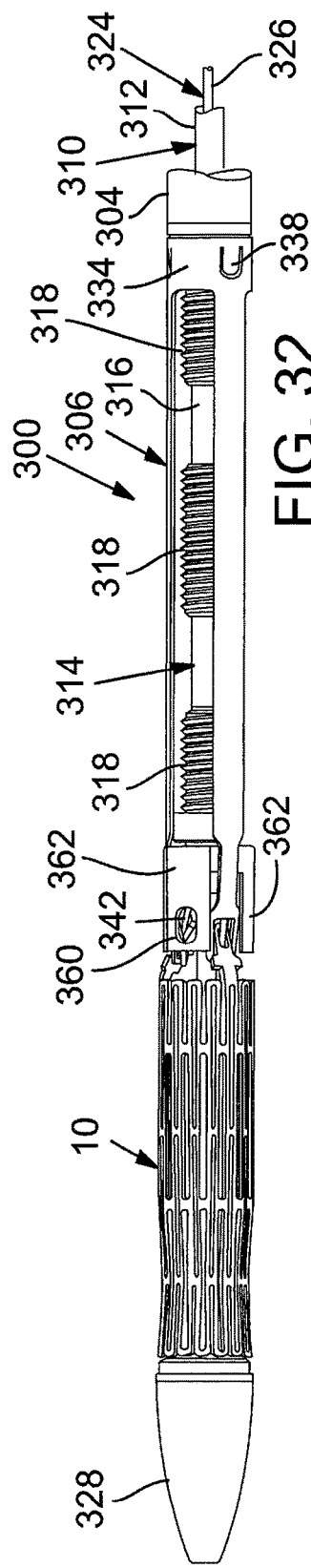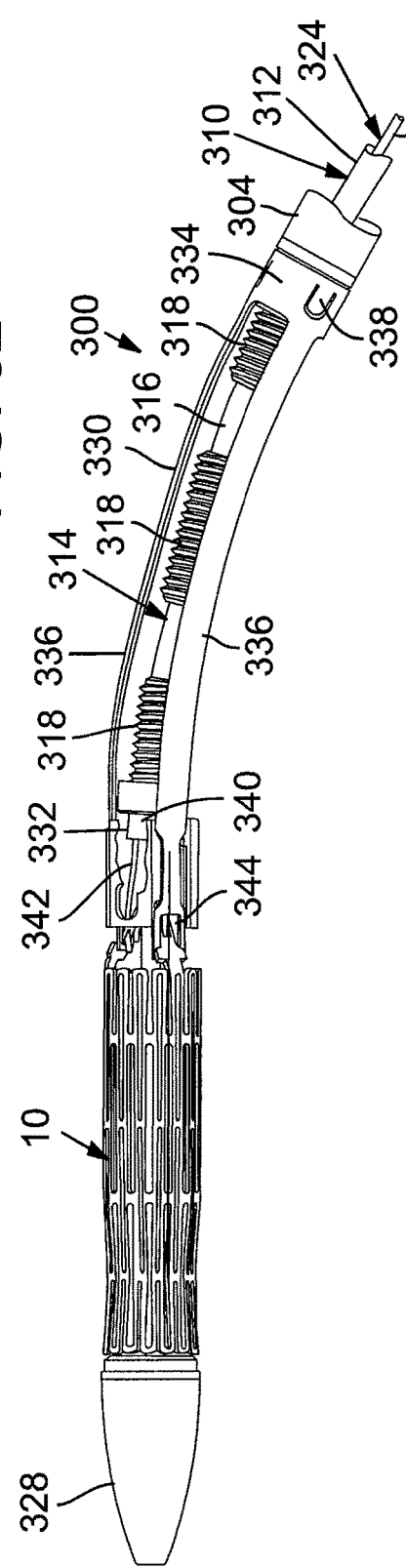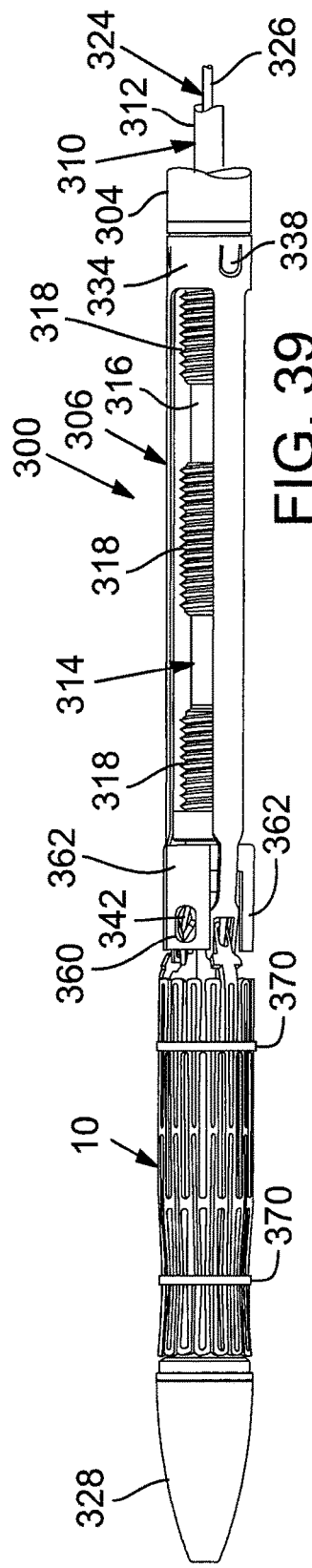

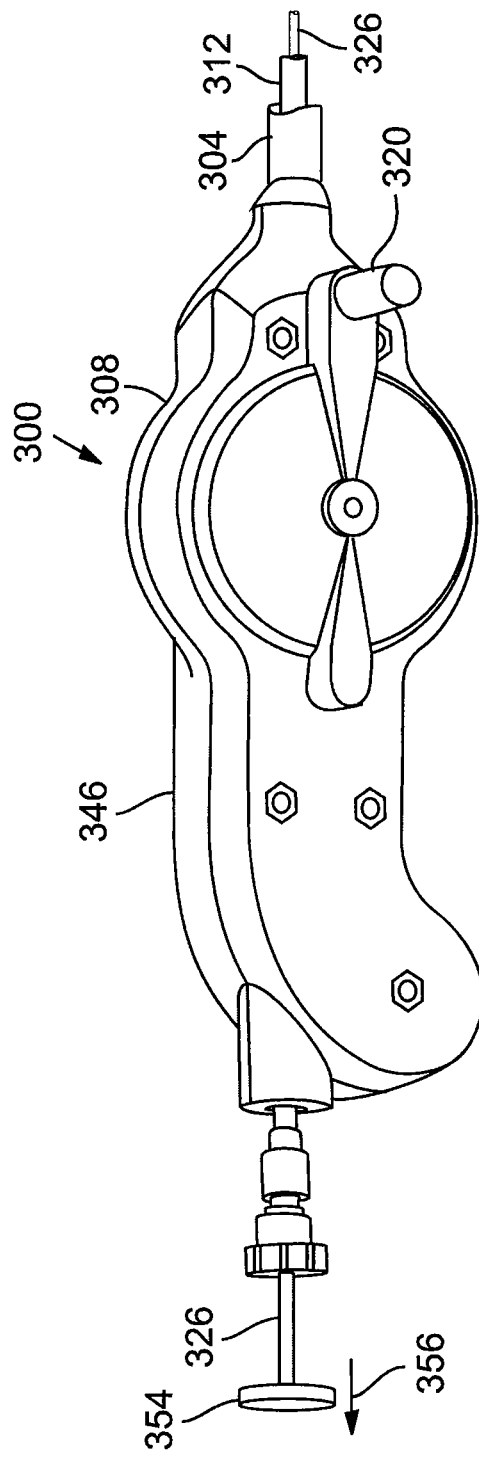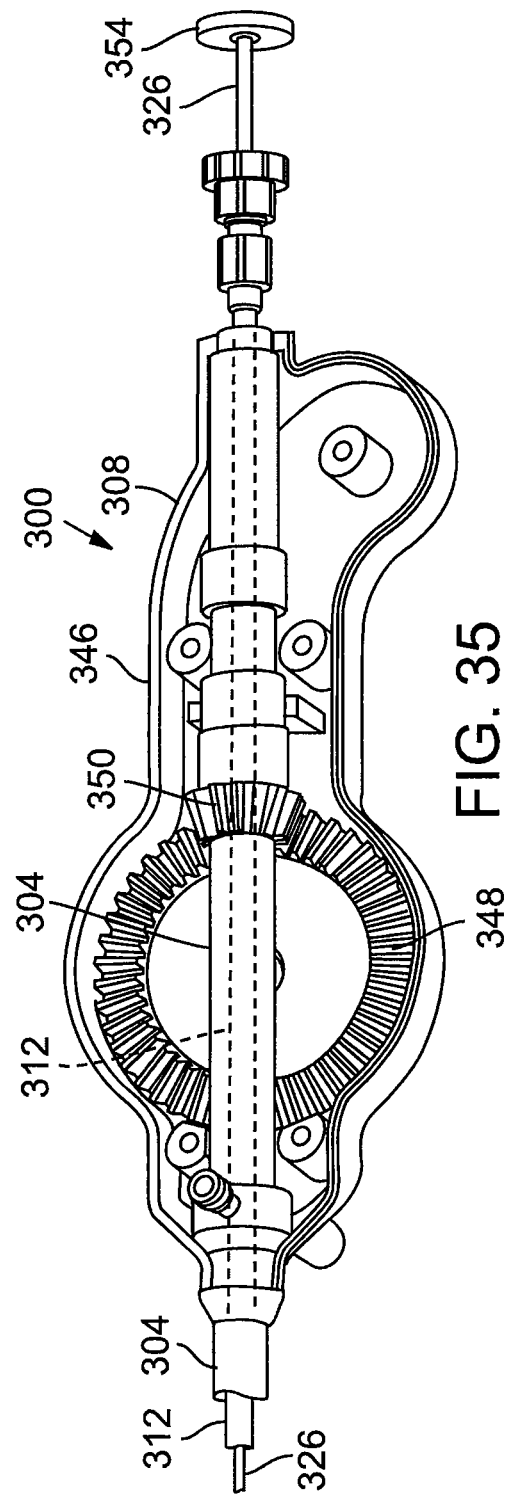

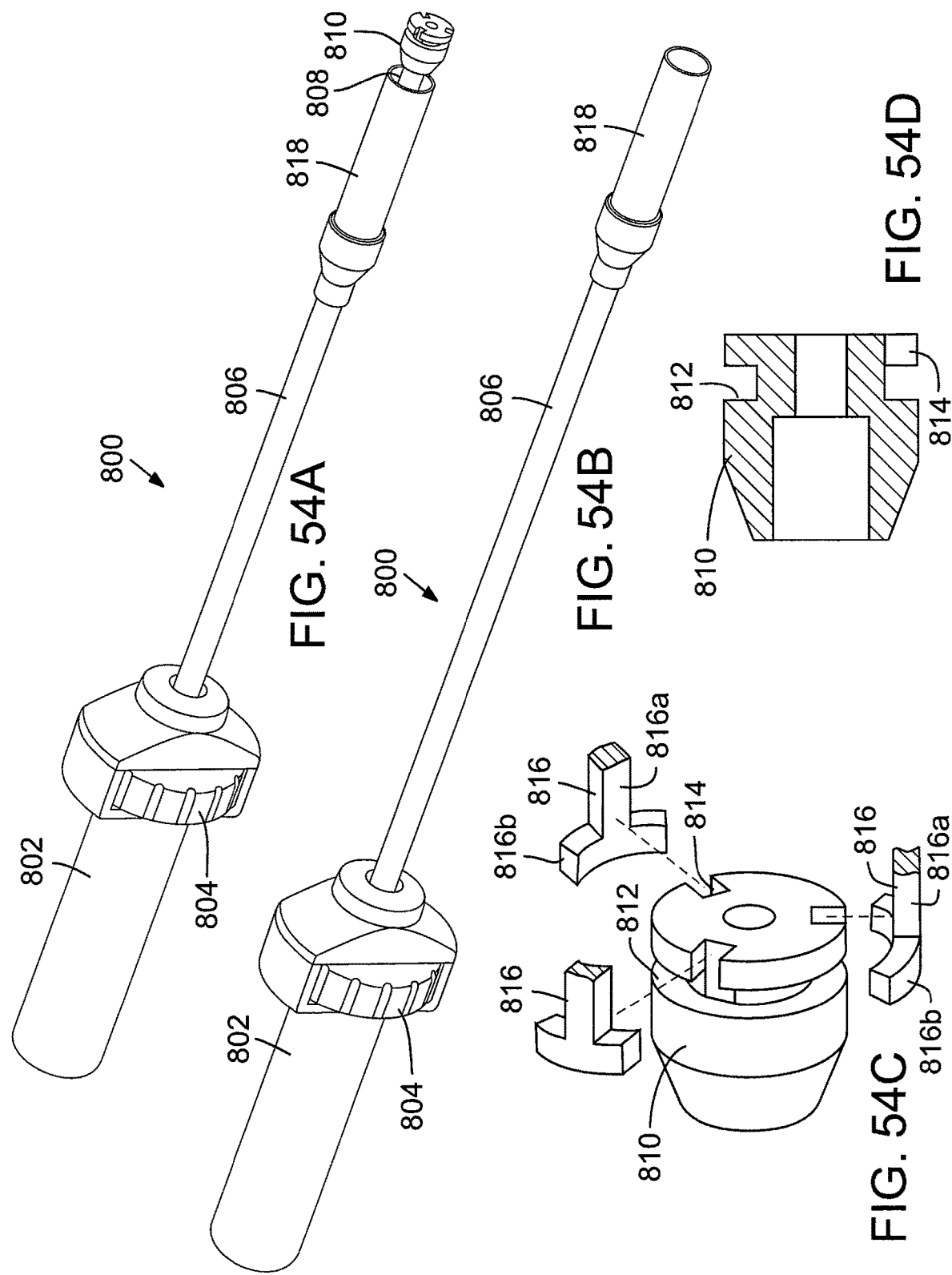

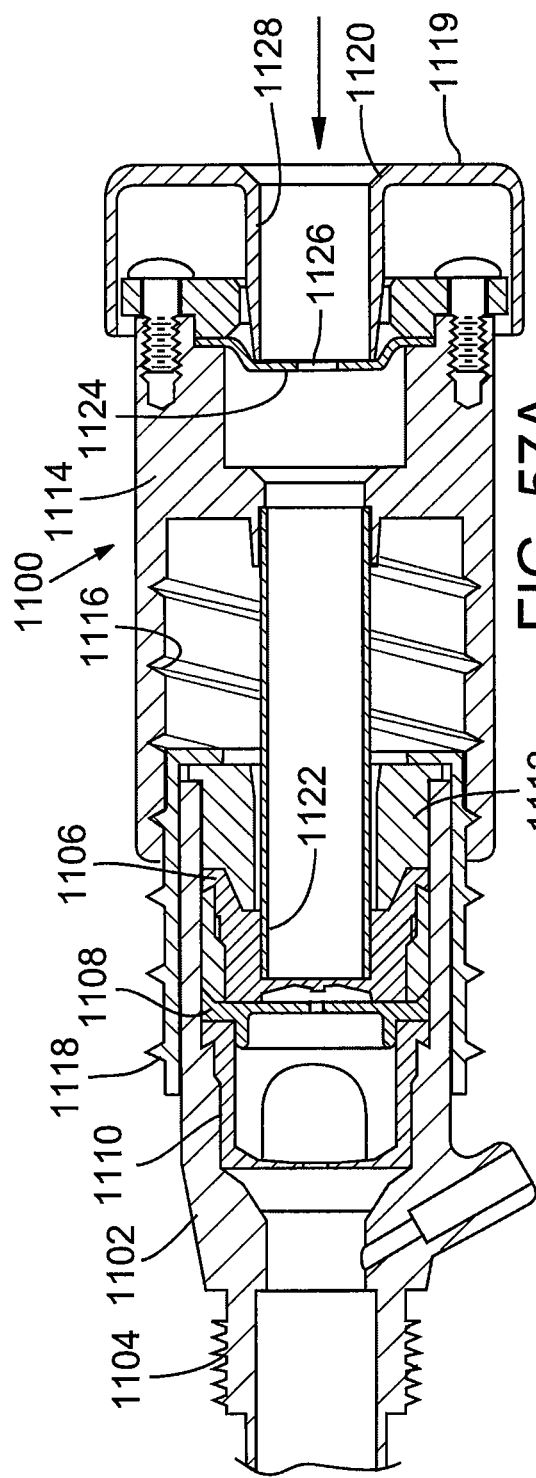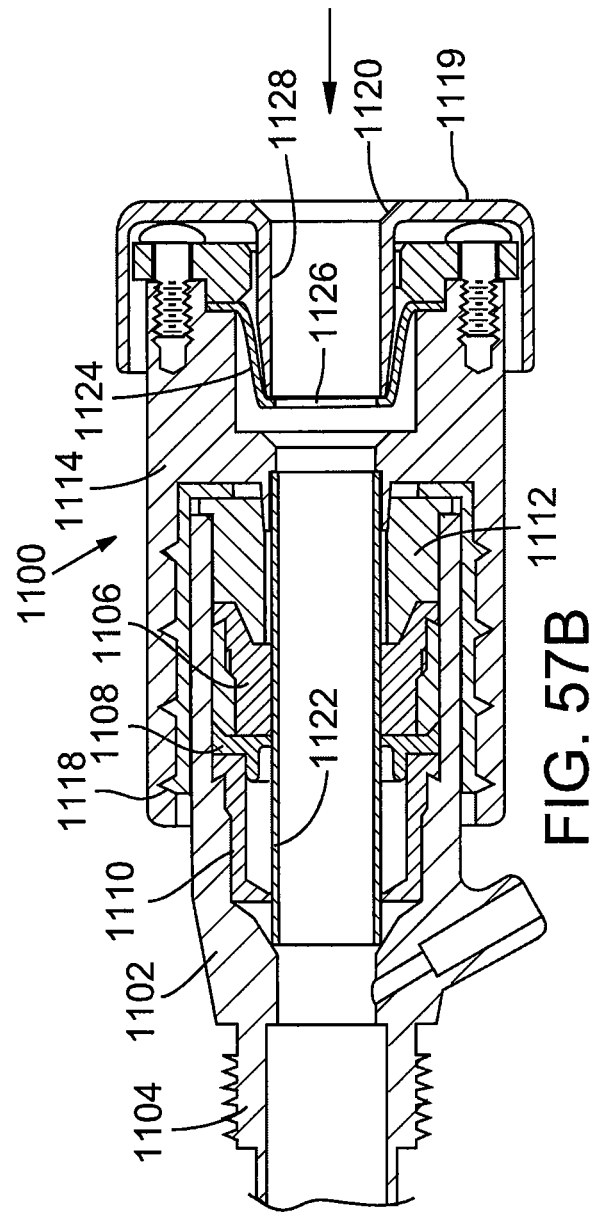

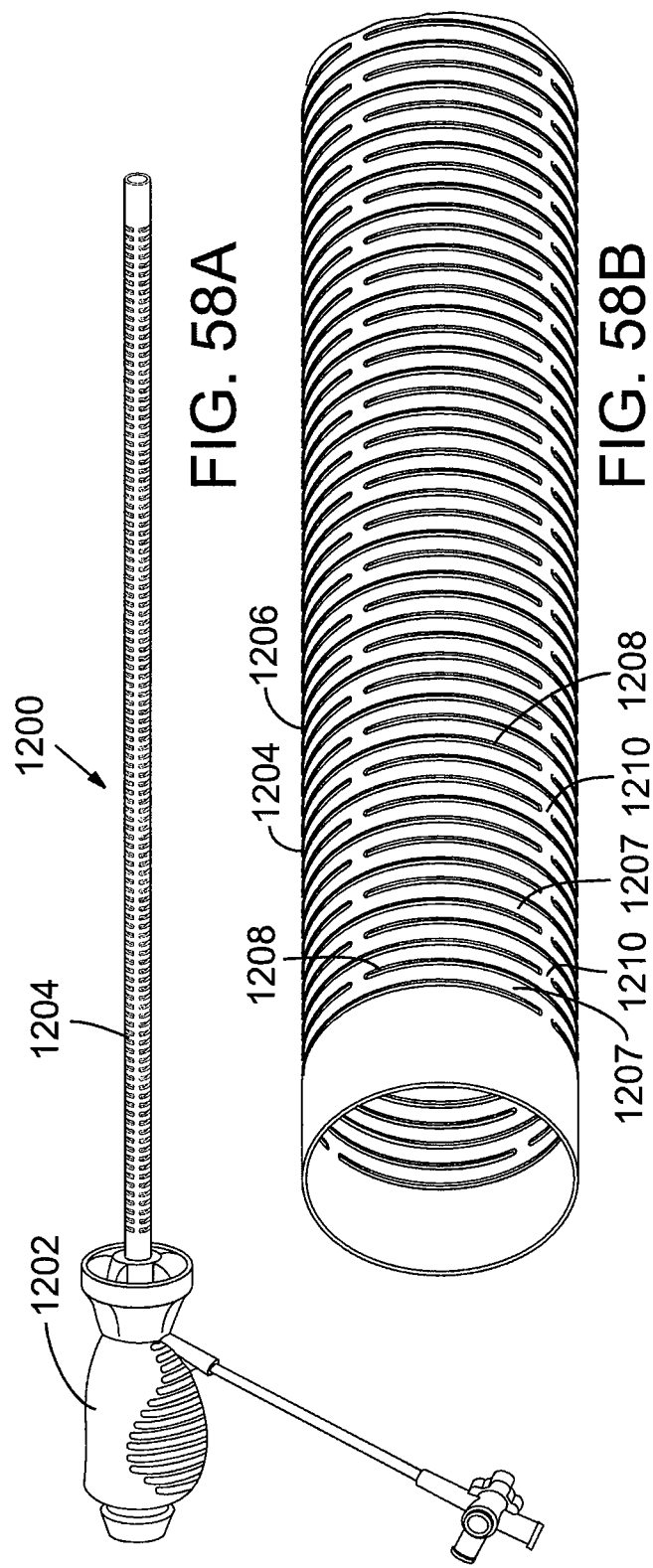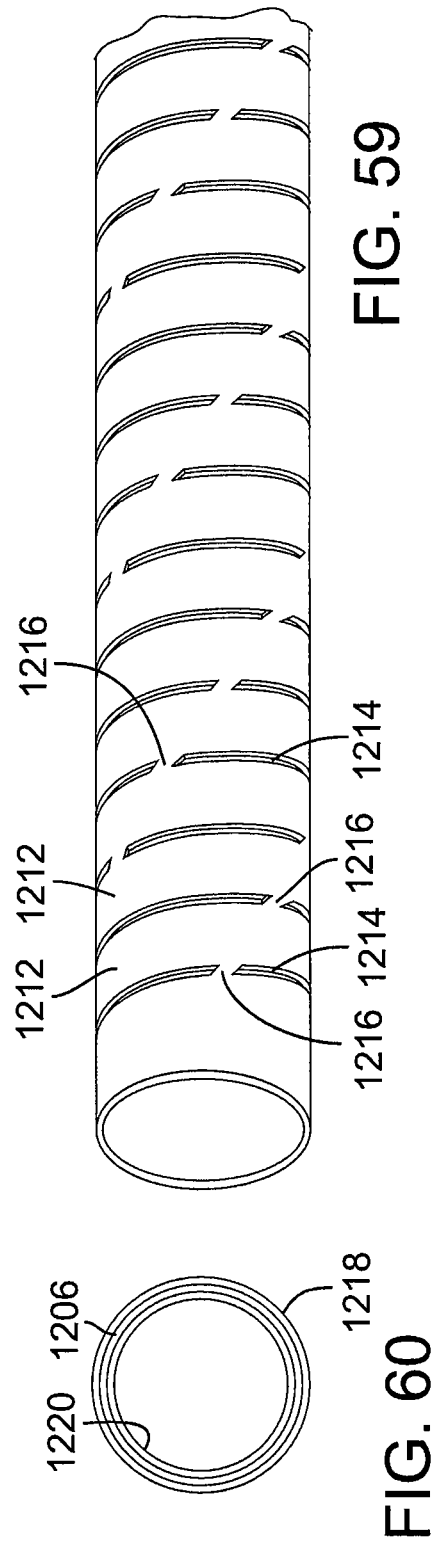

METHODS OF LOADING A PROSTHETIC VALVE IN A DELIVERY APPARATUS

CROSS-REFERENCE TO RELATED APPLICATIONS

This application is a continuation of U.S. patent application Ser. No. 15/181,243, filed Jun. 13, 2016, which is a continuation of U.S. patent application Ser. No. 14/182,169, filed Feb. 17, 2014, now U.S. Pat. No. 9,364,325, which is a continuation of U.S. patent application Ser. No. 12/429,040, filed Apr. 23, 2009, now U.S. Pat. No. 8,652,202, which claims the benefit of U.S. Application No. 61/091,293, filed Aug. 22, 2008, all of these applications are incorporated herein by reference.

FIELD

The present invention concerns embodiments of a prosthetic heart valve and a delivery apparatus for implanting a prosthetic heart valve.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted. Alternatively, the valve can have a resilient, self-expanding stent or frame that expands the valve to its functional size when it is advanced from a delivery sheath at the distal end of the catheter.

Balloon-expandable valves typically are preferred for replacing calcified native valves because the catheter balloon can apply sufficient expanding force to anchor the frame of the prosthetic valve to the surrounding calcified tissue. On the other hand, self-expanding valves typically are preferred for replacing a defective, non-stenotic (non-calcified) native valve. One drawback associated with implanting a self-expanding valve is that as the operator begins to advance the valve from the open end of the delivery sheath, the valve tends to "jump" out very quickly from the end of the sheath; in other words, the outward biasing force of the valve's frame tends to cause the valve to be ejected very quickly from the distal end of the delivery sheath, making it difficult to deliver the valve from the sheath in a precise and controlled manner and increasing the risk of trauma to the patient.

Another problem associated with implanting a percutaneous prosthetic valve in a non-stenotic native valve is that the prosthetic valve may not be able to exert sufficient force against the surrounding tissue to resist migration of the prosthetic valve. Typically, the stent of the prosthetic valve must be provided with additional anchoring or attachment devices to assist in anchoring the valve to the surrounding tissue. Moreover, such anchoring devices or portions of the stent that assist in anchoring the valve typically extend into and become fixed to non-diseased areas of the vasculature, which can result in complications if future intervention is required, for example, if the prosthetic valve needs to be removed from the patient.

SUMMARY

Certain embodiments of the present disclosure provide a prosthetic heart valve and a heart valve delivery apparatus for delivery of the prosthetic heart valve to a native valve site via the human vasculature. The delivery apparatus is particularly suited for advancing a prosthetic valve through the aorta (i.e., in a retrograde approach) for replacing a diseased native aortic valve.

In one embodiment of a prosthetic heart valve, the valve comprises a radially expandable and compressible support frame, or stent, and plural leaflets supported by the stent. The stent desirably comprises a plurality of strut members interconnected to each other to form a mesh structure having an inflow end and an outflow end. The mesh structure can have an overall curved shape that tapers inwardly from the inflow end to a reduced diameter section, increases in diameter from the reduced diameter section to a distended intermediate section, and then tapers from the intermediate section to toward the outflow end of the mesh structure. The valve can be implanted in a native aortic valve such that the reduced diameter section resides within the annulus of the native valve, the inflow end portion extends slightly below the valve annulus and the distended intermediate section extends slightly above the valve annulus into the Valsalva's sinuses. The flared inflow end portion and the distended intermediate section are greater in diameter than the native annulus and therefore assist in retaining the valve in place against forces tending to dislodge the valve in the upstream and downstream directions. Due to the geometry of the stent, the valve is particularly suited for replacing a non-stenotic valve, which typically does not anchor a prosthetic valve as well as a calcified native valve. The stent desirably does not include additional anchoring devices or frame portions to assist in anchoring the valve in place. Consequently, the valve can be implanted without contacting non-diseased areas of the vasculature, which prevents or at least minimizes complications if future intervention is required.

The plural leaflets of the valve have respective inflow end portions and outflow end portions. The inflow end portions of the leaflets can be secured to the inside of the mesh structure at the inflow end portion of the mesh structure. The outflow end portions of the leaflets define angularly spaced commisures that can be secured to the inside of the mesh structure at the outflow end of the mesh structure.

A delivery apparatus for delivering a self-expanding prosthetic valve can be configured to allow controlled and precise deployment of the valve from a valve sheath so as to minimize or prevent jumping of the valve from the valve sheath. In one embodiment, the valve is connected to the distal end of an elongated valve catheter and the sheath extends from a distal end of an outer catheter that extends over the valve catheter. To deploy the valve from the sheath, the valve catheter is rotated relative to the outer catheter and the sheath to effect sliding movement of the sheath relative to the valve until the valve is deployed from the distal end of the sheath. As the valve is advanced from the sheath, the valve catheter retains the valve against uncontrolled advancement or jumping of the valve from the sheath that can be caused by the natural resiliency of the valve. In another embodiment, the outer shaft can be connected to a screw shaft located in the handle of the delivery apparatus. The screw shaft can be operatively connected to an actuator knob that is rotated by the user to move the screw shaft and the outer shaft in the longitudinal directions. Longitudinal movement of the outer shaft in the proximal direction is effective to retract the sheath relative to the valve to deploy the valve from the sheath in a precise and controlled manner.

The delivery apparatus can include a retaining mechanism that forms a releasable connection between the valve and the distal end of the delivery apparatus. The retaining mechanism retains the valve relative to the delivery apparatus after the valve is deployed from the sheath to allow the user to adjust the position of the expanded valve relative to the target implantation site. In one embodiment, the retaining mechanism can include a first fork having a plurality of prongs formed with openings that receive respective posts of the valve's stent. A second fork has a plurality of prongs that extend through respective openings in the prongs of the first fork to form a releasable connection with each post of the stent. By virtue of this arrangement, the position of the expanded valve can be adjusted within the patient's body by manipulating the handle of the delivery apparatus. To release the valve, the second fork is retracted to withdraw its prongs from the openings in the stent, leaving the valve implanted in the body. In another embodiment, the retaining mechanism can comprise a plurality of sutures that extend from the distal end of the delivery apparatus. Each suture extends through an opening or hook portion of the stent and has a loop at its distal end through which a release wire extends. The release wire secures each suture to a portion of the stent. To release the valve, the release wire is retracted from the suture loops, allowing the sutures to release the valve from the distal end of the delivery apparatus.

In a representative embodiment, a heart-valve delivery apparatus for delivering a prosthetic heart valve via a patient's vasculature, comprises a catheter comprising a flexible torque shaft adapted to extend through the vasculature, the torque shaft having a distal end portion coupled to the prosthetic valve, and a valve sheath configured to receive the valve in a radially compressed state when coupled to the distal end portion of the catheter for delivery to the heart through the patient's vasculature. The apparatus is configured such that rotation of the torque shaft is effective to cause relative longitudinal movement between the sheath and the valve to advance the valve from the sheath for deployment in the heart.

In another representative embodiment, a method is provided for implanting a prosthetic, self-expanding heart valve in a patient's body. The method comprises mounting the valve in a radially compressed state within a sheath of a delivery apparatus, the valve being coupled to an elongated catheter of the delivery apparatus, inserting the delivery apparatus into the patient's vasculature and advancing the valve toward an implantation site, and rotating the catheter relative to the sheath, which causes relative longitudinally movement between the sheath and catheter to advance the valve from the sheath and expand.

In another embodiment, a heart-valve delivery apparatus for delivering a prosthetic, stented heart valve via a patient's vasculature comprises at least one elongated catheter having a distal end portion, and a valve-retaining mechanism coupling the valve to the distal end portion of the catheter. The retaining mechanism comprises a first fork and a second fork, each fork having a plurality of angularly spaced prongs, each prong of the first fork cooperating with a corresponding prong of the second fork to form a releasable connection with the stent of the valve, the second fork being movable relative to the first fork to release each connection formed by the prongs and the stent.

In another representative embodiment, a method is provided for implanting a prosthetic heart valve in a patient's body, the valve comprising a radially compressible and expandable stent. The method comprises connecting the valve in a compressed state to the distal end of a delivery apparatus via a retaining mechanism comprising a first fork and a second fork, each fork having a plurality of angularly spaced prongs, each prong of the first fork cooperating with a corresponding prong of the second fork to form a releasable connection with the stent of the valve. The method further comprises inserting the delivery apparatus into the patient's vasculature and advancing the valve to an implantation site in the heart, expanding the valve at a position at or adjacent the implantation site, and moving the second fork relative to the first fork to release each connection formed by the prongs and the stent, thereby releasing the valve from the delivery apparatus.

In yet another representative embodiment, a prosthetic heart valve for implantation at an implantation site having an annulus comprises a radially expandable and compressible support frame. The support frame comprises a plurality of strut members interconnected to each other to form a mesh structure comprising an inflow end and an outflow end. The mesh structure comprises a distended intermediate portion having a first diameter at a first location, the intermediate portion tapering in a direction toward the inflow end to form an inflow end portion having a second, smaller diameter at a second location. The valve further comprises plural leaflets having respective inflow end portions and outflow end portions, the inflow end portions of the leaflets being secured to the inside of the mesh structure at the inflow end portion of the mesh structure, and the outflow end portions of the leaflets defining angularly spaced commisures that are secured to the inside of the mesh structure at the outflow end of the mesh structure.

In another representative embodiment, a delivery apparatus for delivering a prosthetic heart valve comprises a first elongated shaft having a proximal end and a distal end adapted to be connected to the valve, and a second elongated shaft extending over the first shaft and having a proximal end and a distal end portion comprising a sheath configured to extend over the valve when the valve is in a radially compressed state. A handle is coupled to the proximal ends of the first and second shafts, the handle comprising a rotatable actuator and a screw operatively connected to the actuator and connected to the proximal end of the second shaft, wherein rotation of the actuator causes longitudinal movement of the screw and second shaft relative to the first shaft to retract the sheath relative to the valve.

In another representative embodiment, a delivery apparatus for delivering a prosthetic heart valve having a stent comprises at least one elongated catheter having a distal end portion, and a releasable valve-retaining mechanism adapted to form a releasable connection between the valve and the distal end portion of the catheter. The valve-retaining mechanism comprises a plurality of sutures extending from the distal end portion of the catheter, each suture extending through and engaging a portion of the stent and having a loop at one end. The valve-retaining mechanism further comprises an elongated slidable member extending through the loops of each suture so as to connect the valve to the catheter. The slidable member is retractable relative to the sutures to release the loops from the slidable member, thereby releasing the connection between the valve and the catheter.

In another representative embodiment, a delivery apparatus for delivering a prosthetic heart valve, comprises an elongated catheter having a distal end portion adapted to be coupled to the prosthetic valve, and a valve sheath. The valve sheath is configured to extend over the valve in a radially compressed state when coupled to the distal end portion of the catheter, and comprises a folded portion formed from a first tubular fold layer that extends over the valve and a second tubular fold layer that extends over the first fold layer. The second fold layer is movable longitudinally relative to the catheter and the valve to unsheathe the valve.

In another representative embodiment, an assembly comprises a prosthetic valve comprising a self-expanding stent, the stent having a plurality of angularly spaced posts, and a delivery apparatus for delivering the valve to an implantation site in a patient's body. The delivery apparatus comprises an elongated shaft having a distal end portion, the distal end portion having a plurality of recesses formed in an outer surface thereof and sized to receive respective posts of the stent. The delivery apparatus also comprises an outer sheath sized to extend over the valve and retain the valve in a compressed state with the posts disposed in respective recesses, the sheath and the shaft being movable longitudinally relative to each other to unsheathe the valve, thereby allowing it to expand.

In another representative, an introducer sheath comprising an elongated tubular sleeve having a lumen and adapted to be inserted into a patient's vasculature. The sleeve comprises a metallic layer comprising a plurality of bands spaced along a length of the metallic layer and circumferentially extending openings interposed between adjacent bands. The introducer sheath can further comprise a seal housing coupled to a proximal end of the sleeve.

In yet another representative embodiment, an introducer sheath comprises a housing having an inner bore, cap portion movable longitudinally on the housing, an elastomeric seal mounted to the cap portion and having an opening aligned with the inner bore. The cap portion is movable from a first position to a second position on the housing to stretch the seal in the radial direction in order to dilate the opening in the seal. The introducer sheath can also include an elongated tubular sleeve extending from the inner bore of the housing, the sleeve having a lumen and adapted to be inserted into a patient's vasculature.

The foregoing and other features and advantages of the invention will become more apparent from the following detailed description, which proceeds with reference to the accompanying figures.

BRIEF DESCRIPTION OF THE DRAWINGS

FIG. 9 is a side view of the distal end portion of the delivery apparatus shown with a sheath extending over and covering a valve for delivery through a patient's vasculature.

FIG. 10 is a side view of the distal end portion of the delivery apparatus shown with the sheath retracted to allow the valve to expand to its functional size.

FIG. 11 is a cross-section view of the distal end portion of the delivery apparatus.

FIG. 12 is a cross-sectional view of a portion of the delivery apparatus showing the inside of the sheath.

FIGS. 19 and 20 show the distal end portion of a torque catheter being connected to an inner fork of the retaining mechanism.

FIGS. 21 and 22 show a screw member disposed on the torque catheter being connected to an outer fork of the retaining mechanism.

FIGS. 23 and 24 show the compressed valve being loaded into the sheath of the delivery apparatus.

FIG. 25 is a side view of the delivery apparatus showing the sheath partially retracted.

FIG. 30 is a side view of the distal end portion of another embodiment of a delivery apparatus.

FIG. 31 is a side view similar to FIG. 30 showing the sheath of the delivery apparatus in a partially retracted position.

FIG. 32 is a side view similar to FIG. 30 shown with the sheath removed for purposes of illustration.

FIG. 33 is a side view similar to FIG. 32 showing a portion of the delivery apparatus in a bent position. This figure illustrates that the delivery apparatus can exhibit sufficient flexibility along the portion containing the screw mechanism.

FIG. 34 is a perspective view of the handle portion of the delivery apparatus shown in FIG. 30, according to one embodiment.

FIG. 35 is a perspective view illustrating the inside of the handle portion.

FIG. 39 is a side view of another embodiment of a delivery apparatus.

FIG. 45 is an enlarged, front elevation view of the engagement latch of the adjustment knob shown in FIG. 43.

FIG. 54A is a perspective view of a delivery apparatus for a prosthetic valve shown with the sheath of the delivery apparatus in a retracted position for deploying the valve, according to another embodiment.

FIG. 54B is a perspective view of the delivery apparatus of FIG. 54A shown with the sheath in a distal position for covering the valve during valve delivery.

FIG. 54C is an enlarged, perspective view of an end piece of the delivery apparatus of FIG. 54A and three posts of a valve stent that are received within respective recesses in the end piece.

FIG. 54D is a cross-sectional view of the end piece shown in FIG. 54C.

FIGS. 57A and 57B are cross-sectional views of an introducer sheath and loader assembly, according to one embodiment.

FIG. 58A is a perspective view of an introducer sheath, according to another embodiment.

FIG. 58B is an enlarged, perspective view of the sleeve of the introducer sheath of FIG. 58A.

FIG. 59 is an enlarged, perspective view of another embodiment of a sleeve that can be used with the introducer sheath of FIG. 58A.

FIG. 60 is an end view of a sleeve that can be used with the introducer sheath of FIG. 58A.

DETAILED DESCRIPTION

Figure 1:
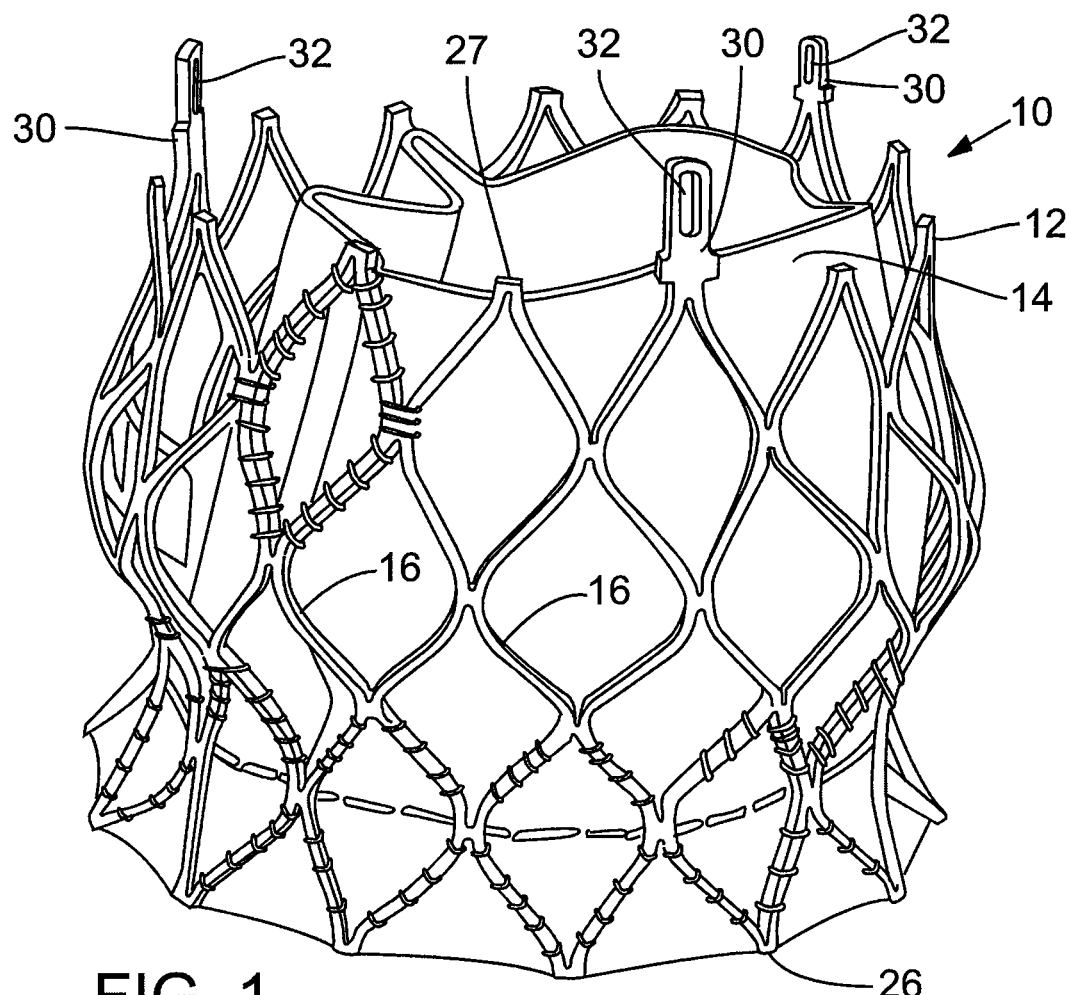
FIG. 1 is a perspective view of a prosthetic valve that can be used to replace the native aortic valve of the heart.

Referring first to FIG. 1, there is shown a prosthetic aortic heart valve 10, according to one embodiment. The valve 10 includes an expandable frame member, or stent, 12 that supports a flexible leaflet section 14. The valve 10 is radially compressible to a compressed state for delivery through the body to a deployment site and expandable to its functional size shown in FIG. 1 at the deployment site. In certain embodiments, the valve 10 is self-expanding; that is, the valve can radially expand to its functional size when advanced from the distal end of a delivery sheath. Apparatuses particularly suited for percutaneous delivery and implantation of a self-expanding valve are described in detail below. In other embodiments, the valve can be a balloon-expandable valve that can be adapted to be mounted in a compressed state on the balloon of a delivery catheter. The valve can be expanded to its functional size at a deployment site by inflating the balloon, as known in the art.

The illustrated valve 10 is adapted to be deployed in the native aortic annulus, although it also can be used to replace the other native valves of the heart. Moreover, the valve 10 can be adapted to replace other valves within the body, such a venous valve.

Figure 3:
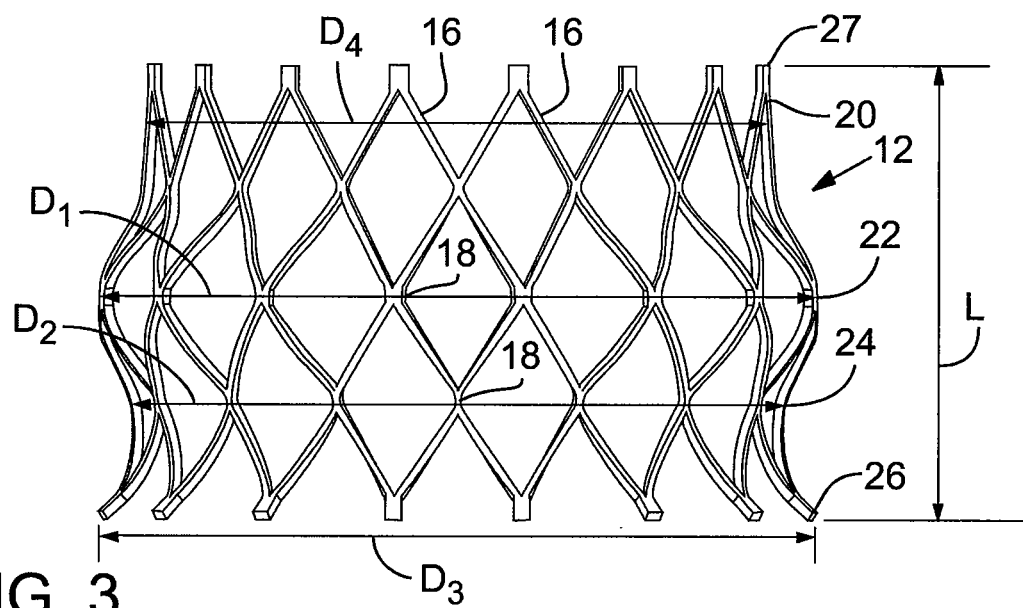
FIG. 3 is side elevation view of the support frame of the valve of FIG. 1.
Figure 4:
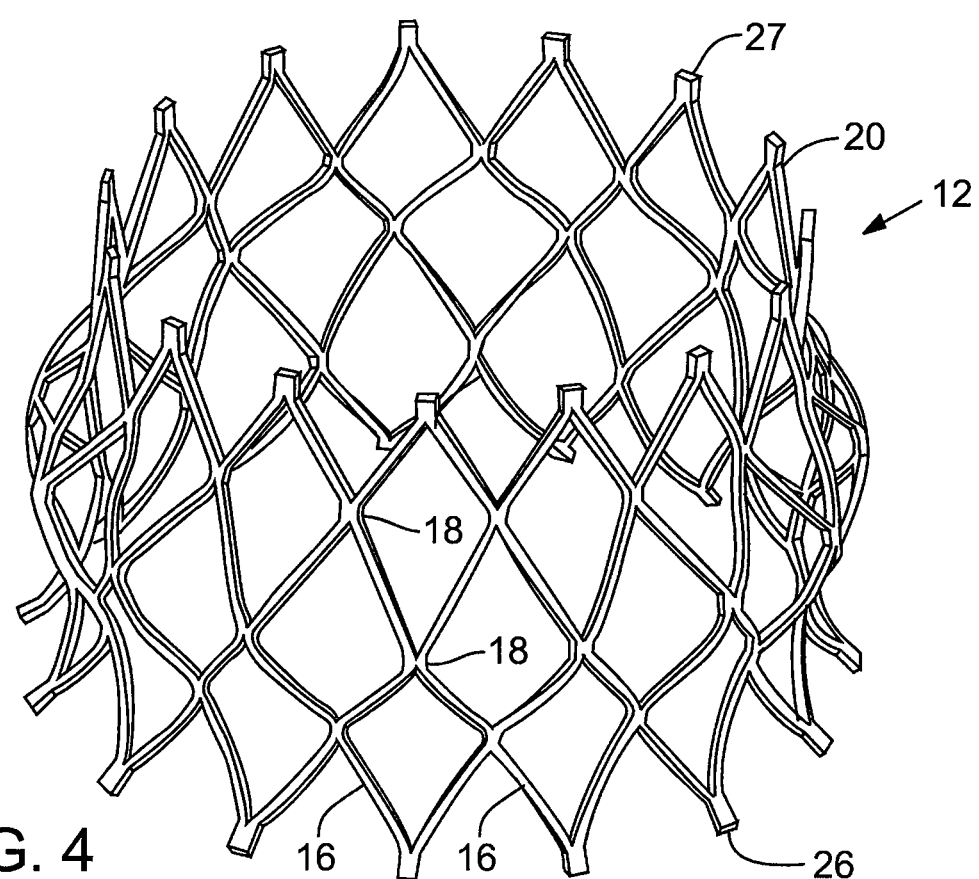
FIG. 4 is a perspective view of the support frame of the valve of FIG. 1.

FIGS. 3 and 4 show the stent 12 without the leaflet section 14 for purposes of illustration. As shown, the stent 12 can be formed from a plurality of longitudinally extending, generally sinusoidal shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the valve to be compressed to a reduced diameter for delivery in a delivery apparatus (such as described below) and then causes the valve to expand to its functional size inside the patient's body when deployed from the delivery apparatus. If the valve is a balloon-expandable valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the Valsalva sinuses in the root of the aorta to assist in anchoring the valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

Figure 5A:
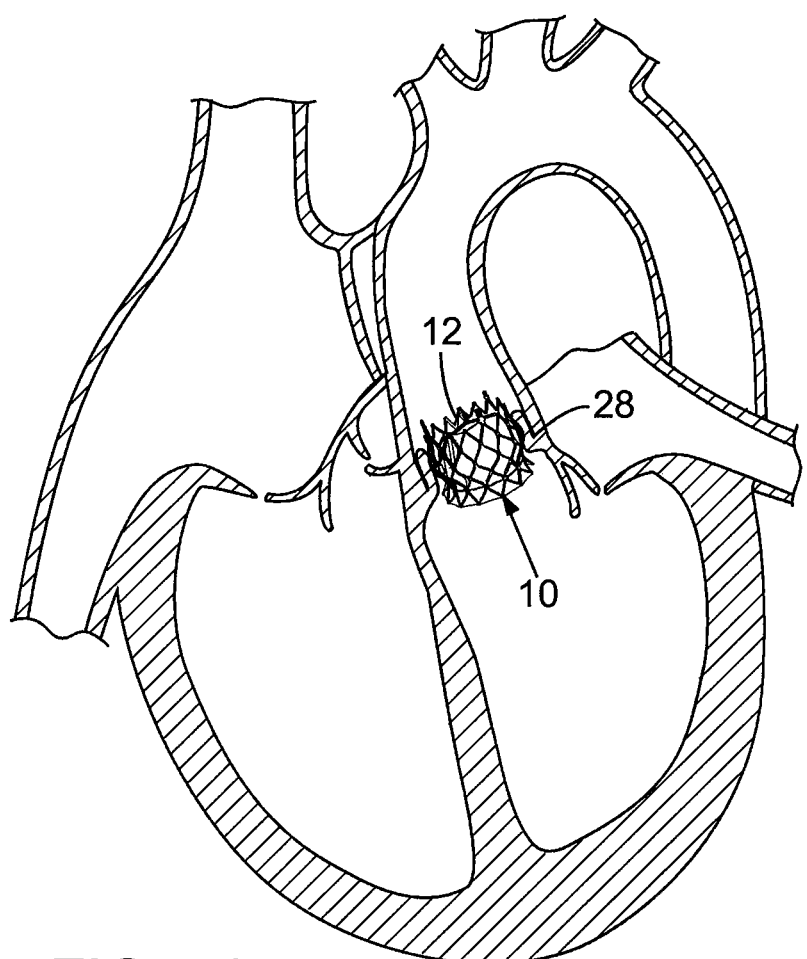
FIG. 5A is a cross-sectional view of the heart showing the prosthetic valve of FIG. 1 implanted within the aortic annulus.
Figure 5B:
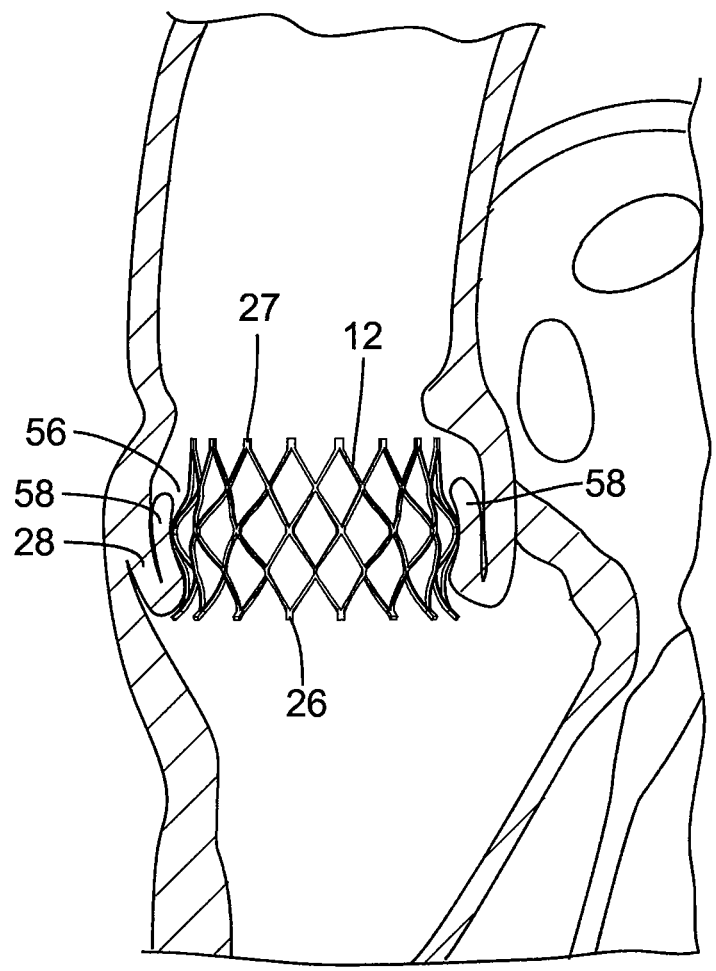
FIG. 5B is an enlarged view of FIG. 5A illustrating the prosthetic valve implanted within the aortic annulus, shown with the leaflet structure of the valve removed for clarity.

When the valve is in its expanded state, the intermediate section 22 has a diameter $D_1$, the inflow end portion 24 has a minimum diameter $D_2$, the inflow end 26 has a diameter $D_3$, and the outflow end portion 20 has a diameter $D_4$, where $D_2$ is less than $D_1$ and $D_3$ and $D_4$ is less than $D_2$. In addition, $D_1$ and $D_3$ desirably are greater than the diameter than the native annulus in which the valve is to be implanted. In this manner, the overall shape of the stent 12 assists in retaining the valve at the implantation site. More specifically, and referring to FIGS. 5A and 5B, the valve 10 can be implanted within a native valve (the aortic valve in the illustrated example) such that the lower section 24 is positioned within the aortic annulus 28, the intermediate section 24 extends above the aortic annulus into the Valsalva's sinuses 56, and the lower flared end 26 extends below the aortic annulus. The valve 10 is retained within the native valve by the radial outward force of the lower section 24 against the surrounding tissue of the aortic annulus 28 as well as the geometry of the stent. Specifically, the intermediate section 24 and the flared lower end 26 extend radially outwardly beyond the aortic annulus 28 to better resist against axial dislodgement of the valve in the upstream and downstream directions (toward and away from the aorta). Depending on the condition of the native leaflets 58, the valve typically is deployed within the native annulus 28 with the native leaflets 58 folded upwardly and compressed between the outer surface of the stent 12 and the walls of the Valsalva sinuses, as depicted in FIG. 5B. In some cases, it may be desirable to excise the leaflets 58 prior to implanting the valve 10.

Known prosthetic valves having a self-expanding frame typically have additional anchoring devices or frame portions that extend into and become fixed to non-diseased areas of the vasculature. Because the shape of the stent 12 assists in retaining the valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the valve.

In particular embodiments, for a valve intended for use in a 22-mm to 24-mm annulus, the diameter D1 is about 28 mm to about 32 mm, with 30 mm being a specific example; the diameter D2 is about 24 mm to about 28 mm, with 26 mm being a specific example; the diameter D3 is about 28 mm to about 32 mm, with 30 mm being a specific example; and the diameter D4 is about 24 mm to about 28 mm, with 26 mm being a specific example. The length L in particular embodiments is about 20 mm to about 24 mm, with 22 mm being a specific example.

Referring to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the valve and a delivery apparatus (described below). In alternative embodiments, the retaining arms 30 need not be provided if a valve-retaining mechanism is not used.

Figure 6:
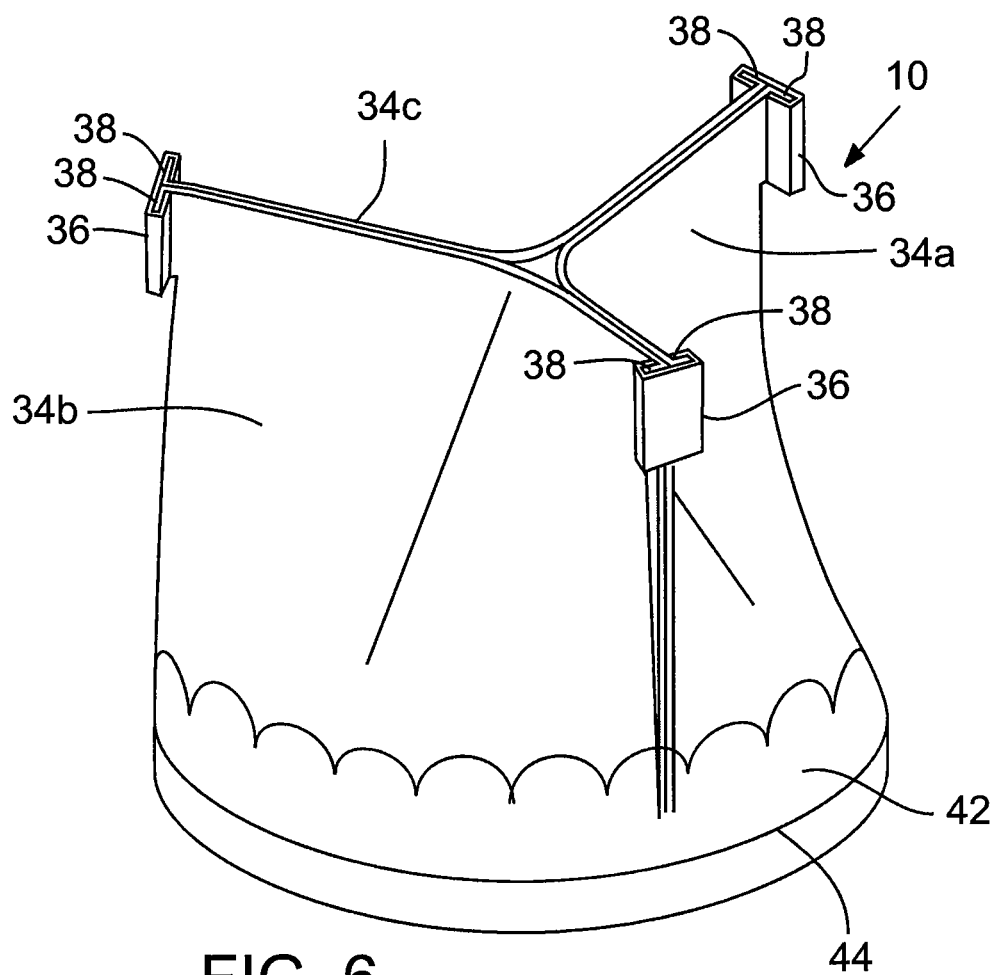
FIG. 6 is a perspective view of the leaflet structure of the valve of FIG. 1 shown prior to being secured to the support frame.
Figure 7:
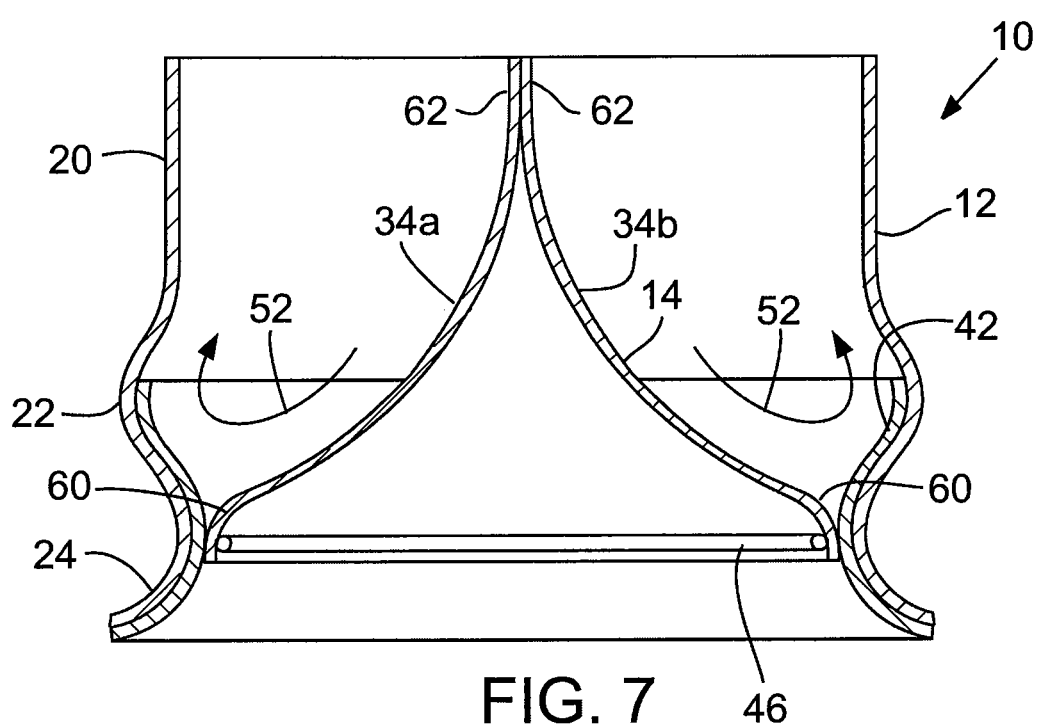
FIG. 7 is a cross-sectional view of the valve of FIG. 1.

As best shown in FIGS. 6 and 7, the leaflet assembly 14 in the illustrated embodiment comprises three leaflets 34a, 34b, 34c made of a flexible material. Each leaflet has an inflow end portion 60 and an outflow end portion 62. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 14 can include an annular reinforcing skirt 42 that is secured to the outer surfaces of the inflow end portions of the leaflets 34a, 34b, 34c at a suture line 44 adjacent the inflow end of the valve. The inflow end portion of the leaflet assembly 14 can be secured to the stent 12 by suturing the skirt 42 to struts 16 of the lower section 24 of the stent (best shown in FIG. 1). As shown in FIG. 7, the leaflet assembly 14 can further include an inner reinforcing strip 46 that is secured to the inner surfaces of the inflow end portions 60 of the leaflets.

Figure 2:
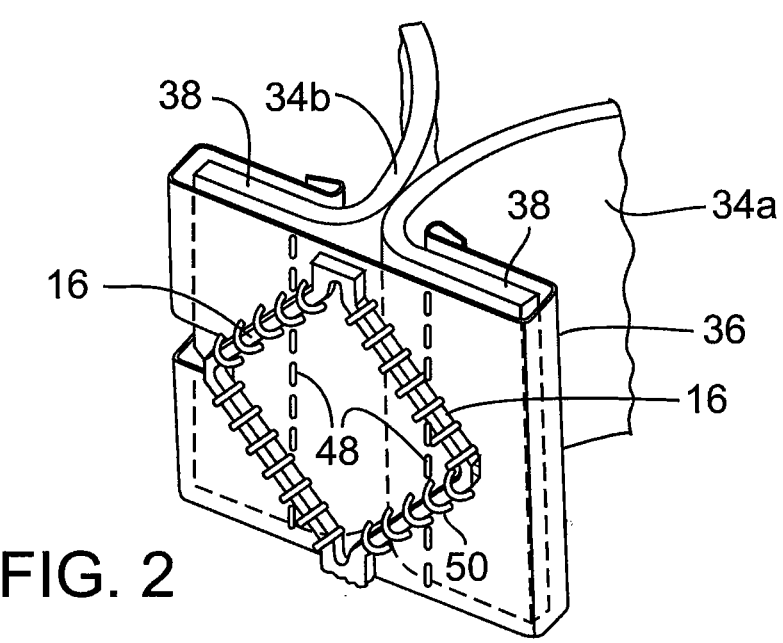
FIG. 2 is a perspective view of a portion of the valve of FIG. 1 illustrating the connection of two leaflets to the support frame of the valve.

Referring to FIGS. 1 and 2, the outflow end portion of the leaflet assembly 14 can be secured to the upper portion of the stent 12 at three angularly spaced commissure attachments of the leaflets 34a, 34b, 34c. As best shown in FIG. 2, each commissure attachment can be formed by wrapping a reinforcing section 36 around adjacent upper edge portions 38 at the commissure of two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end of the stent. The leaflets therefore desirably extend the entire length or substantially the entire length of the stent from the inflow end 26 to the outflow end 27. The reinforcing sections 36 reinforces the attachment of the leaflets to the stent so as to minimize stress concentrations at the suture lines and avoid "needle holes" on the portions of the leaflets that flex during use. The reinforcing sections 36, the skirt 42, and the inner reinforcing strip 46 desirably are made of a bio-compatible synthetic material, such as polytetrafluoroethylene (PTFE), or a woven fabric material, such as woven polyester (e.g., polyethylene terephthalate) (PET)).

FIG. 7 shows the operation of the valve 10. During diastole, the leaflets 34a, 34b, 34c collapse to effectively close the valve. As shown, the curved shape of the intermediate section 22 of the stent 12 defines a space between the intermediate section and the leaflets that mimics the Valsalva sinuses. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize clot formation.

The valve 10 can be implanted in a retrograde approach where the valve, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

Figure 8:
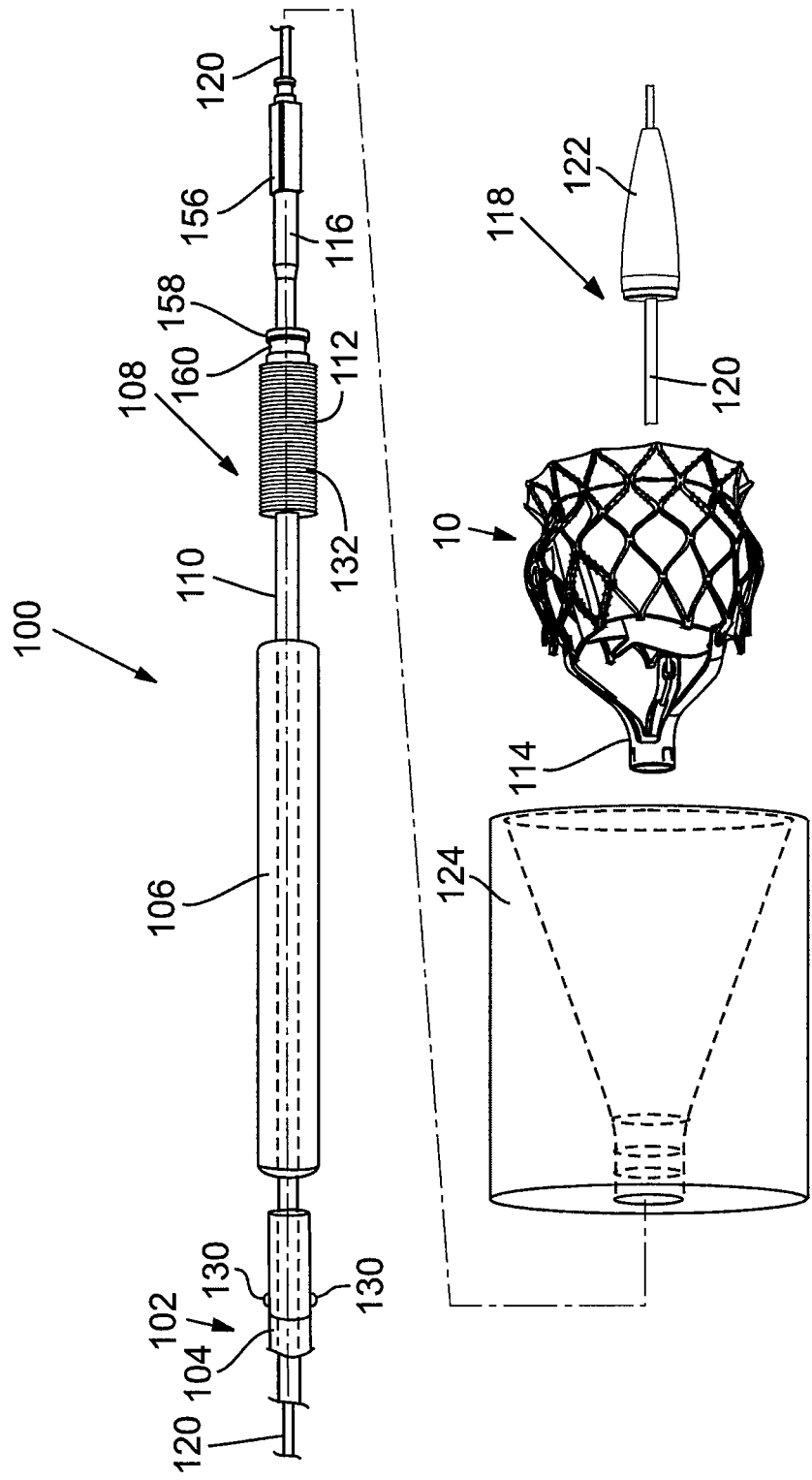
FIG. 8 is an exploded view of a delivery apparatus that can be used to deliver and implant a prosthetic valve, such as the prosthetic valve shown in FIG. 1.

FIG. 8 shows a delivery apparatus 100, according to one embodiment, that can be used to deliver a self-expanding valve, such as valve 10 described above, through a patient's vasculature. The delivery apparatus 100 comprises a first, outermost or main catheter 102 having an elongated shaft 104, the distal end of which is coupled to a delivery sheath 106 (also referred to as a delivery cylinder). The proximal end of the main catheter 102 is connected to a handle of the delivery apparatus (not shown). During delivery of a valve, the handle can be used by a surgeon to advance and retract the delivery apparatus through the patient's vasculature. Although not required, the main catheter 102 can comprise a guide catheter that is configured to allow a surgeon to guide or control the amount the bending or flexing of a distal portion of the shaft 104 as it is advanced through the patient's vasculature, such as disclosed in U.S. Patent Publication No. 2008/0065011.

The delivery apparatus 100 also includes a second catheter 108 (also referred to herein as a valve catheter) having an elongated shaft 110 (also referred to herein as a torque shaft), a cylindrical screw 112 disposed on the shaft 110, and a valve-retaining mechanism 114 connected to a distal end portion 116 of the shaft 110. The shaft 110 of the valve catheter 108 extends through the delivery sheath 106 and the shaft 104 of the main catheter 102. The delivery apparatus 100 can also include a third, nose catheter 118 having an elongated shaft 120 and a nose piece 122 secured to the distal end portion of the shaft 120. The nose piece 122 can have a tapered outer surface as shown for atraumatic tracking through the patient's vasculature. The shaft 120 of the nose catheter extends through the valve 10, the retaining mechanism 114, and the shaft 110 of the valve catheter 108. The torque shaft 110 of valve catheter 108 can be configured to be movable axially and rotatable relative to the shaft 104 of the main catheter and the shaft 120 of the nose catheter. The delivery apparatus 100 can also be provided with a loading cone 124 that can be used to load the valve 10 in a compressed state inside the delivery sheath 106, as further described below.

The distal end portion 116 of the valve catheter shaft 110 can include an end piece 156 on which the screw 112 is mounted. The end piece 156 has a non-circular cross-sectional profile extending at least partially along the length of the end piece that mates with a similarly shaped inner surface of the screw 112 (as best shown in FIG. 11). For example, in the illustrated embodiment, a portion of the end piece 156 has a square cross-sectional profile that mates with a square shaped inner surface of the screw 112. In this manner, rotation of the shaft 110 causes corresponding rotation of the screw 112.

The valve catheter 108 desirably is configured to be rotatable relative to the delivery sheath 106 to effect incremental and controlled advancement of the valve 10 from the delivery sheath. To such ends, and according to one embodiment, the delivery sheath 106 (as best shown in FIGS. 9-12) can include first and second elongated cam slots 126 and internal threads 128 adapted to engage external threads 132 of screw 112. The distal end portion of the main catheter shaft 104 extends into the delivery sheath 106 and can be formed with first and second projections 130 that extend radially outwardly into the cam slots 126 of the delivery sheath.

As best shown in FIG. 11, the distal end portion of shaft 110 extends over and is secured to a proximal end portion of the end piece 156, such as with an adhesive. The screw 112 is disposed on the end piece 56 within the delivery sheath 106. The distal end of the screw 112 and the end piece 56 are coupled to the valve 10 via the retaining member 114 such that rotation of the valve catheter shaft 110 is effective to cause corresponding rotation of the end piece 56, the screw 112 and the valve 10. Rotation of the shaft 110 and the screw 112 relative to the sheath 106 is effective to move the shaft 110 and the valve 10 longitudinally in either the proximal or distal directions (as indicated by arrows 134*a* and 134*b*, respectively) relative to the sheath 106. During valve deployment, movement of the shaft 110 in the proximal direction causes the valve 10 to advance from the open distal end 136 of the sheath, as further described below.

Figure 13:
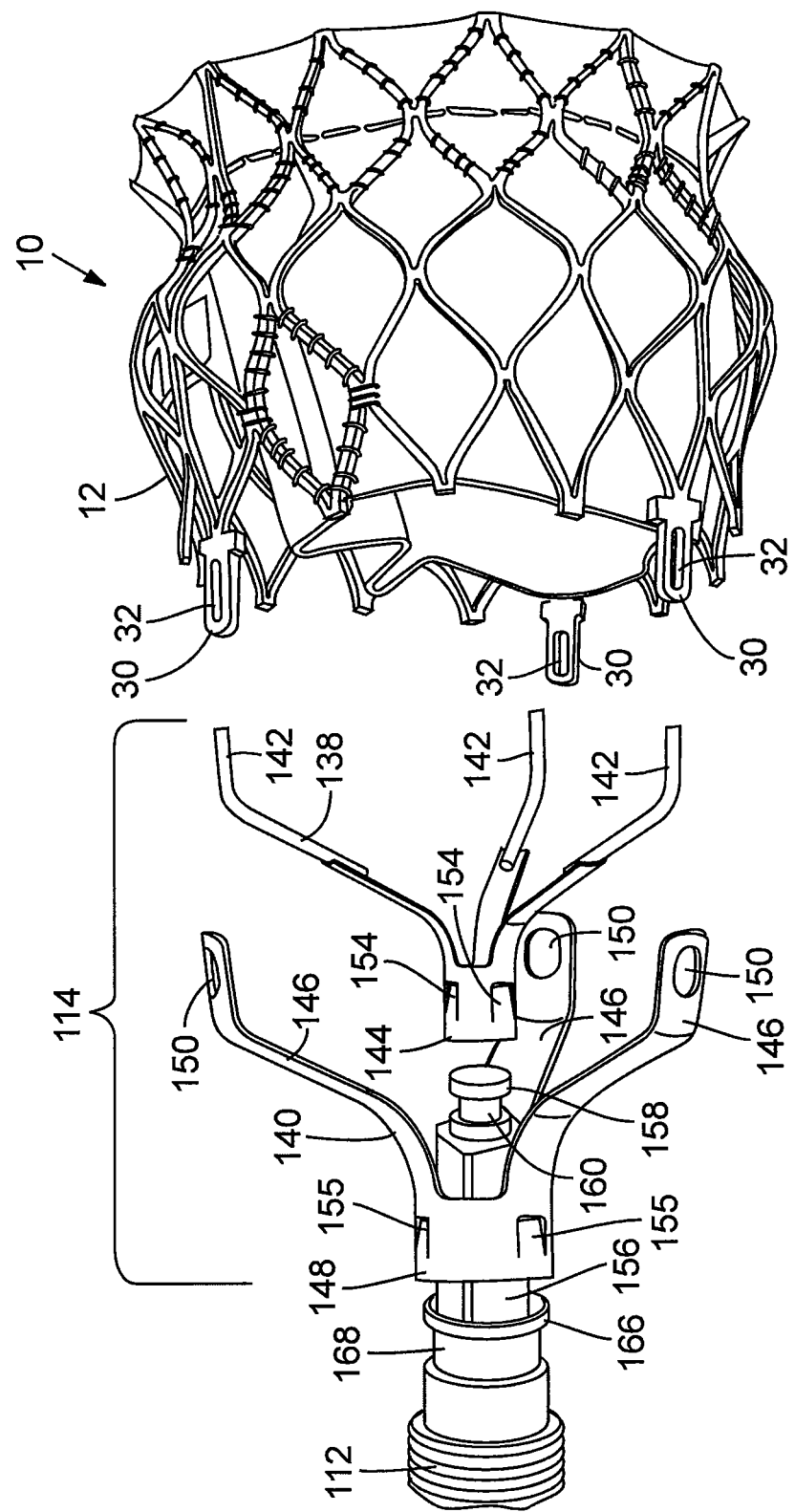
FIG. 13 is an exploded, perspective view of the valve and a retaining mechanism that forms a releasable connection between the valve and the delivery apparatus.
Figure 14:
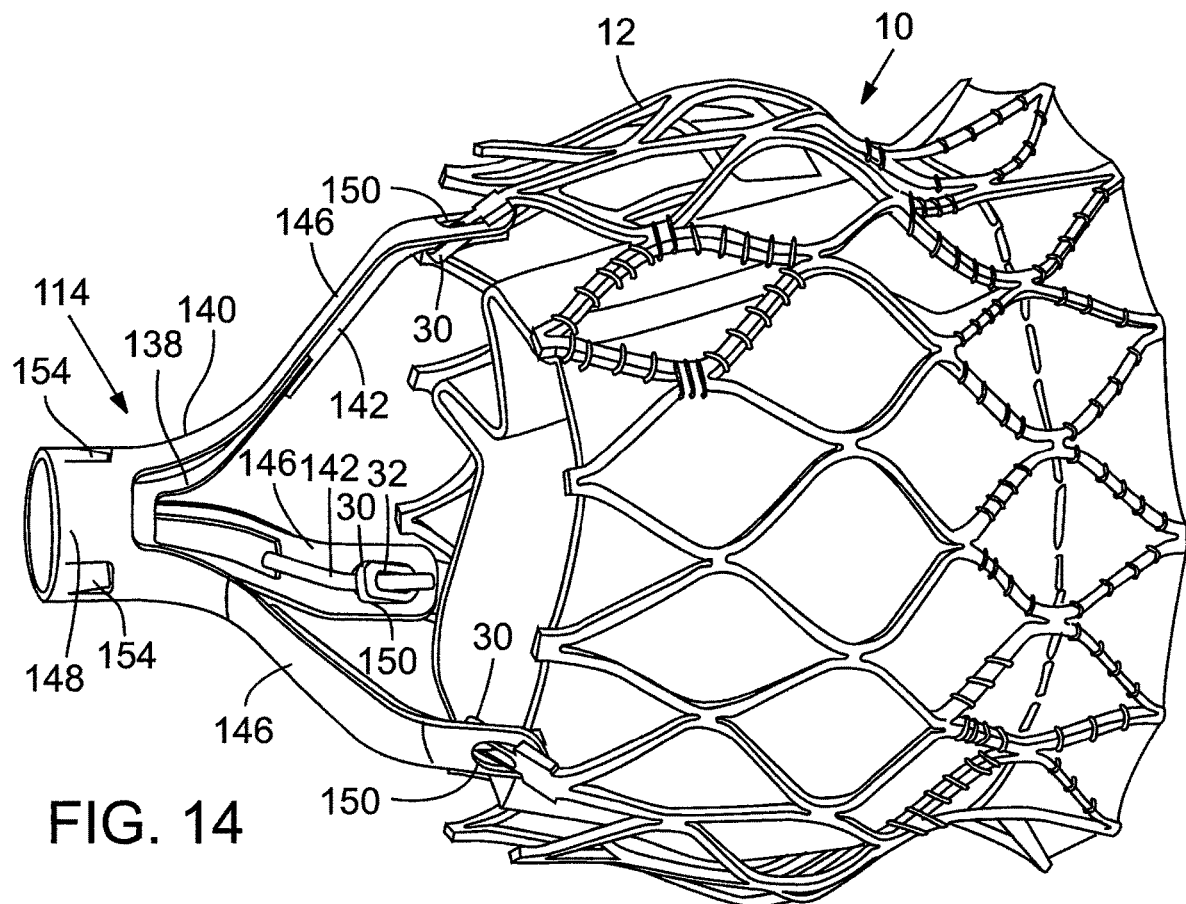
FIG. 14 is a perspective view showing the valve connected to the retaining mechanism.

As best shown in FIGS. 13 and 14, the valve-retaining mechanism 114 includes an inner fork 138 an outer fork 140. The inner fork 138 includes a plurality of angularly-spaced prongs 142 (three in the illustrated embodiment) corresponding to the retaining arms 30 of the stent 12, which prongs extend from a head portion 144 at the proximal end of the inner fork. The outer fork 140 similarly includes a plurality of angularly-spaced prongs 146 (three in the illustrated embodiment) corresponding to the retaining arms 30 of the stent 12, which prongs extend from a head portion 148 at the proximal end of the outer fork.

Figure 15:
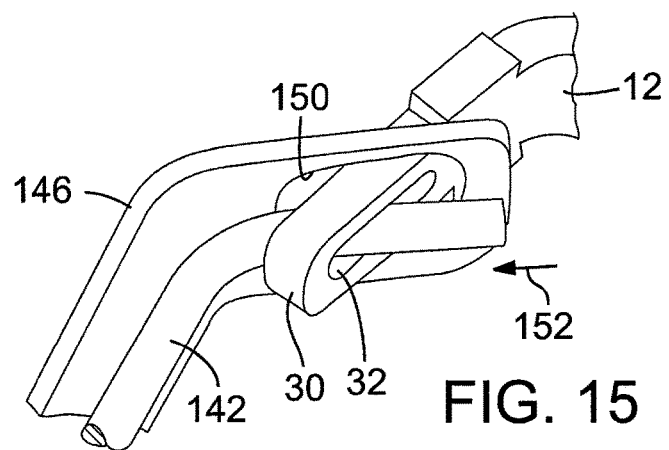
FIG. 15 is an enlarged, perspective view of a portion of the retaining mechanism illustrating two prongs of the retaining cooperating to form a releasable connection with the support frame of the valve.

Each prong of the outer fork cooperates with a corresponding prong of the inner fork to form a releasable connection with a retaining arm 30 of the stent. In the illustrated embodiment, for example, the distal end portion of each prong 146 is formed with an opening 150. When assembled (as best shown in FIG. 15), each retaining arm 30 of the stent is inserted through an opening 150 of a prong 146 of the outer fork and a prong 142 of the inner fork is inserted through the opening 32 of the retaining arm 30 so as to retain the retaining arm 30 from backing out of the opening 150. As can be seen, retracting the prongs 142 proximally (in the direction of arrow 152) to remove the prongs from the openings 32 is effective to release the valve 10 from the retaining mechanism. In this manner, the retaining mechanism 114 forms a releasable connection with the valve that is secure enough to retain the valve relative to the valve catheter 108 to allow the user to fine tune or adjust the position of the valve after it is deployed from the delivery sheath. When the valve is positioned at the desired implantation site, the connection between the valve and the retaining mechanism can be released by retracting the inner fork 138 relative to the outer fork 140, as further described below.

Figure 16:
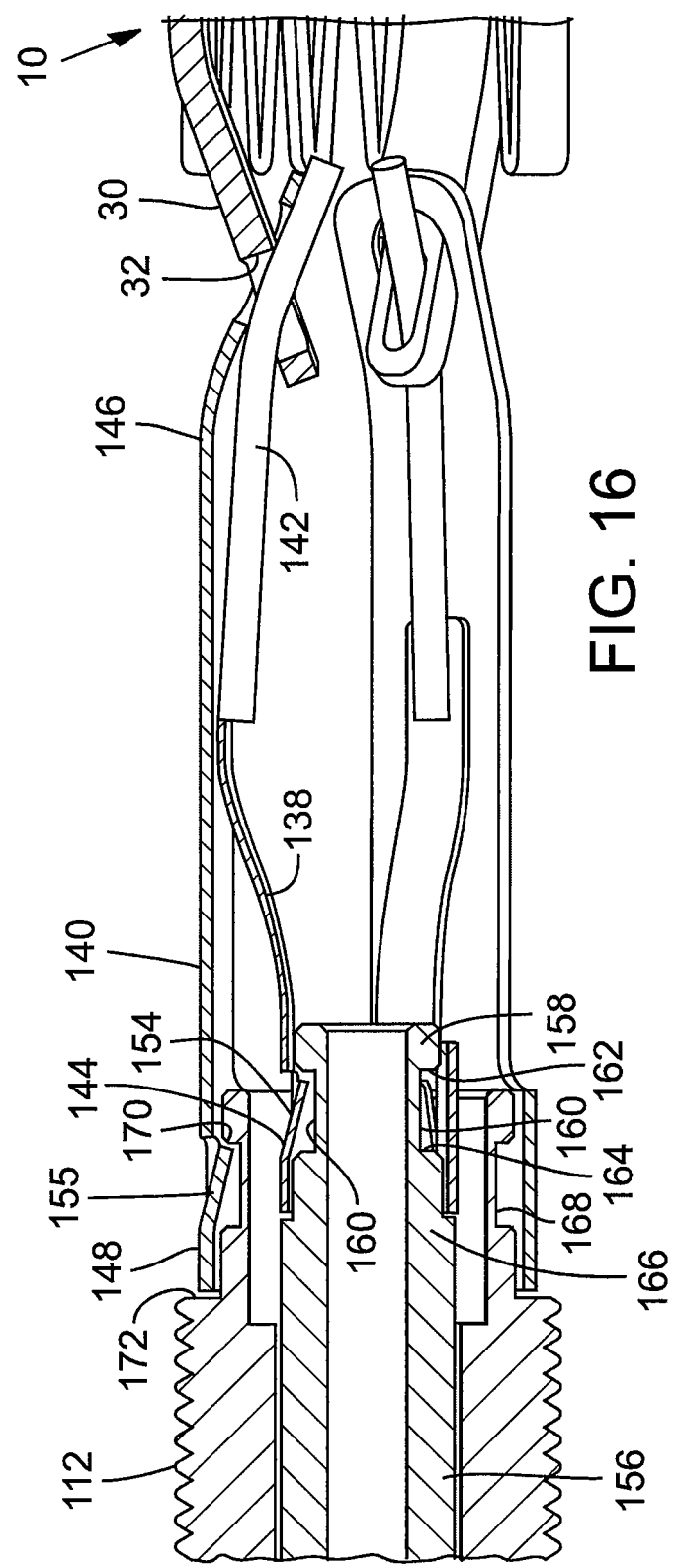
FIG. 16 is an enlarged, cross-sectional view of a portion of the delivery apparatus.

The head portion 144 of the inner fork can be connected to the valve catheter shaft 110 while the head portion 148 can be connected to the screw 112. As shown in FIG. 13, for example, the head portion 144 of the inner fork can be formed with a plurality of angularly spaced, inwardly biased retaining flanges 154. The end piece 156 of the valve catheter shaft 110 can be formed with a cylindrical shaft 158 having an annular groove 160. The shaft 158 has an outer diameter that is slightly greater than the diameter defined by the inner free ends of the flanges 154. Thus, the inner fork 138 can be secured to the end piece 156 by inserting the shaft 158 into the head portion 144 until the flanges 154 flex inwardly into the groove 160, thereby forming a snap-fit connection between the head portion 144 and the shaft 158. As can be seen in FIG. 16, when the head portion 144 is inserted onto the shaft 158, an annular shoulder 162 within the groove 160 is positioned opposite the free ends of flanges 154 and another annular shoulder 164 of end piece 156 is positioned opposite the proximal end of the head portion 144 to prevent the end piece 156 from moving longitudinally in the distal and proximal directions relative to the inner fork.

The head portion 148 of the outer fork can be secured to the distal end of the screw 112 in a similar manner. As best shown in FIG. 16, the head portion 148 can be formed with a plurality of angularly spaced, inwardly biased retaining flanges 155. The distal end portion of the screw 112 can be formed with a cylindrical shaft 166 having an annular groove 168. The shaft 166 has an outer diameter that is slightly greater than the diameter defined by the free ends of the flanges 155. Thus, the outer fork 140 can be secured to the screw 112 by inserting the shaft 166 into the head portion 148 until the flanges flex inwardly into the groove 168, thereby forming a snap-fit connection between the head portion 148 and the shaft 166. As can be seen in FIG. 16, when the head portion 148 is inserted onto the shaft 166, an annular shoulder 170 within the groove 168 is positioned opposite the free ends of flanges 156 and another annular shoulder 172 of the screw 112 is positioned opposite the proximal end of the head portion to prevent the screw from moving longitudinally in the distal and proximal directions relative to the outer fork.

Figure 17:
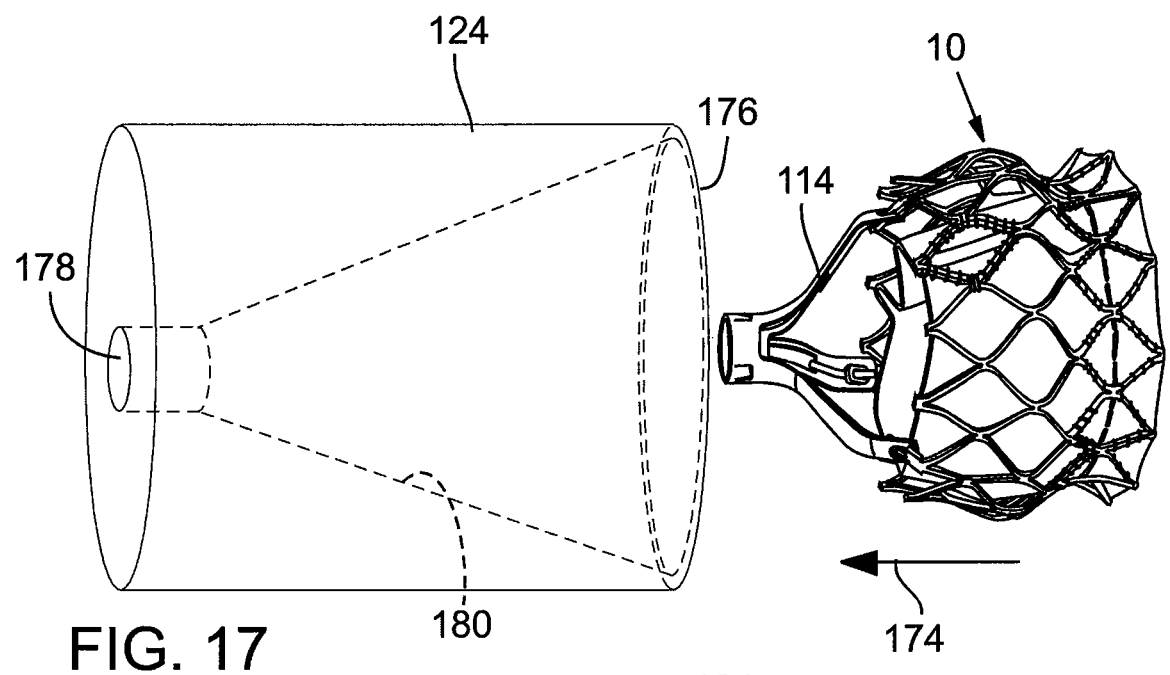
FIG. 17 is a perspective view of the valve and a loading cone that can be used to radially compress the valve to a compressed stated for loading into the sheath.
Figure 18:
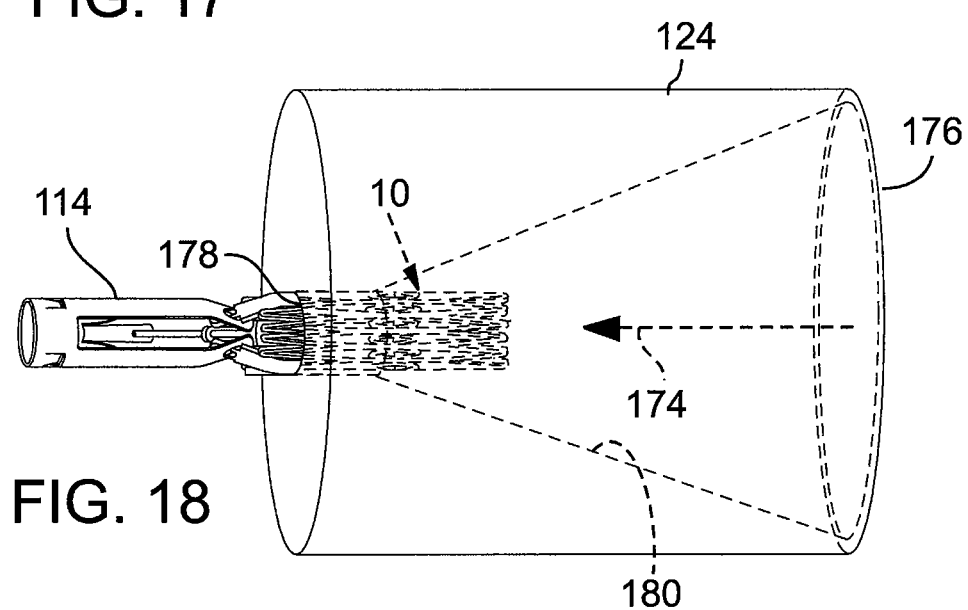
FIG. 18 shows the valve being inserted through the cone to compress the valve.

The valve 10 can be compressed and loaded into the delivery sheath 106 using the loading cone 124 in the following manner. First, as shown in FIG. 17, the valve 10 can be secured to the retaining mechanism 114 as described above. The loading cone 124 includes a first opening 176 at one end, a second, smaller opening 178 at the opposite end, and a tapered inner surface 180 that tapers from a first diameter at the first opening to a second, smaller diameter proximate the second opening 178. As shown in FIG. 18, the retaining mechanism 114 and the valve 10 can be pushed through the loading cone 124 in the direction of arrow 174 to radially compress the retaining member and the valve until the retaining member 114 extends outside the loading cone. To facilitate compression of the valve, the latter step can be performed while immersing the valve and the retaining mechanism in a bath of cold water.

Referring to FIGS. 19 and 20, while the valve is retained in its compressed state by the loading cone 124, the end piece 156 is secured to the inner fork by inserting the shaft 158 into the head portion 144 of the inner fork in the direction of arrow 182 as described above. Referring to FIGS. 21 and 22, the screw 112 can then be slid over the end piece 156 in the direction of arrow 184 and secured to the outer fork 140 by inserting the shaft 166 into the head portion 148 of the outer fork as described above. Subsequently, referring to FIGS. 23 and 24, the delivery sheath 106 is placed over the screw 112 by bringing the proximal end of the screw in contact with the distal end of the sheath 106 and then rotating the valve catheter shaft 110, which causes the sheath to advance over the screw. Continued rotation of the shaft 110 causes the sheath 106 to advance over the retaining member 114 and the valve 10 and then push away the loading cone to allow the sheath to advance over the valve as it exits the loading cone. The shaft 110 is rotated until the valve is completely inside the sheath, as depicted in FIGS. 9 and 11.

When nose cone 122 is used, the nose cone desirably has an outer diameter less than the opening 178 of the loading cone so that the nose cone can slide through the loading cone along with the valve 10. In alternative embodiments, a conventional crimping mechanism can be used to radially compress the valve 10.

Once the valve 10 is loaded in the delivery sheath 106, the delivery apparatus 100 can be inserted into the patient's body for delivery of the valve. In one approach, the valve can be delivered in a retrograde procedure where delivery apparatus is inserted into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the valve 10 is advanced to a location adjacent to or within the native aortic valve.

Thereafter, the valve 10 can be deployed from the delivery apparatus 100 by rotating the valve catheter 108 relative to the guide catheter 102. As noted above, the valve catheter can have a rotatable handle portion (not shown) connected to the proximal end of the valve catheter shaft 110 that allows the surgeon to effect rotation of the valve catheter 108 relative to the main catheter 102. Rotation of the valve catheter 108 causes corresponding rotation of the valve catheter shaft 110, the end piece 156, and the screw 112 relative to the main catheter shaft 104 and the sheath, which in turn causes these components to advance distally relative to the delivery sheath 106 to advance the valve 10 from the open end of the sheath. Rotation of the valve catheter 108 causes the valve to move relative to sheath in a precise and controlled manner as the valve advances from the open distal end of the delivery sheath and begins to expand. Hence, unlike known delivery apparatus, as the valve begins to advance from the delivery sheath and expand, the valve is held against uncontrolled movement from the sheath caused by the expansion force of the valve against the distal end of the sheath. In addition, after the valve is partially advanced from the sheath, it may be desirable to retract the valve back into the sheath, for example, to reposition the valve or to withdraw the valve entirely from the body. The partially deployed valve can be retracted back into the sheath by reversing the rotation of the valve catheter, which causes the catheter shaft 110 to retract and pull the valve back into the sheath.

In known delivery devices, the surgeon must apply push-pull forces to the shaft and/or the sheath to unsheathe the valve. It is therefore difficult to transmit forces to the distal end of the device without distorting the shaft (e.g., compressing or stretching the shaft axially), which in turn causes uncontrolled movement of the valve during the unsheathing process. To mitigate this effect, the shaft and/or sheath can be made more rigid, which is undesirable because the device becomes harder to steer through the vasculature. In contrast, the manner of unsheathing the valve described above eliminates the application of push-pull forces on the shaft, as required in known devices, so that relatively high and accurate forces can be applied to the distal end of the shaft without compromising the flexibility of the device. In certain embodiments, as much as 20 lbs. of force can be transmitted to the end of the torque shaft without adversely affecting the unsheathing process. In contrast, prior art devices utilizing push-pull mechanisms typically cannot exceed about 5 lbs. of force during the unsheathing process.

Figure 26:
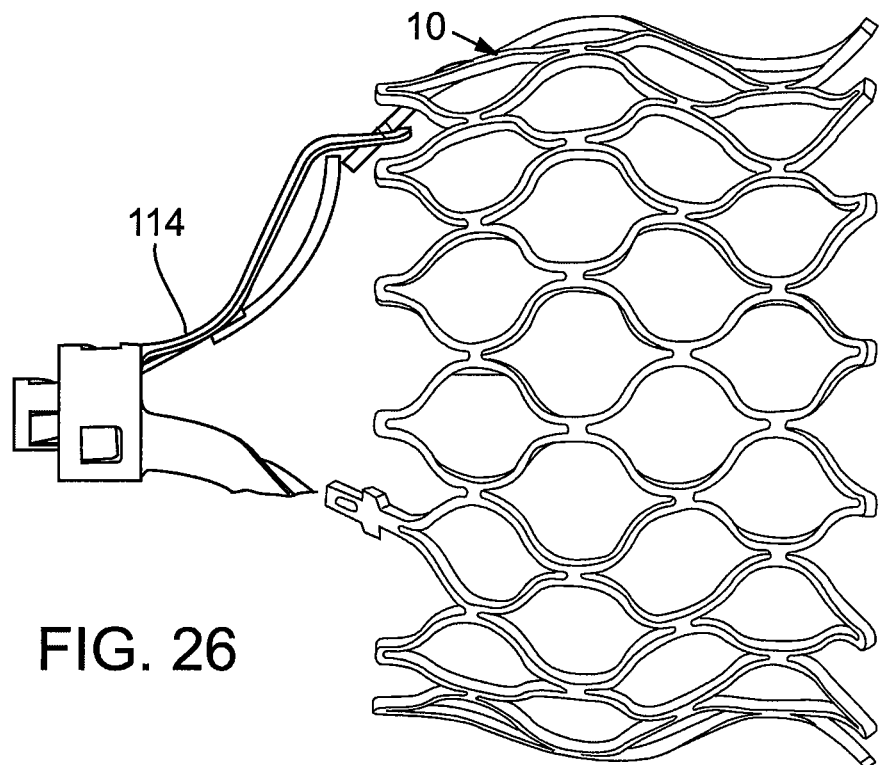
FIGS. 26 and 27 show the inner fork of the retaining mechanism being retracted relative to the outer fork to release the valve from the retaining mechanism.
Figure 27:
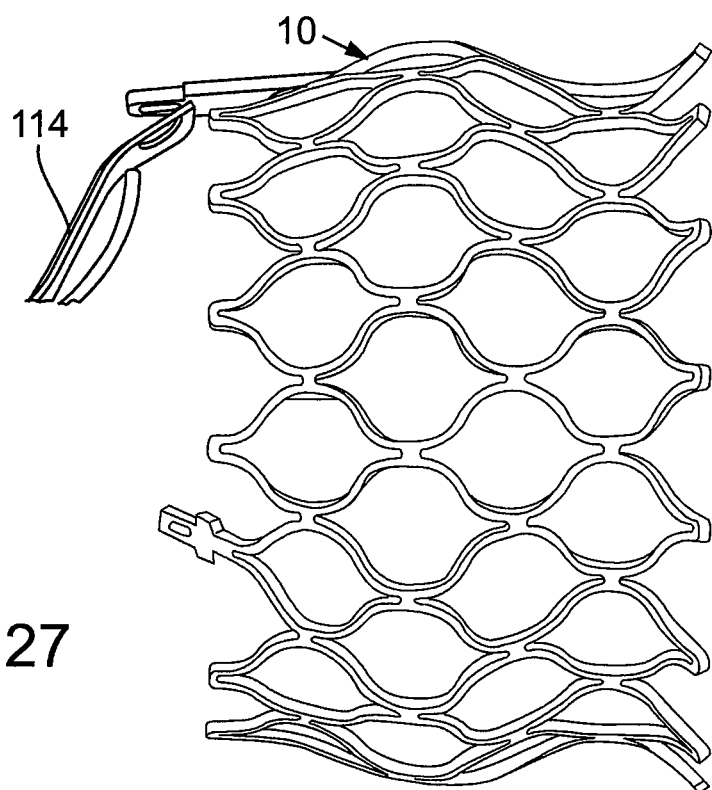
Figure 28:
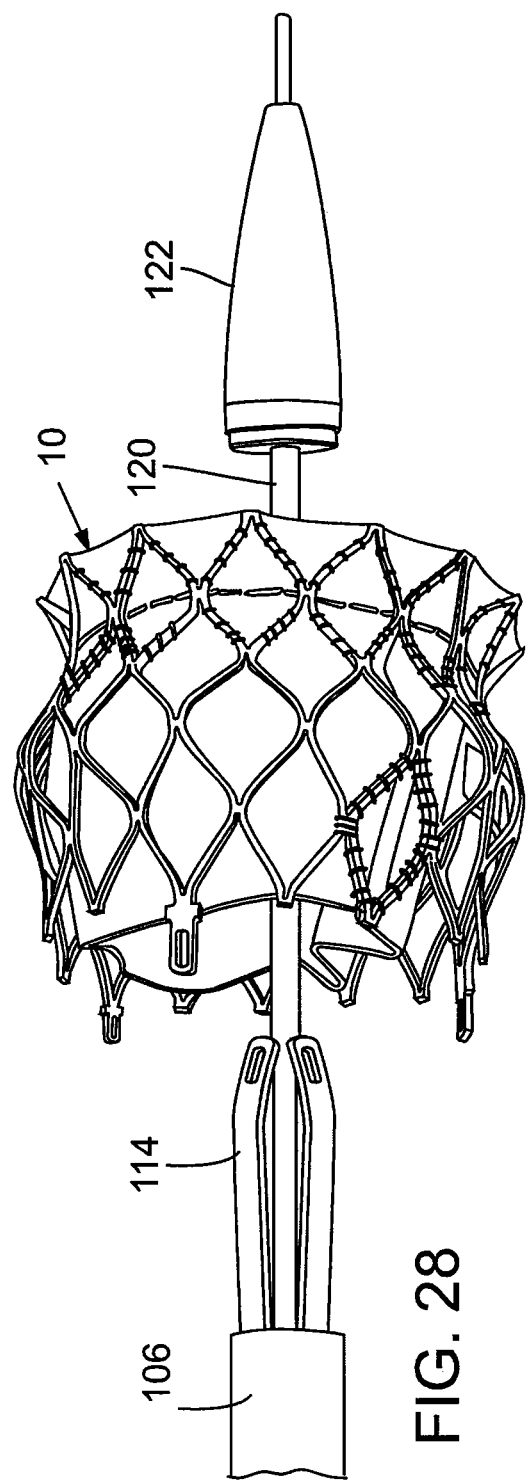
FIG. 28 shows the retaining mechanism being retracted into the sheath after the valve is released and deployed in the body.

After the valve 10 is advanced from the delivery sheath and expands to its functional size (as shown in FIG. 10), the valve remains connected to the delivery apparatus via the retaining mechanism 114. Consequently, after the valve is advanced from the delivery sheath, the surgeon can reposition the valve relative to the desired implantation position in the native valve such as by moving the delivery apparatus in the proximal and distal directions or side to side, or rotating the delivery apparatus, which causes corresponding movement of the valve. The retaining mechanism 114 desirably provides a connection between the valve and the delivery apparatus that is secure and rigid enough to retain the position of the valve relative to the delivery apparatus against the flow of the blood as the position of the valve is adjusted relative to the desired implantation position in the native valve. Once the surgeon positions the valve at the desired implantation position in the native valve, the connection between the valve and the delivery apparatus can be released by retracting the valve catheter shaft 110 in the proximal direction relative to the guide catheter, which is effective to retract the inner fork 138 to withdraw its prongs 142 from the openings 32 in the retaining arms 30 of the valve (FIGS. 26 and 27). Retraction of the delivery apparatus retracts the outer fork 140 to completely disconnect the valve from the retaining mechanism 114 (FIG. 28). Thereafter, the delivery apparatus can be withdrawn from the body, leaving the valve implanted within the native valve (such as shown in FIGS. 5A and 5B)

In an alternative embodiment, the delivery apparatus can be adapted to deliver a balloon-expandable prosthetic valve. As described above, the retaining mechanism 114 can be used to secure the valve to the end of the delivery apparatus. Since the stent of the valve is not self-expanding, the sheath 106 can be optional. The retaining mechanism 114 enhances the pushability of the delivery apparatus and valve assembly through the introducer sheath.

Figure 29A:
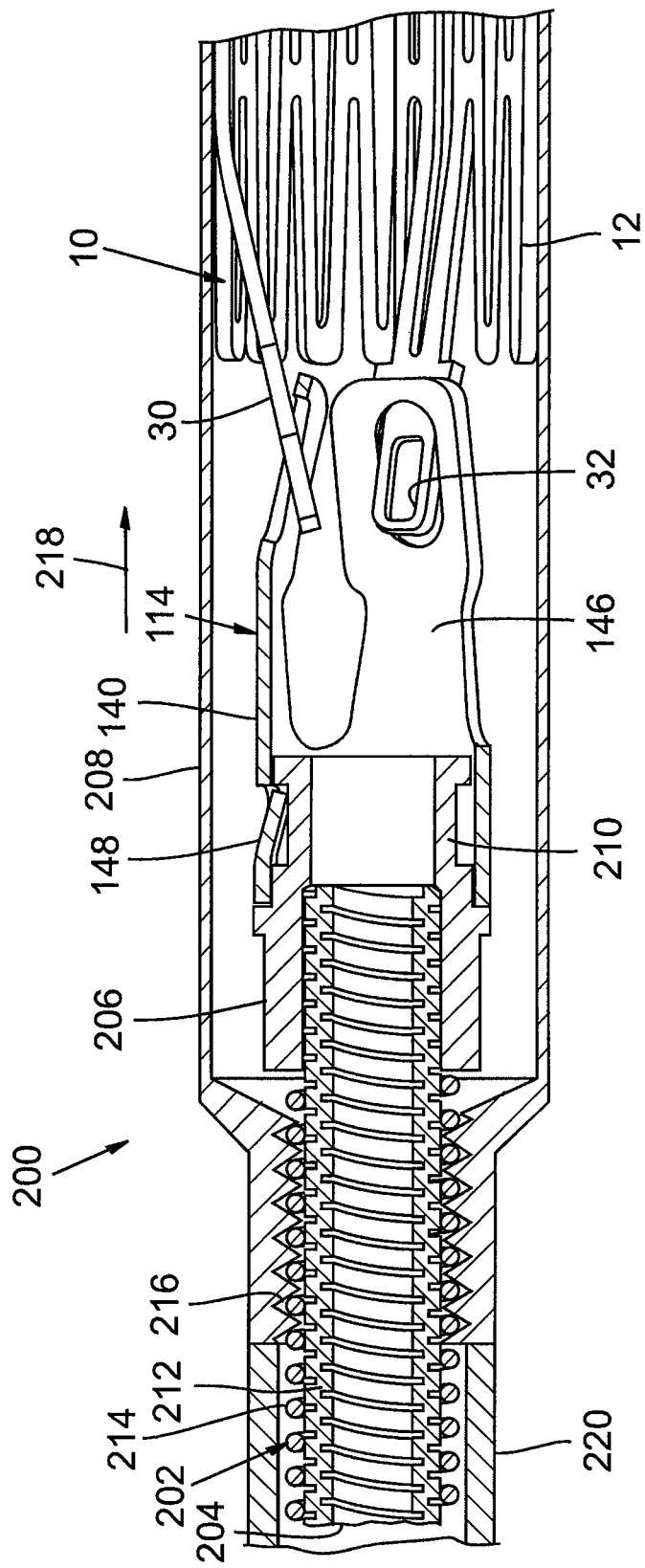
FIG. 29A is a cross-sectional view of the distal end portion of another embodiment of a delivery apparatus.

FIG. 29A shows the distal end portion of a delivery apparatus 200, according to another embodiment. The delivery apparatus 200 has a similar construction to and has many of the same components as the delivery apparatus 100 (some of the common components are removed from FIG. 29A for clarity). The delivery apparatus 200 comprises an elongated valve catheter 202. The valve catheter 202 comprises an elongated, flexible torque shaft 204, an end piece 206 secured to the distal end of the shaft 204, and an outer shaft 220 extending over the torque shaft 204.

A delivery sheath 208 is secured to the distal end of the outer shaft 220. The delivery sheath 208 is disposed over a distal end portion of the shaft 204, the end piece 206, a valve-retaining mechanism 114, and a valve 10, which is retained in a compressed state inside the sheath. Only the outer fork 140 of the retaining mechanism 114 is shown in FIG. 29A. The head portion 148 of the outer fork 140 can be secured to the end piece 206, such as by forming a snap-fit connection with a stepped shaft portion 210 of the end piece such as described above. The inner fork 138 (not shown in FIG. 29A) can be connected at its head portion 144 to the distal end of an inner shaft (not shown in FIG. 29A) that extends through the valve-catheter shaft. The inner shaft can be the shaft 120 of an elongated nose catheter 118 (FIG. 8). The prongs 142 of the inner fork 138 extend through the openings 32 in the stent 12 to secure the valve 10 to the delivery apparatus, as described in detail above. Because the inner fork 138 is secured to an inner shaft that extends through shaft 204, the inner fork 138 can be retracted relative to the outer fork 140 to withdraw the prongs of the inner fork from the openings in the stent (and thereby releasing the valve 10) by retracting the inner shaft in the proximal direction relative to the shaft 204.

The shaft 204 in the illustrated configuration comprises a first layer 212 comprising a flexible, slotted tube and second layer 214 comprising a wire coil that is helically wound around the first layer 212. The first layer 212 can be made of a metal (e.g., stainless steel), a polymeric material, or another suitable material. The wire coil 214 can be, for example, a stainless steel wire, although other materials can be used. The wire coil 214 extends along at least a distal end portion of the shaft 204 and engages internal threads 216 of the sheath 208. In this manner, the wire coil 214 serves as external threads of the shaft 204. When rotating the torque shaft 204 relative to the outer shaft 220, the sheath 208 is retained against rotating with the shaft 204 by the outer shaft 220 so that rotation of the shaft 204 causes the shaft 204 to advance distally relative to the sheath 208 to deploy the valve 10.

In use, the delivery apparatus 200 is inserted into the patient's vasculature and advanced to the implantation site in the heart. The torque shaft 204 is then rotated relative to the outer shaft 220 to cause the shaft to advance distally (as indicated by arrow 218) until the valve 10 is unsheathed and expands to its functional size. At this point, the valve 10 remains connected to the delivery apparatus by the retaining mechanism 114 so that the user can fine-tune the position of the expanded valve at the implantation site. Once the valve is in the desired orientation, the connection formed by the retaining mechanism 114 can be released by retracting the inner shaft, as described above. Thereafter, the retaining mechanism can be retracted back into the sheath and the entire delivery apparatus can be removed from the body.

Figure 29B:
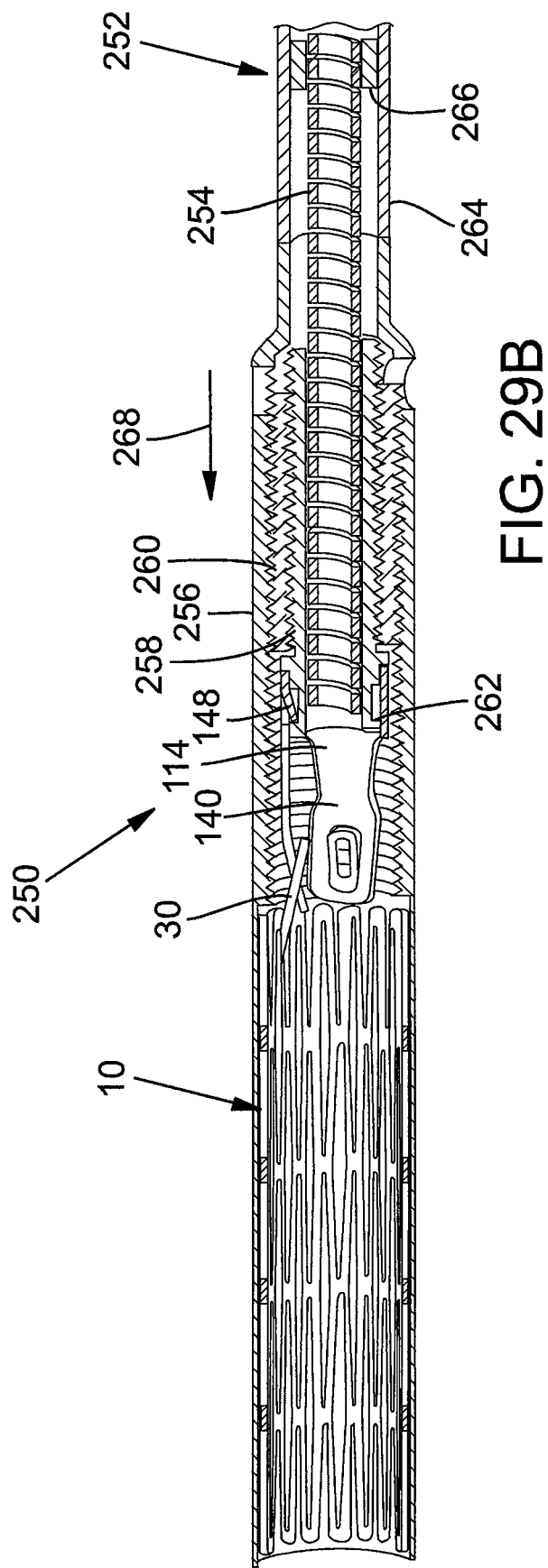
FIG. 29B is a cross-sectional view of the distal end portion of another embodiment of a delivery apparatus.

FIG. 29B shows the distal end portion of a delivery apparatus 250, according to another embodiment. The delivery apparatus 250 has a similar construction to and has many of the same components as the delivery apparatus 100 (some of the common components are removed from FIG. 29B for clarity). The delivery apparatus 250 comprises an elongated valve catheter 252 comprising an elongated, flexible torque shaft 254 that extends into a delivery sheath 256. The shaft 254 can comprise, for example, a coiled shaft as shown or a cable (e.g., a stainless steel cable). A first screw member 258 is disposed on and secured to a distal end portion of the shaft 254 within the sheath and a second screw member 260 is disposed on the first screw member within the sheath. The first screw member 258 has external threads that engage internal threads of the second screw member 260. The second screw member 260 also has external threads that engage internal threads of the sheath 256.

The delivery apparatus can further include an outer shaft 264 that extends over the shaft 254 and has a distal end portion that is secured to the proximal end of the sheath 256. The torque shaft 254 can be rotated relative to the outer shaft 264 and the sheath 256 to cause the torque shaft to advance longitudinally relative to the sheath for deploying the valve from the sheath. A ring member 266 is mounted on the outer surface of the torque shaft 254 and moves longitudinally with the torque shaft relative to the outer shaft 264 upon rotation of the torque shaft. The ring member 266 is positioned to contact and cause the second screw member 260 to advance within the sheath 256 after the torque shaft 254 is advanced distally a predetermined distance, as further described below.

As further shown in FIG. 29B, the outer fork 140 of a valve-retaining mechanism 114 can be secured at its head portion 148 to a stepped shaft portion 262 of the first screw member 258, which in turn is secured to the torque shaft 254. The inner fork 138 (not shown in FIG. 29B) can be connected at its head portion to the distal end of an inner shaft (not shown) that extends through the torque shaft 254. The prongs of the inner fork extend from the distal end of the shaft 254 and cooperate with the prongs of the outer fork to form releasable connections with the posts 30 of the stent, as described above. The inner fork can be retracted relative to the outer fork to release the connections to the posts 30 by retracting the inner shaft relative to the torque shaft 254.

In use, the delivery apparatus 250 is inserted into the patient's vasculature and advanced to the implantation site in the heart. To begin deployment of the valve, the torque shaft 254 is rotated relative to the outer shaft 264, which causes the first screw member 258 to rotate and advance distally (in the direction of arrow 268) relative to the second screw member 260 and the sheath 258 to partially advance the valve 10 from the distal end of the sheath. After the torque shaft 254 is advanced a predetermined distance, the ring member 266 contacts the second screw member 260 so that further rotation of the torque shaft 254 is effective to cause the first screw member and the second screw member to advance distally relative to the sheath to completely advance the valve 10 from the sheath. Once the valve is in the desired orientation, the connection formed by the retaining mechanism 114 can be released by retracting the inner shaft, as described above. Thereafter, the retaining mechanism can be retracted back into the sheath and the entire delivery apparatus can be removed from the body.

Figure 36:
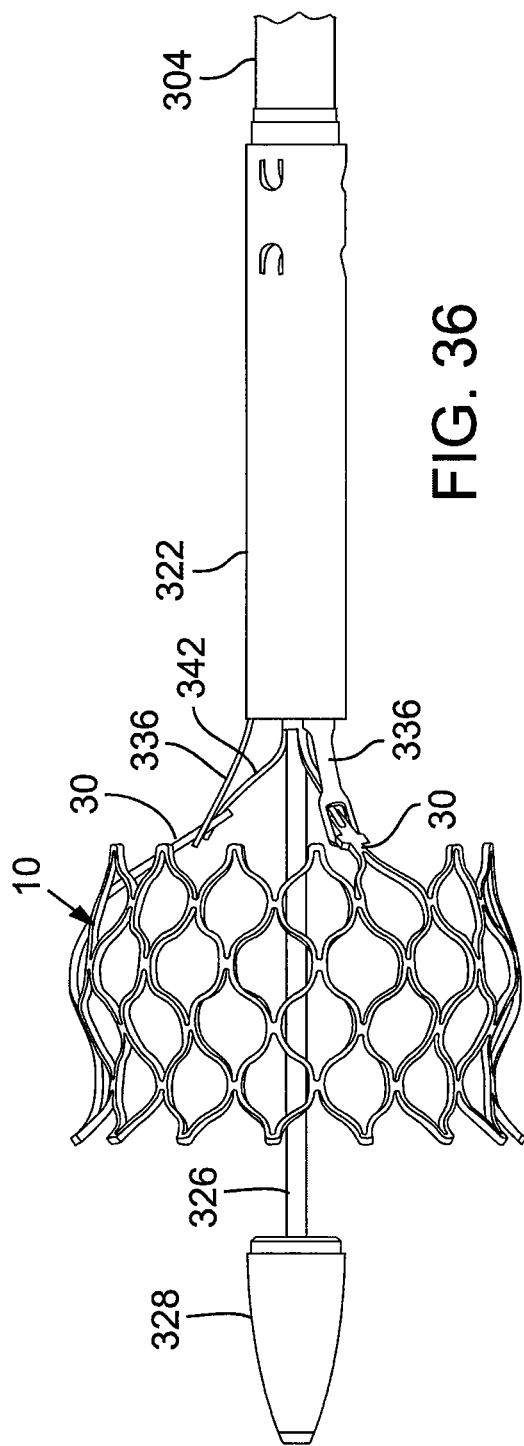
FIG. 36 is a side view illustrating the deployment of a valve from the sheath of the delivery apparatus of FIG. 30.
Figure 37:
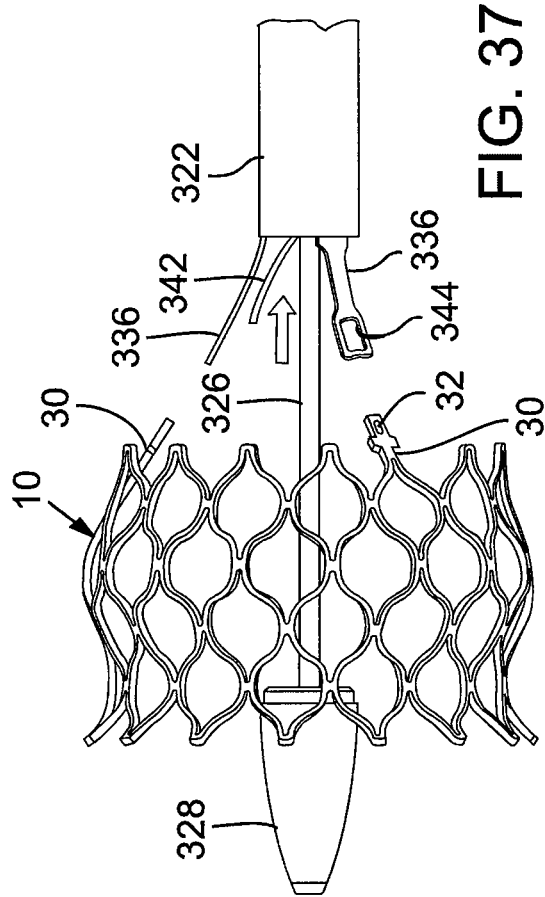
FIG. 37 is a side view illustrating the operation of the retaining mechanism of the delivery apparatus of FIG. 30.

FIGS. 30-37 illustrate a delivery apparatus 300, according to another embodiment. FIGS. 30-33 show the distal end portion of the delivery apparatus 300. FIGS. 34-35 show the proximal end portion of the delivery apparatus 300. FIGS. 36-37 show the deployment of a valve 10 from the delivery apparatus 300 (the leaflets of the valve are removed for clarify in the figures).

The delivery apparatus 300 comprises a first, outer catheter 302 having an elongated shaft 304 extending between a valve retaining mechanism 306 at the distal end of the apparatus (FIGS. 32 and 33) and a handle portion 308 at the proximal end of the apparatus (FIGS. 34 and 35). The distal end of the main catheter shaft 304 is coupled to the valve-retaining mechanism 306, which in turn is secured to the valve 10. The outer catheter 302 can be a guide catheter that is configured to permit selective bending or flexing of a portion of the shaft 304 to facilitate advancement of the delivery apparatus through the patient's vasculature.

The delivery apparatus also includes a second, torque catheter 310 having an elongated torque shaft 312 that extends through the main catheter shaft 304. The distal end of the torque shaft 304 is connected to a flexible screw mechanism 314 comprising a flexible shaft 316 extending through the retaining mechanism 306 and one or more screw members 318 spaced along the length of the shaft 316 (FIGS. 32 and 33). As shown in FIG. 33, the shaft 316 of the screw mechanism 314 exhibits sufficient flexibility to permit bending or flexing to assist in tracking the delivery apparatus through the patient's vasculature. The main catheter shaft 304 can be formed with internal threads that engage the external threads of the screw members 318. For example, a distal end portion of the main shaft 304 (e.g., an 11-mm segment at the distal end of the shaft 304) can be formed with internal threads. The proximal end portion of the torque shaft 312 extends into the handle portion 308 where it is coupled to a control knob 320 to permit rotation of the torque shaft relative to the main catheter shaft 304 (FIGS. 34 and 35), as further described below.

In operation, each screw member 318 passes through and engages the internally threaded portion of the main shaft 304. The screw members 318 desirably are spaced from each other such that a screw member 318 can engage one end of the internally threaded portion of the main shaft 304 before an adjacent screw member 318 disengages from the other end of the internally threaded portion of the main shaft as the screw members pass through the internally threaded portion so as to prevent or at least minimize application of axially directed forces on the torque shaft. In this manner, relatively high unsheathing forces can be applied to the sheath without compromising the overall flexibility of the delivery apparatus.

The delivery apparatus can also include a third, nose catheter 324 having an elongated shaft 326 that is connected at its distal end to a nose piece 328. The nose catheter shaft 326 extends through the torque shaft 312 and has a proximal end portion that extends outwardly from the proximal end of the handle portion 308 (FIGS. 34 and 35). The main catheter shaft 304, the torque shaft 312, and the nose catheter shaft 326 desirably are configured to be movable axially relative to each other.

As shown in FIGS. 30 and 31, the delivery apparatus can further include a movable sheath 322 that extends over the compressed valve 10. The sheath 322 is connected to screw mechanism 314 so that longitudinal movement of the torque shaft 312 and the screw mechanism 314 causes corresponding longitudinal movement of the sheath 322. For example, the sheath can have inwardly extending prongs 358 (FIG. 31) extending into respective apertures 360 of fingers 362 (FIG. 32), which in turn are connected to the distal end of the flexible shaft 316. Fingers 362 desirably are connected to the shaft 316 by a swivel joint that pushes or pulls fingers 362 when the shaft 316 moves distally or proximally, respectively, yet allows the shaft 316 to rotate relative to the fingers 362. Consequently, rotation of the torque shaft 312 and the screw mechanism 314 relative to the main shaft 304 is effective to cause the sheath 322 to move in the proximal and distal directions (as indicated by double-headed arrow 330 in FIG. 30) relative to the valve to permit controlled deployment of the valve from the sheath, as further described below.

Referring to FIGS. 32 and 33, the valve-retaining mechanism 306 comprises an outer fork 330 and an inner fork 332. A portion of the finger 362 is cut away in FIG. 33 to show the inner fork 332. The outer fork 330 comprises a head portion 334 and a plurality of elongated, flexible prongs 336 (three in the illustrated embodiment) extending from the head portion 334. The head portion 334 can be formed with resilient retaining flanges 338 to permit the outer fork to form a snap-fit connection with a stepped shaft portion of the main catheter shaft 304, as described above. The inner fork 332 has a head portion 340 that is fixedly secured to the nose catheter shaft 326 and a plurality of elongated prongs 342 extending from the head portion 340. The distal end portions of the prongs 336 of the outer fork can be formed with apertures 344 sized to receive respective retaining arms 30 of the valve 10. The distal ends of the prongs 342 of the inner fork 332 extend through the apertures 32 in the retaining arms 30 to form a releasable connection for securing the valve 10, similar to valve-retaining mechanism 114 described above and shown in FIGS. 14-16. After the valve is deployed form the sheath 322, the connection between the valve and the retaining mechanism 306 can be released by retracting the nose catheter shaft 326 relative to the main catheter shaft 304 to withdrawn the prongs 342 from the apertures 32 in the retaining arms 30. The outer prongs 336 and the shaft 316 of the screw mechanism 314 exhibit sufficient flexibility to allow that portion of the delivery apparatus to bend or flex as the delivery apparatus is advanced through the patient's vasculature to the implantation site, yet are rigid enough to permit repositioning of the valve after it is deployed from the sheath 322. The outer fork 330, including prongs 336, can be made from any of various suitable materials, such as metals (e.g., stainless steel) or polymers, that provide the desired flexibility.

Referring to FIGS. 34 and 35, the handle portion 308 comprises a housing 346 that houses a first gear 348 and a second gear 350. The first gear 348 has a shaft that extends through the housing and is connected to the control knob 320 located on the outside of the housing. The second gear 350 is disposed on and fixedly secured to the torque shaft 312. Thus, manual rotation of the control knob 320 causes rotation of the first gear 348, which in turn rotates the second gear 350. The second gear 350 rotates the torque shaft 312 and the screw mechanism 314 relative to the main catheter shaft 304, the valve-retaining mechanism 306, and the valve 10. Rotation of the torque shaft 312 and the screw mechanism 314 in turn causes linear movement of the sheath 322 relative to the valve.

In use, the valve 10 is loaded into the sheath 322 in a radially compressed state (as depicted in FIG. 30), which can be accomplished, for example, by using the loading cone 124 described above. The delivery apparatus 300 is then inserted into the patient's vasculature and advanced to a position at or adjacent the implantation site. The valve 10 can then be deployed from the sheath by rotating the knob 320 on the handle portion, which in turn causes the torque shaft 312 and the screw mechanism 316 to retract within the main shaft 304, causing the sheath 322 to move in the proximal direction (arrow 352 in FIG. 31) to expose the valve, as depicted in FIG. 31. Rotation of the knob 320 enables a controlled and precise retraction of the sheath 322 during valve deployment. Advantageously, the sheath is retracted while the position of the valve can be held constant relative to the annulus at the implantation site during the unsheathing process. Rotation of the knob in the opposite direction causes the sheath to move in the distal direction to again cover the valve. Thus, after the valve has been at least partially advanced from the sheath, it is possible to reverse rotation of the knob to bring the valve back into the sheath in a compressed state if it becomes necessary to reposition the delivery apparatus within the body or to completely withdraw the delivery apparatus and the valve from the body.

After the valve 10 is advanced from the delivery sheath and expands to its functional size (as shown in FIG. 36), the valve remains connected to the delivery apparatus via the retaining mechanism 306. Consequently, after the valve is advanced from the delivery sheath, the surgeon can reposition the valve relative to the desired implantation position in the native valve such as by moving the delivery apparatus in the proximal and distal directions or side to side, or rotating the delivery apparatus, which causes corresponding movement of the valve. The retaining mechanism 306 desirably provides a connection between the valve and the delivery apparatus that is secure and rigid enough to retain the position of the valve relative to the delivery apparatus against the flow of the blood as the position of the valve is adjusted relative to the desired implantation position in the native valve. Once the surgeon positions the valve at the desired implantation position in the native valve, the surgeon can release the connection between the valve and the delivery apparatus by pulling the proximal end 354 of the nose catheter shaft 326 in the proximal direction (as indicated by arrow 356 in FIG. 34) relative to the main catheter shaft 304, which is effective to retract the inner fork 332 to withdraw its prongs 342 from the openings 32 in the retaining arms 30 of the valve (FIG. 37). Retraction of the main catheter shaft 304 retracts the outer fork 330 to completely disconnect the valve from the retaining mechanism 306 (as shown in FIG. 37). Thereafter, the retaining mechanism can be retraced back into the sheath 322, the delivery apparatus can be withdrawn from the body, leaving the valve implanted within the native valve (such as shown in FIGS. 5A and 5B).

Figure 38A:
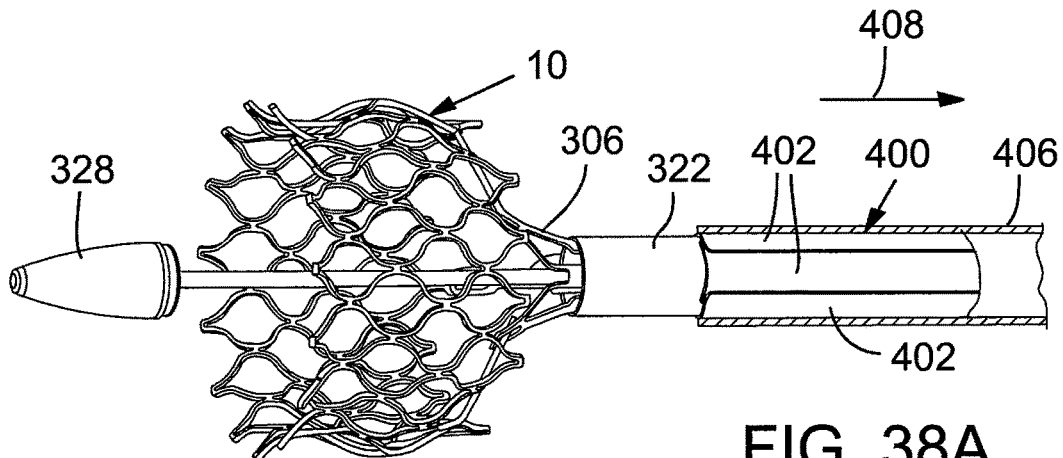
FIGS. 38A-38C illustrate the operation of a valve-retrieval device being used to retrieve an expanded valve back into a delivery apparatus for removal from the body.
Figure 38B:
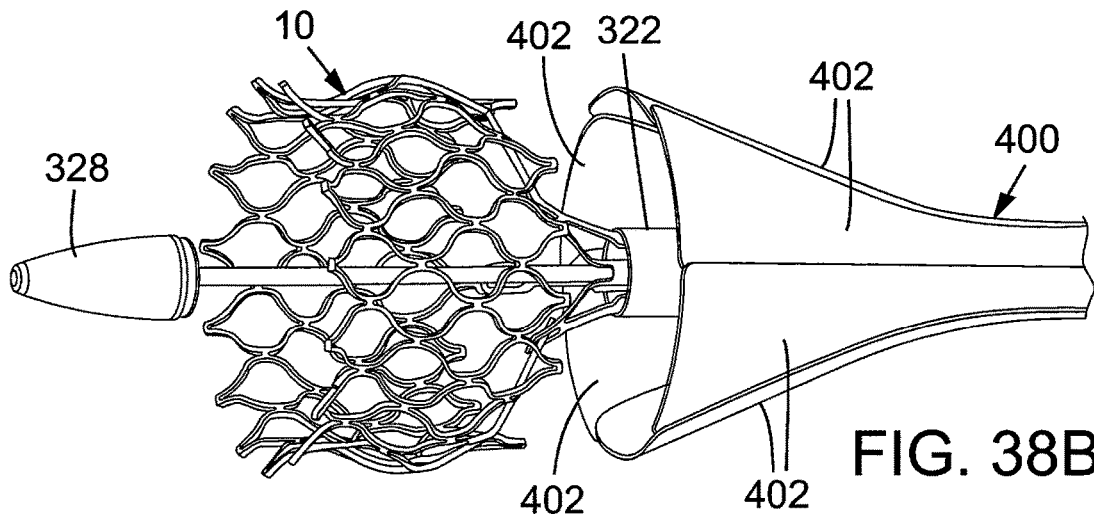
Figure 38C:
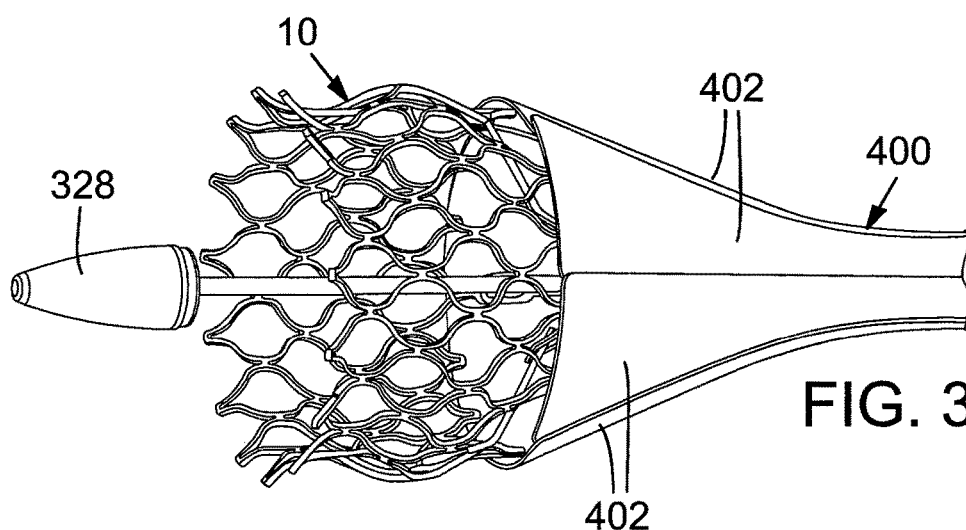

If the surgeon decides to abort the procedure after the valve 10 is fully deployed from the sheath but still connected to the retaining mechanism 306, it may not be possible to retrieve the expanded valve back into the sheath. To such ends, FIGS. 38A-38C show an embodiment of a valve-retrieving device 400 that can be used with the delivery apparatus 300 to assist in retrieving the expanded valve 10 back into the sheath 322. The valve-retrieving device 400 in the illustrated embodiment comprises an elongated, generally cylindrical body that is configured to be inserted into the patient's vasculature and advanced over the main catheter shaft 304. The distal end portion of the body comprises a plurality of elongated, flexible flap portions 402 that are normally retained in a compressed state, generally in the form of a cylinder (as shown in FIG. 38A) and can flex radially outward from each other to form a generally cone-shaped receptacle large enough to receive the proximal end of the expanded valve 10 (FIGS. 38B and 38C). The flap portions 402 desirably are prevented from expanding beyond the expanded state shown in FIGS. 38B and 38C. In addition, the flap portions 402 desirably are dimensioned to overlap each other in the circumferential direction so that when the flap portions expand, they form a cone having continuous outer surface without any gaps between the flap portions. To effect expansion of the flap portions 402, each flap portion can be connected to a respective pull wire that extends along the length of the retrieving device 400 to a proximal end thereof. When tension is applied to the proximal ends of the pull wires, the flap portions are caused to flex radially outward from each other. In addition, the flap portions 402 can be made from a mesh material or perforated material, such as perforated foil to allow blood to flow through the flap portions during the retrieving process.

Alternatively, the flap portions 402 can be made from a shape-memory material, such as Nitinol, and are self-expanding. The self-expanding flap portions normally assume the expanded configuration shown in FIGS. 38A-38B. The flap portions 402 can be held in the radially compressed state by an outer sheath 406 (FIG. 38A). When the sheath 406 is retracted relative to the flap portions 402 in the direction of arrow 408, the flap portions 402 expand to the expanded configuration shown in FIGS. 38A-38B.

As noted above, the retrieving device 400 can be used to retrieve a fully expanded valve and remove it from the patient's body. In use, the retrieving device 400 is inserted into the body over the main catheter shaft 304 and advanced toward the deployed valve 10, as shown in FIG. 38A. As shown in FIGS. 38B and 38C, the flap portions 402 are then expanded and further advanced in the distal direction to engage the valve. As the retrieving device advances over the valve, the valve is caused to compress. When the valve is compressed to a diameter small enough to permit reinsertion into the sheath 322, the sheath 322 is advanced in the distal direction (e.g., by rotation of knob 320) until the sheath extends over the valve. Once the valve is inside the sheath, the retrieving device can be removed from the patient's body, followed by the delivery apparatus and the valve.

In certain embodiments, a portion of the elongated body of the retrieving device 400 can have internal threads that are adapted to engage the threads of screw members 318 (FIG.

32) so that the retrieving device can be moved in the distal and proximal directions by rotation of the knob 320 (FIG. 34). In use, the retrieving device is inserted into the body and advanced over the main catheter shaft 304 until the threaded portion of the retrieving device engages the screw members 318. The flap portions 402 are then expanded and the retrieving device and the sheath are advanced over the expanded valve by rotation of the knob 320. The distal ends of flap portions 402 extend past the distal end of the sheath 322 so that as both are advanced, the proximal end of the valve first comes in contact with the flap portions and begins to compress to facilitate insertion of the valve into the sheath.

FIG. 39 illustrates a modification of the delivery apparatus 300. In this embodiment, the valve 10 is held in its compressed state after deployment from the sheath 322 by a restraining device, such as one or more releasable bands 370 that encircle the valve. The bands 370 can be released by pulling or moving a snare device, which allow the bands to open and the valve to expand. Alternatively, the bands 370 can be made of a bio-absorbable or soluble material that dissolves in the body after the valve is advanced to the implantation site. Because the valve is held in its compressed state while it is advanced from the sheath, the problem of the valve "jumping" from the end of the sheath can be avoided to allow a more controlled delivery of the valve. If the bands 370 or similar restraining devices are used, the delivery apparatus can employ a conventional pusher shaft that is operable to push the valve through the sheath, and need not include a rotatable torque shaft that is rotated to effect deployment of the valve from the sheath. In other words, the bands 370 or similar restraining devices can be used with a conventional delivery apparatus where the operator pushes a shaft to push the valve from the sheath. Furthermore, in some embodiments, the delivery apparatus need not include a sheath that covers the compressed valve during delivery due to the fact that the restraining device can retain the valve in its compressed state as it is advanced through the patient's vasculature to the implantation site.

Figure 40:
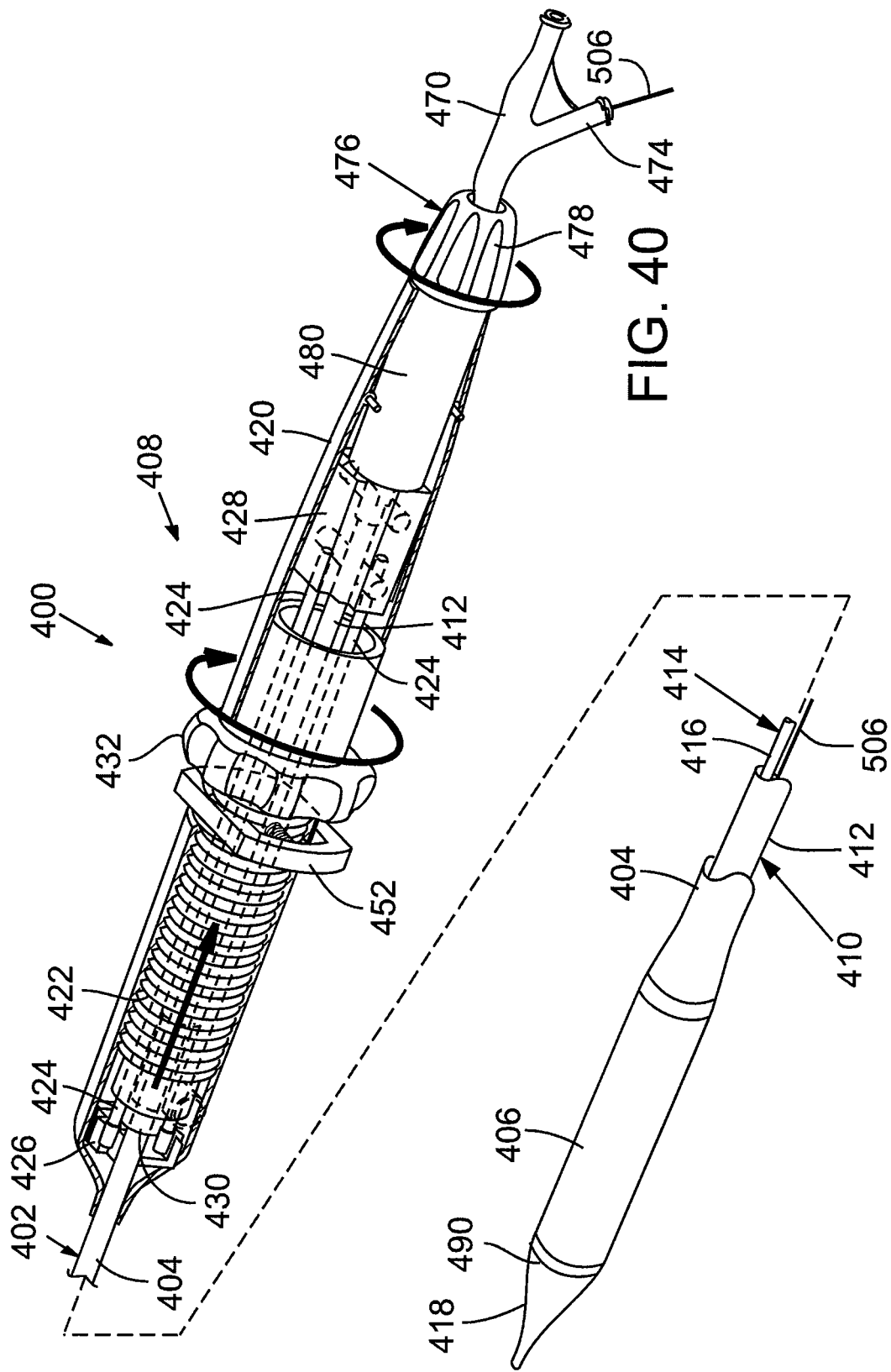
FIG. 40 is a perspective view of another embodiment of a delivery apparatus.

FIG. 40 illustrates a delivery apparatus 400, according to another embodiment. The delivery apparatus 400 includes a first, outermost or main catheter 402 having an elongated shaft 404, the distal end of which is coupled to a delivery sheath 406 that sized to extend over and retain a prosthetic valve 10 in a compressed state during valve delivery. The proximal end of the shaft 404 is connected to a handle assembly 408 of the delivery apparatus. The delivery apparatus also includes a second catheter 410 (also referred to as a valve catheter) having an elongated shaft 412 extending through the shaft 404. The delivery apparatus can also include a third, nose catheter 414 having an elongated shaft 416 and a nose piece 418 secured to the distal end portion of the shaft 416. The nose catheter shaft 416 extends through the valve catheter shaft 412 and can include a lumen for receiving a guidewire. The shafts 404, 412, and 416 desirably are configured to be movable axially relative to each other in the distal and proximal directions.

Figure 46:
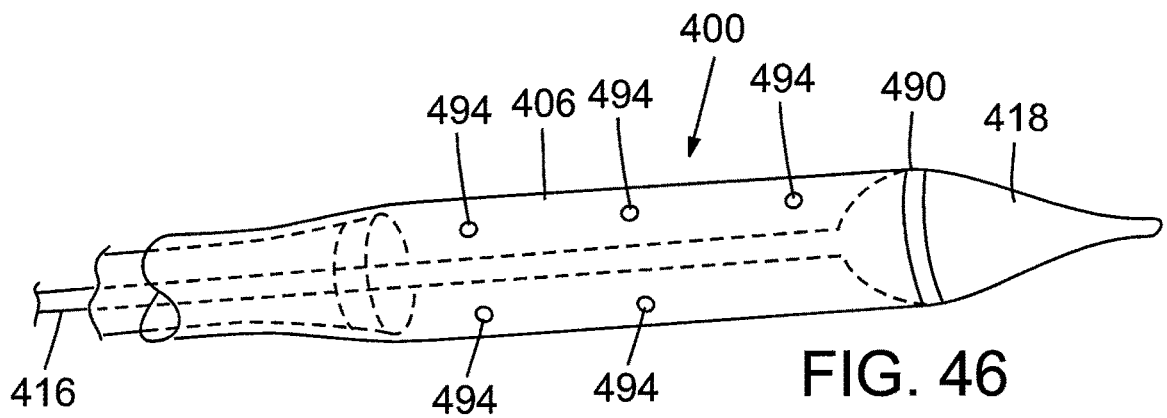
FIG. 46 is an enlarged, perspective view of the distal end portion of the delivery apparatus shown in FIG. 40.

As best shown in FIG. 46, the nose piece 418 can have a tapered distal end portion for atraumatic tracking of the delivery apparatus through the patient's vasculature as well as a tapered proximal end portion that extends into the sheath 406. After the valve is deployed, the tapered proximal end portion of the nose piece allows the nose piece to be more easily inserted back into the sheath 406 for withdrawing the delivery apparatus from the body. The sheath 406 can include a radiopaque tip portion 490 to assist the operator in retracting the nose piece back into the sheath.

Figure 48:
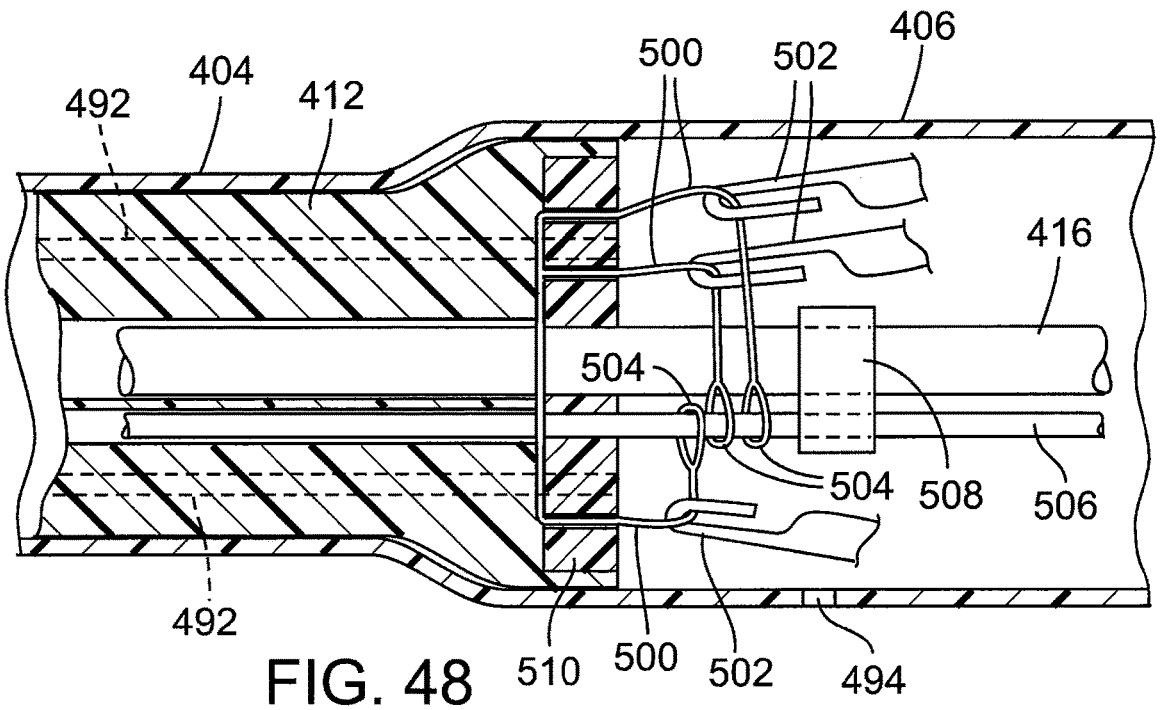
FIG. 48 is an enlarged, cross-sectional view of the distal end portion of the delivery apparatus of FIG. 40 illustrating a technique for forming a releasable connection between a prosthetic valve and the delivery apparatus.

As best shown in FIG. 48, the valve catheter shaft 412 can have one or more lumens 492 for introducing a contrast media, such as a radiographic contrast liquid, into the sheath 406 within the space surrounding the valve. The sheath 406 can have one or more apertures 494 (FIGS. 46 and 48) for injecting the contrast media into the patient's vasculature. The handle assembly 408 can have a separate an inlet port in fluid communication with the lumens 492 for introducing the contrast media into the lumens. The contrast media can be injected into the patient's vasculature adjacent the native valve prior to deploying the prosthetic valve to assist in identifying the desired location for implanting the prosthetic valve. For example, when replacing the aortic valve, the contrast media can be injected into the aorta immediately adjacent the base of the native leaflets. This provides visual feedback to the operator to help identify the desired location for deploying the prosthetic valve. After the prosthetic valve is implanted, additional contrast media can be injected immediately adjacent the leaflets of the prosthetic valve to provide visual feedback of the operation of the prosthetic valve.

In particular embodiments, the inner diameter of the sheath 406 is about 0.265 inch or less and the outer diameter of the sheath is about 0.28 inch or less.

Figure 41:
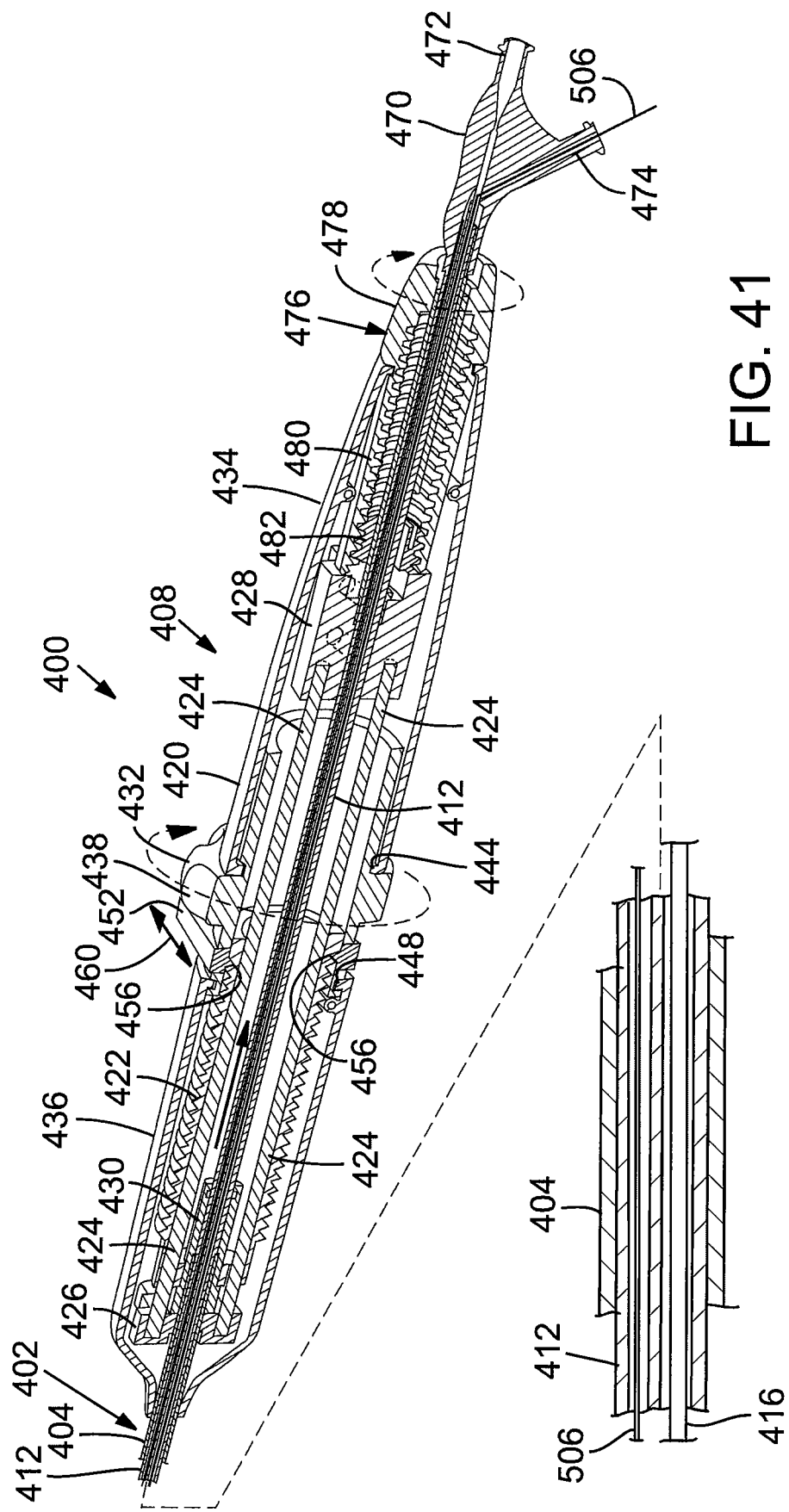
FIG. 41 is an enlarged, cross-sectional view of the handle assembly of the delivery apparatus of FIG. 40.

Referring to FIG. 41, the handle assembly in the illustrated configuration includes a housing 420 that houses the proximal end portions of shafts 404, 412, and 416 and a screw shaft 422. The screw shaft 422 is mounted for longitudinal movement inside the housing 420 on elongated support rods 424. The distal ends of the support rods 424 can be supported by a distal bracket 426 and the proximal ends of the support rods can be supported by a proximal bracket 428. The proximal end of the main shaft 404 can be secured to a stub shaft 430, which in turn can be secured, such as by bonding, to the inside of the screw shaft 422. The screw shaft 422 is operatively connected to an actuator, or control knob, 432, which is operable to control longitudinal movement of the screw shaft 422 and the main shaft 404 upon rotation of the knob, as further described below. The handle assembly 408 can further include a connector 470 mounted at its proximal end. The connector 470 has a first passageway 472 that is in fluid communication with the lumen of the nose catheter shaft 416 for insertion of a guide wire through the shaft 416. The connector 470 can have a second passageway 474 through which the proximal end portion of a release wire 506 extends (described below).

Figure 42:
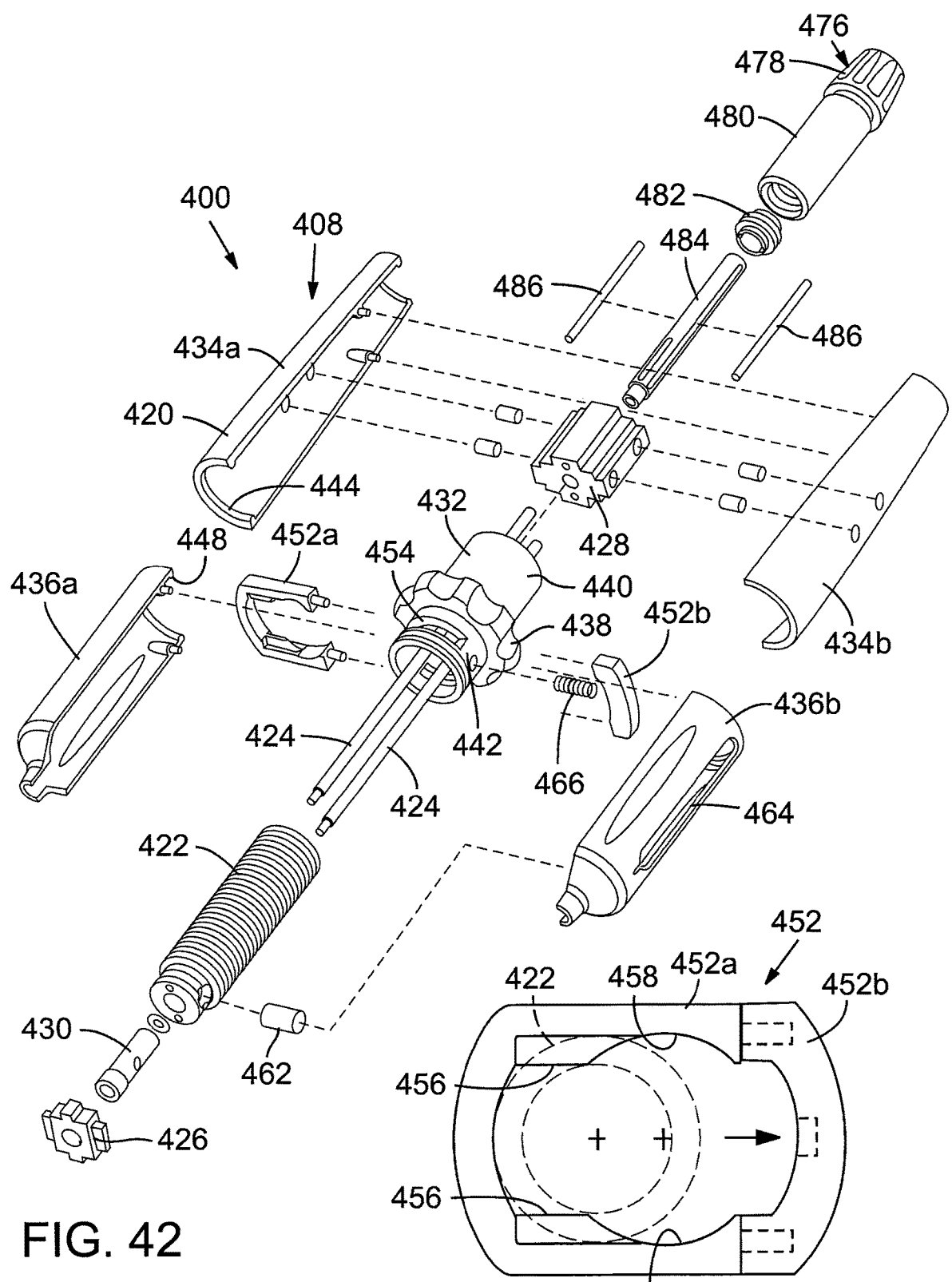
FIG. 42 is an exploded, perspective view of the handle assembly shown in FIG. 41.

As best shown in FIG. 42, the housing 420 of the handle assembly 408 can comprise a proximal housing portion 434 and a distal housing portion 436. The proximal housing portion 434 can comprise first and second housing portions 434a, 434b, and the distal housing portion 436 can comprises first and second housing portions 436a, 436b. The screw shaft 422 can include a flush port 462 that extends through a slot 464 in the second housing portion 436b. The flush portion 462 has a lumen that is in fluid communication with the space between the main shaft 404 and the valve catheter shaft 412 for introducing a flush fluid between the shafts.

Figure 44:
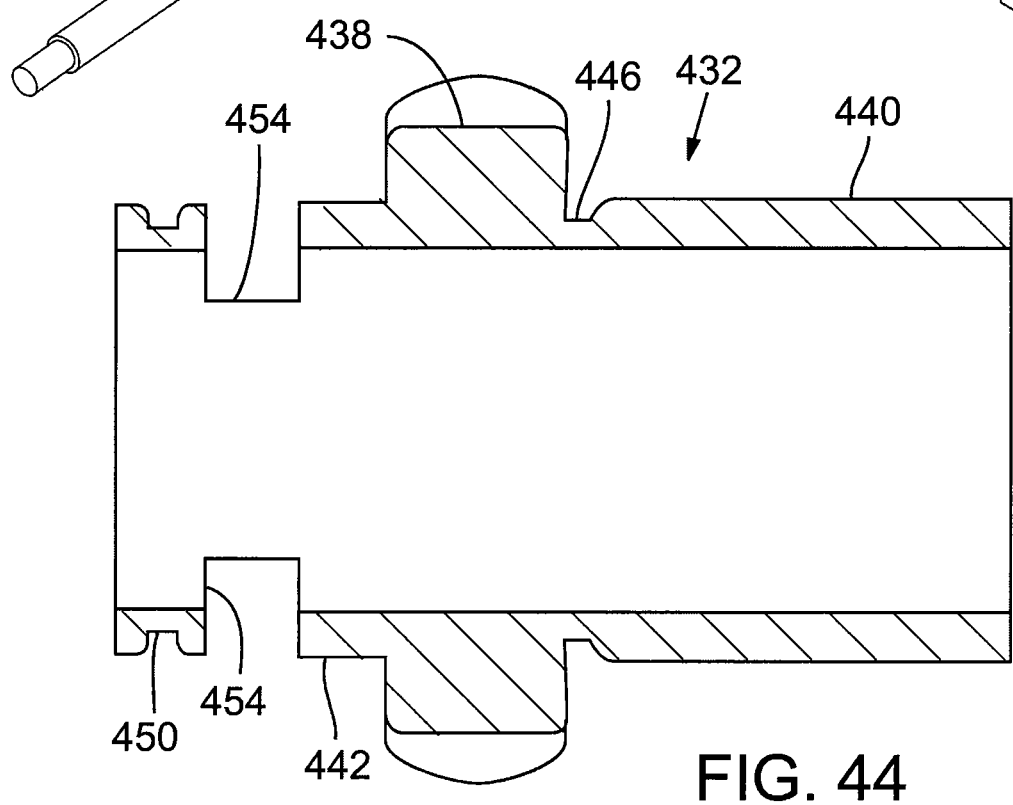
FIG. 44 is a cross-sectional view of the sheath adjustment knob shown in FIG. 43.

The control knob 432 can comprise a knob portion 438, a proximal extension 440 that extends into the proximal housing portion 434, and a distal extension 442 that extends into the distal housing portion 436. As best shown in FIG. 41, when the handle assembly is assembled, the knob portion 438 is mounted between the proximal and distal housing portions. The proximal housing portion 434 can be secured to the proximal extension 440 via an annular flange 444 of the proximal housing portion that extends into a corresponding annular groove 446 (FIG. 44) in the proximal extension 440. Similarly, the distal housing portion can be secured to the distal extension 442 via an annular flange 448 of the distal housing portion that extends into a corresponding annular groove 450 (FIG. 44) of the distal extension 442.

Figure 43:
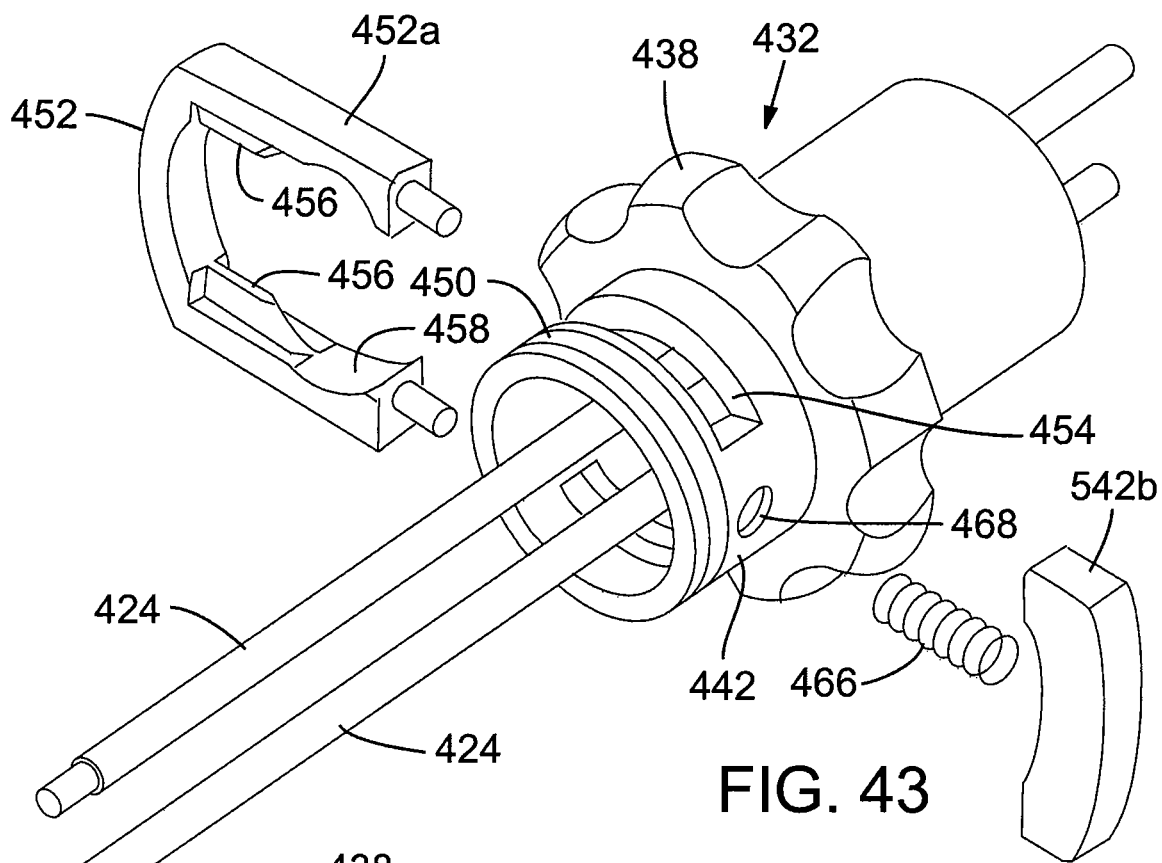
FIG. 43 is an enlarged, perspective view of the sheath adjustment knob of the handle assembly shown in FIG. 41.

The control knob 432 can include a screw engagement latch 452 mounted on the distal extension 442. The screw engagement latch 452 is operable to allow a user to selectively engage or disengage the screw shaft 422 for fine or course adjustment, respectively, of the main shaft 404. Explaining further, the screw engagement latch 452 (which can comprise first and second latch portions 452a, 452b) is mounted within upper and lower slots 454 formed in the distal extension 442 of the control knob. As best shown in FIG. 45, the latch 452 has upper and lower inwardly extending flanges 456 that extend through the slots 454 and can engage the external threads of the screw shaft 422. The latch 452 is also formed with arcuate upper and lower internal surfaces 458 adjacent the flanges 456. The latch 452 is slidable on the distal extension 442 in the lateral direction (as indicated by double headed arrow 460) between an engaged position wherein the flanges 456 extend through slots 454 and engage the screw shaft 422 and a disengaged position wherein the curved surfaces 458 are aligned within the slots 454 and the latch becomes disengaged from the screw shaft 422. A spring 466 can be disposed between the distal extension 442 and the latch portion 452b to retain the latch 452 in the engaged position against the bias of the spring. As best shown in FIG. 43, one end of the spring 466 can be retained in a notch 468 in the side of the distal extension 442 and the other end of the spring can be positioned to bear against the inside surface of the latch portion 452b.

When the latch is in the engaged position such that the flanges 456 engage the threads of the screw shaft 422, rotation of the control knob 432 causes the screw shaft 422 to move longitudinally within the housing 420. Since the main shaft 404 is secured to the screw shaft 422, longitudinal movement of the screw shaft causes corresponding longitudinal movement of the main shaft 404 and the sheath 406 relative to a valve mounted at the distal end of the valve catheter shaft 412. Rotation of the control knob 432 is effective to move the sheath 406 relative to the valve in a precise and controlled manner for controlled deployment of the valve. When the latch 452 is moved to the disengaged position such that the curved surfaces 458 are aligned in the slots 454, the latch 452 becomes disengaged from the screw shaft 422 due to the fact that the internal diameter defined by the surfaces 458 is greater than the external diameter of the screw shaft 422. In the disengaged position, the main shaft 404 can be pushed or pulled freely relative to the control knob 432 for course adjustment of the position of the sheath 406. The operator can adjust the position of the sheath 406 either by pushing or pulling on the portion of the main shaft 404 that extends from the housing 420 or by pushing or pulling on the flush port 462 (which moves within slot 464).

The valve catheter shaft 412 can comprise a guide catheter that is configured to allow a surgeon to guide or control the amount of bending or flexing of a distal portion of the delivery apparatus to facilitate guiding the delivery apparatus through the patient's vasculature. For example, referring to FIGS. 41 and 42, the handle assembly 408 can include an adjustment mechanism 476 that is operable to adjust the amount of bending or flexing of the distal end of the delivery apparatus. The adjustment mechanism 476 can include a rotatable adjustment knob 478 having a distal extension 480 that extends into the housing 420. The distal extension 480 has a bore formed with internal threads that engages a slide nut 482, which is supported for longitudinal movement on a central slide rod 484. Two support rods 486 extend between the inner surface of the slide nut 482 and the outer surface of the slide rod 484. Each support rod 486 is supported in an elongated notch in the outer surface of the slide rod 484 and the inner surface of the slide nut 482 so as to restrict rotation of the slide nut 482 relative to the adjustment knob 478. By virtue of this arrangement, rotation of the knob 478 (either clockwise or counterclockwise) causes the slide nut 482 to move longitudinally relative to the slide rod 484 in the distal and proximal directions. At least one pull wire (not shown) is secured at its proximal end to the slide nut 482, extends through the handle assembly and the shaft 412 and is secured at its distal end at a location adjacent the distal end of the shaft 412. To increase the curvature of the distal end portion of the delivery apparatus, the knob 478 is rotated to cause movement of the slide nut 482 in the proximal direction, which in turn pulls the pull wire to increase the curvature of the delivery apparatus. To decrease the curvature of the delivery apparatus, the adjustment knob 478 is rotated in the opposite direction to move the slide nut 482 in the distal direction, which decreases tension in the pull wire to allow the distal end portion of the delivery apparatus to straighten under its own resiliency. Further details of an adjustment mechanism for controlling the bending of a guide catheter are disclosed in U.S. Patent Publication Nos. 2008/0065011 and 2007/0005131, which are incorporated herein by reference.

Figure 47:
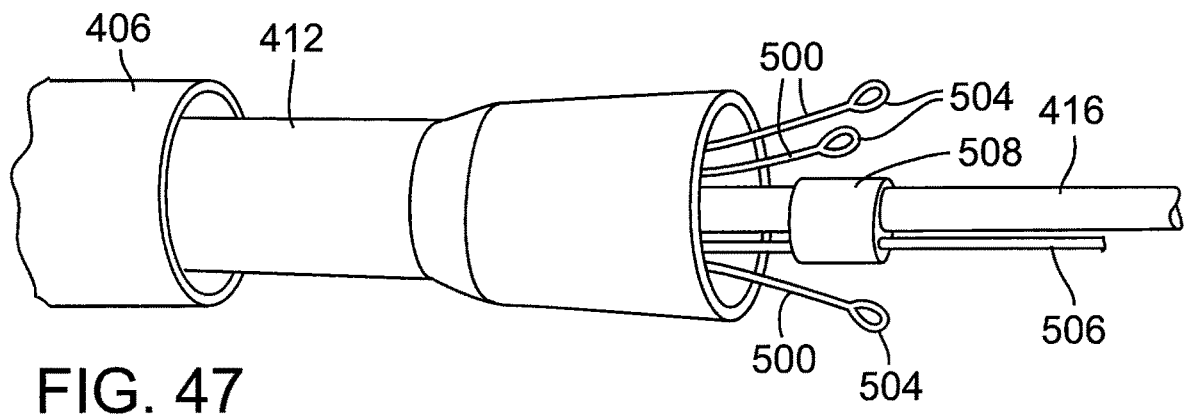
FIG. 47 is an enlarged, perspective view of the distal end portion of the delivery apparatus of FIG. 40 shown with the sheath retracted to illustrate sutures used to secure a prosthetic valve (not shown) to the delivery apparatus.
Figure 49:
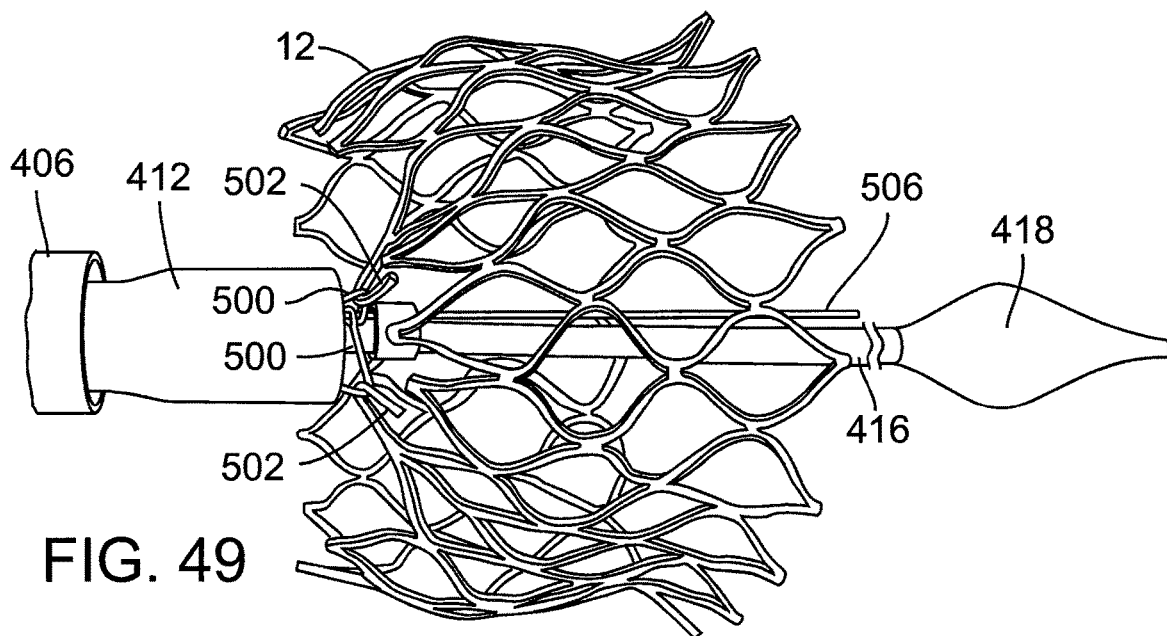
FIG. 49 is an enlarged, perspective view of the distal end portion of the delivery apparatus of FIG. 40 shown with the sheath retracted and the expanded valve secured to the delivery apparatus by the releasable connection.

Referring now to FIGS. 47-49, a prosthetic valve 10 can be secured to the distal end of the valve catheter shaft 412 via a releasable connection comprising a plurality of sutures 500 extending from the distal end of the valve catheter shaft 412. Each suture 500 extends through a hook portion 502 of the valve stent 12 (FIG. 49) and is formed with a loop 504 through which a release wire 506 extends. The release wire 506 can extend through a spacer 508 mounted on the nose catheter shaft 416 to maintain the release wire in parallel alignment with the nose catheter shaft. The release wire 506 further extends through the valve catheter shaft 412, the handle assembly 408, and the connector 470 (FIG. 41). As best shown in FIG. 48, the sutures 500 can extend through apertures in a tip portion 510 of the valve catheter shaft and are tied off to each other or otherwise secured to the tip portion 510 to secure the sutures 500 relative to the valve catheter shaft. It should be noted that the entire valve 10 is not shown; only the valve stent 12 is shown in FIG. 49 for purposes of illustration. The valve 10 can have a construction similar to that shown in FIGS. 1-2.

During valve delivery, the valve is mounted in a radially compressed state within the sheath 406. In order to deploy the valve from the sheath 406, the sheath is retracted relative to the valve, either by rotation of the control knob 432 (when the latch 452 is in the engaged position) or by pulling the main shaft 404 in the proximal direction (when the latch 452 is in the disengaged position). Retraction of the sheath 406 uncovers the valve, which expands to its functional size while remaining connected to the valve catheter shaft 412 via sutures 500, as shown in FIG. 49. Since the valve remains connected to the valve catheter shaft 406, the position of the expanded valve can be adjusted by moving the handle assembly 408 of the delivery apparatus. Once the valve is in its desired position for implantation, the valve can be released by retracting the release wire 506 to release the suture loops 504 from the release wire, thereby releasing the sutures 500 from the hook portions 502 of the valve. The release wire 506 can be retracted by pulling on the proximal end of the release wire that extends from the connector 470 on the handle (FIG. 41).

Figure 50:
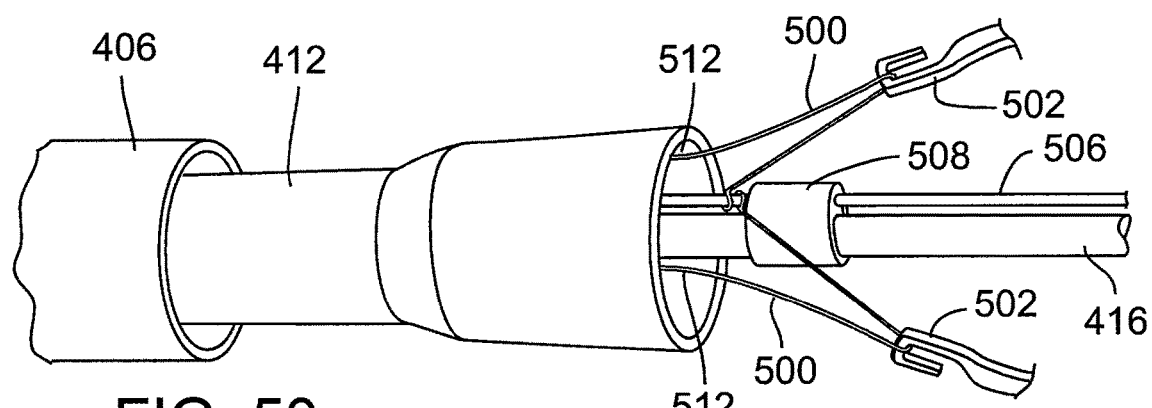
FIG. 50 is an enlarged, perspective view of the distal end of the delivery apparatus similar to FIG. 49 but showing an alternative technique for forming a releasable connection between the valve and the delivery apparatus.

FIG. 50 shows an alternative connection technique for forming a releasable connection between the valve and the valve catheter shaft 412. This embodiment is similar to the embodiment shown in FIG. 48, except that the sutures 500 are not secured relative to the tip portion 510. Instead, the proximal end portions 512 of the sutures are fixedly secured to a sliding release mechanism (not shown), such as an elongated shaft or wire that extends through the valve catheter shaft 412. While the valve is connected to the shaft 412 by the sutures 500, the release mechanism can be moved distally to increase the slack in the sutures 500 to permit controlled expansion of the hook portions 502 of the valve. The release mechanism can be operatively connected to a sliding or rotating knob located on the handle assembly that can be operated by the user to effect sliding movement of the release mechanism. In use, the sheath 406 is retracted relative to the valve. This allows the stent 12 to expand, except for the hook portions 502, which are bent inwardly as they are still connected to the sutures 500. Prior to retracting the release wire 506, the sliding release mechanism is moved distally to increase the slack in the sutures 500, allowing controlled radially expansion of the hook portions 502 of the stent. Once the stent is fully expanded, the release wire 506 can be retracted to release the hook portions 502 of the stent from the sutures 500.

Figure 51:
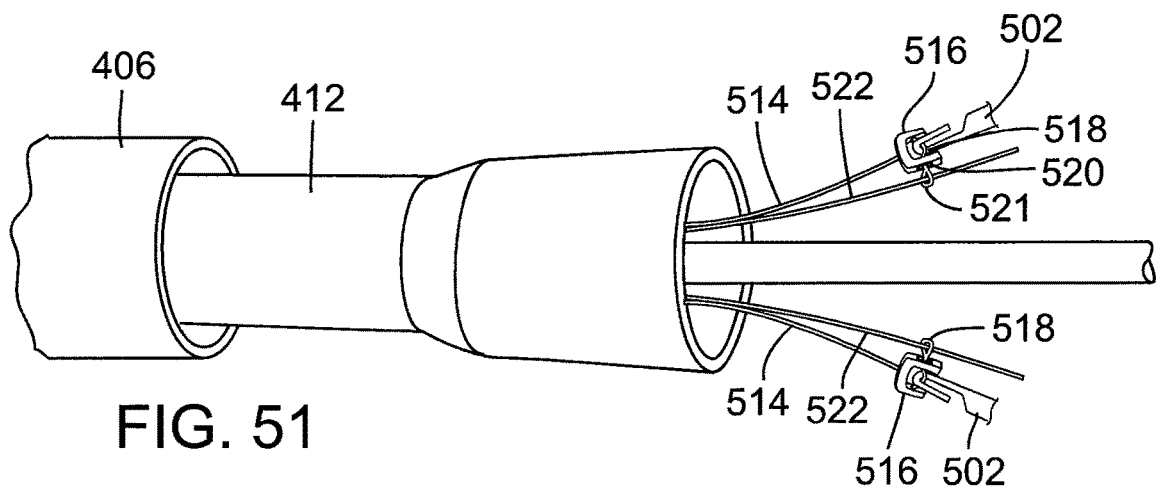
FIG. 51 is an enlarged, perspective view of the distal end of the delivery apparatus similar to FIG. 49 but showing another technique for forming a releasable connection between the valve and the delivery apparatus.

FIG. 51 shows another embodiment of a connection technique for forming a releasable connection between the valve and the valve catheter shaft 412. In this embodiment, a plurality of tethers 514 (one for each hook portion 502 of the stent) extend from the distal end of the valve catheter shaft 412. The distal end of each tether 514 is secured to a respective attachment element 516, which is connected to a respective hook portion 502 by a suture 518. Each suture 518 has one end securely fixed to an attachment element 516, extends through a hook portion 502 and an opening 520 in the attachment element 516, and has a loop 521 at its opposite end. For each tether 514 and attachment element 516, a release wire 522 extends from the distal end of the shaft 412 and through the loop 521 of the respective suture 518. The proximal ends of the tethers 514 can be secured to a sliding release mechanism that can be moved distally to increase the slack in the tethers 514 to permit controlled radially expansion of the hook portions 502 of the stent after the sheath 406 is retracted to deploy the valve from the sheath. Once the stent is fully expanded, each release wire 522 can be retracted to release the respective suture 518, which is then pulled back through the opening 520 to release the hook portion 502. Each release wire 522 can be retracted independently, for example by pulling on the proximal end of each release wire that extends from the handle assembly 408. Alternatively, each release wire 522 can be connected to a common knob on the handle assembly that can be retracted or rotated to simultaneously retract the release wires in unison.

Figure 52A:
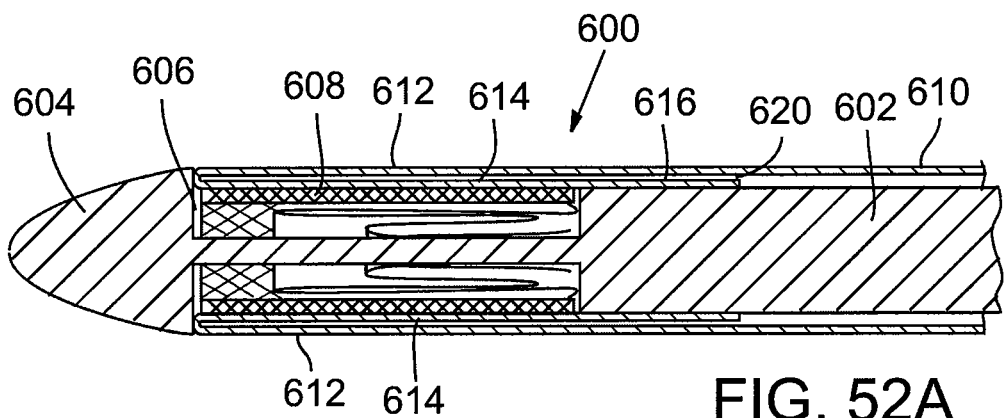
FIGS. 52A and 52B are cross-sectional views of the distal end portion of a delivery apparatus, according to another embodiment.
Figure 52B:
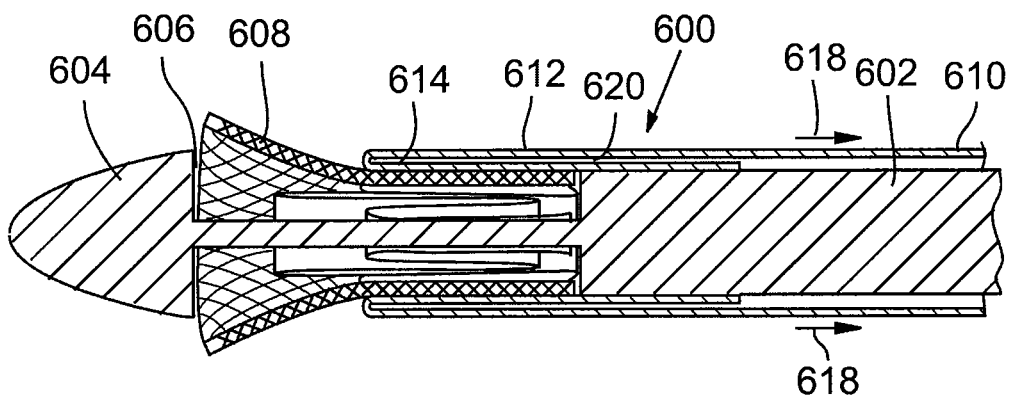

FIGS. 52A and 52B illustrate the distal end portion of a delivery apparatus 600, according to another embodiment. The delivery apparatus 600 includes a catheter shaft 602 having a nose piece 604 at its distal end and an annular recessed portion 606 for receiving a self-expandable stented valve 608 (shown schematically in FIGS. 52A and 52B). A flexible outer sheath, or sleeve, 610 extends over the catheter shaft 602 and the valve 608 and maintains the valve in its compressed state within the recessed portion 606 for delivery through a patient's vasculature. The distal end portion of the sheath 610 that covers the valve is a folded portion having an outer fold layer 612 and an inner fold layer 614. The proximal end 616 of the inner fold layer 614 is secured (e.g., using an adhesive) to the outer surface of the catheter shaft 602. In use, the outer fold layer 612 can be pulled in the proximal direction, as indicated by arrows 618, to uncover the valve and allow it to expand, as shown in FIG. 52B. The sleeve 610 desirably exhibits sufficient rigidity to maintain a cylindrical shape against the outward expansion force of the valve 608 yet is flexible enough to allow the outer fold layer to be pulled back relative to the inner fold layer. Optionally, a thin fluid layer 620 can be formed between the outer fold layer 612 and the inner fold layer 614 to lubricate and minimize friction the adjacent surfaces of the fold layers. An advantage of the delivery apparatus 600 is that there are no frictional forces generated between the sleeve 610 and the valve 608 as the sleeve is pulled back, and as such, less force is needed by a user to release the valve from its compressed, sheathed state.

The sleeve 610 can be constructed from any of various materials, including various polymers (e.g., nylon or PTFE) or metals (e.g., Nitinol). The sleeve can comprise one or more layers of material, which can be, for example, a braided layer, a mesh layer, a non-perforated layer or any combinations thereof. Although not shown in the figures, the sleeve 610 can extend to the handle of the delivery apparatus for manipulation by a user. Alternatively, the sleeve 610 can terminate short of the handle and can be connected to one or more pull wires extending between the proximal end of the sleeve and the handle, which pull wires can be pulled proximally to pull back the outer fold layer for deploying the valve.

Although the nose piece 604 is shown as part of the catheter shaft 602, this is not a requirement. In alternative embodiments, the delivery apparatus can include an inner nose catheter shaft that extends through the shaft 602 and mounts the nose piece 604, as described in the embodiments above. In addition, any of the various connection mechanisms disclosed herein for forming a releasable connection between the valve and the delivery apparatus can be incorporated in the embodiment shown in FIGS. 52A and 52B. Moreover, the shaft 602 can be the shaft of a balloon catheter having an inflatable balloon at the distal end of the shaft for mounting a balloon-expandable valve on the balloon (in which case, the valve need not be self-expandable).

Figure 53A:
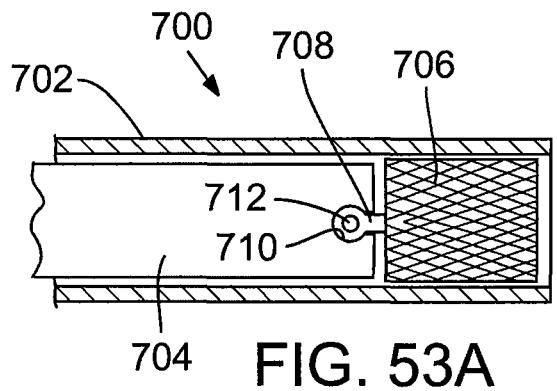
FIG. 53A is a cross-sectional view of the distal end portion of a delivery apparatus, according to another embodiment.
Figure 53B:
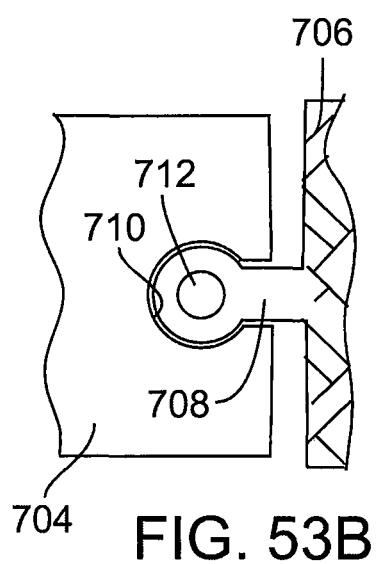
FIG. 53B is an enlarged view of a portion of FIG. 53A showing the connection between the valve stent and the distal end of the delivery apparatus.
Figure 53C:
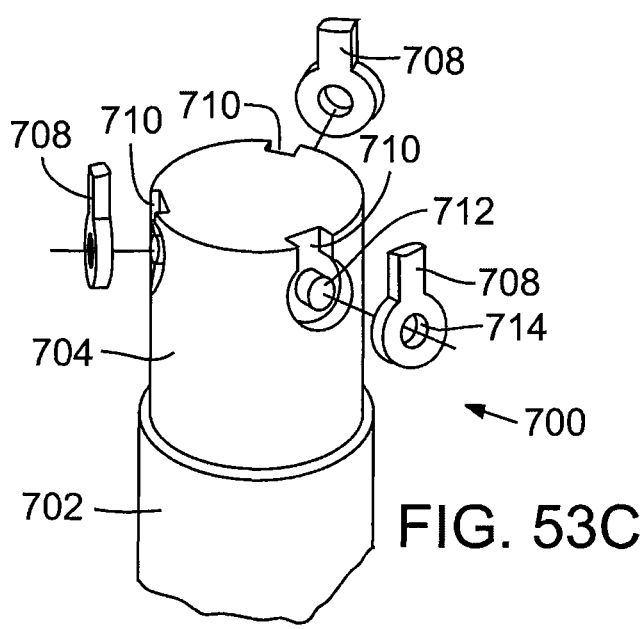
FIG. 53C is a perspective view of the delivery apparatus of FIG. 53A.

FIGS. 53A-53E illustrate a delivery apparatus 700 according to another embodiment. The delivery apparatus 700 comprises an outer catheter shaft 702 and an inner catheter shaft 704 extending through the outer shaft. The distal end portion of the outer shaft 702 comprises a sheath that extends over a prosthetic, stented valve 706 (shown schematically) and retains it in a compressed state during delivery through the patient's vasculature. The distal end portion of the inner shaft 704 is shaped to cooperate with one or more mating extension arms, or posts, 708 that extend from the stent of the valve 706 to form a releasable connection between the valve and the delivery apparatus. For example, in the illustrated embodiment each post 708 comprises a straight portion terminating at a circular ring portion and the distal end portion of the shaft 704 has correspondingly shaped recesses 710 that receive respective posts 708. Each recess 710 can include a radially extending projection 712 that is shaped to extend into an opening 714 in a respective post 708. As best shown in FIG. 53B, each recess 710 and projection 712 can be sized to provide a small gap between the surfaces of the post 708 and the adjacent surfaces within the recess to facilitate insertion and removal of the post from the recess in the radial direction (i.e., perpendicular to the axis of the shaft 704).

Figure 53D:
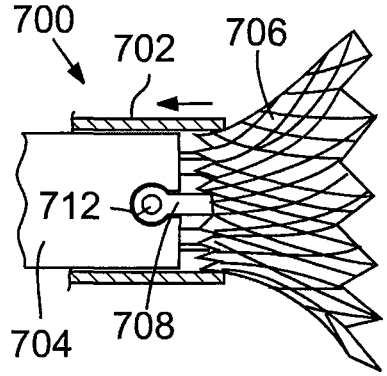
FIGS. 53D and 53E illustrate the valve being deployed from the delivery apparatus shown in FIG. 53A.
Figure 53E:
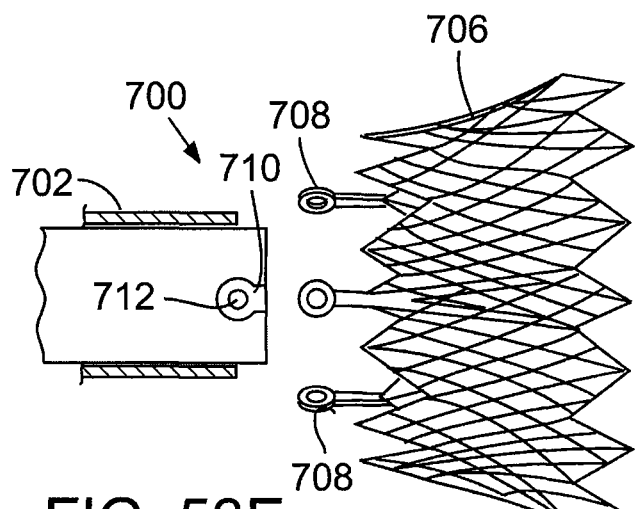

When the valve 706 is loaded into the delivery apparatus 700, as depicted in FIG. 53A, such that each post 708 of the valve is disposed in a recess 710, the valve is retained against axial movement relative to the shaft 704 (in the proximal and distal directions) by virtue of the shape of the posts and the corresponding recesses. Referring to FIG. 53D, as the outer shaft 702 is retracted to deploy the valve 706, the valve is allowed to expand but is retained against "jumping" from the distal end of the sheath by the connection formed by the posts and the corresponding recesses for controlled delivery of the valve. At this stage the partially deployed valve is still retained by the shaft 704 and can be retracted back into the outer sheath 702 by retracting the shaft 704 proximally relative to the outer sheath 702. Referring to FIG. 53E, when the outer sheath is retracted in the proximal direction past the posts 708, the expansion force of the valve stent causes the posts to expand radially outwardly from the recesses 710, thereby fully releasing the valve from the shaft 704.

While three posts 708 and corresponding recesses 710 are shown in the illustrated embodiment, any number of posts and recesses can be used. Furthermore, the posts and recesses can have various other shapes, such as square, oval, rectangular, triangular, or various combinations thereof. The posts can be formed from the same material that is used to form the valve stent (e.g., stainless steel or Nitinol). Alternatively, the posts can be loops formed from less rigid material, such as suture material. The loops are secured to the valve stent and are sized to be received in the recesses 710.

FIGS. 54A-54D illustrate a delivery apparatus 800 that is similar to the delivery apparatus shown in FIGS. 53A-53E. The delivery apparatus 800 includes a handle portion 802 having a rotatable knob 804, an outer catheter shaft 806 extending from the handle portion 802, and an inner catheter shaft 808 extending from the handle portion and through the outer catheter shaft 806. The distal end of the inner catheter shaft 808 includes an end piece 810 that is formed with an annular recess 812 and a plurality of axially extending, angularly spaced recesses 814. The recesses 812, 814 are sized and shaped to receive T-shaped posts 816 extending from the stent of a valve (not shown in FIGS. 54A-54D). Each post 816 has an axially extending portion 816a that is received in a corresponding recess 814 and a transverse end portion 816b that is received in the annular recess 812. The outer shaft 806 includes a sheath 818 that is sized and shaped to extend over the end piece 812 and the valve during delivery of the valve.

The outer shaft 806 is operatively connected to the knob 804 to effect longitudinal movement of the outer shaft 806 and the sheath 818 relative to the inner shaft 808 upon rotation of the knob 804, such as described above in connection with the embodiment shown in FIGS. 40-42. In use, the valve is mounted for delivery by placing the posts 816 of the valve in the recesses 812, 814 and moving the sheath distally to extend over the valve to maintain the valve in a compressed state. At or near the target site for implanting the valve, the knob 804 is rotated to retract the sheath 818 relative to the valve. As the sheath is retracted to deploy the valve, the valve is allowed to expand but is retained against "jumping" from the distal end of the sheath by the connection formed by the posts and the corresponding recesses for controlled delivery of the valve. At this stage the partially deployed valve is still retained by the end piece 810 and can be retracted back into the sheath by moving the shaft 806 distally relative to the valve. When the sheath is retracted in the proximal direction past the posts 816, the expansion force of the valve stent causes the posts to expand radially outwardly from the recesses 812, 814, thereby fully releasing the valve from the end piece 810.

Figure 55A:
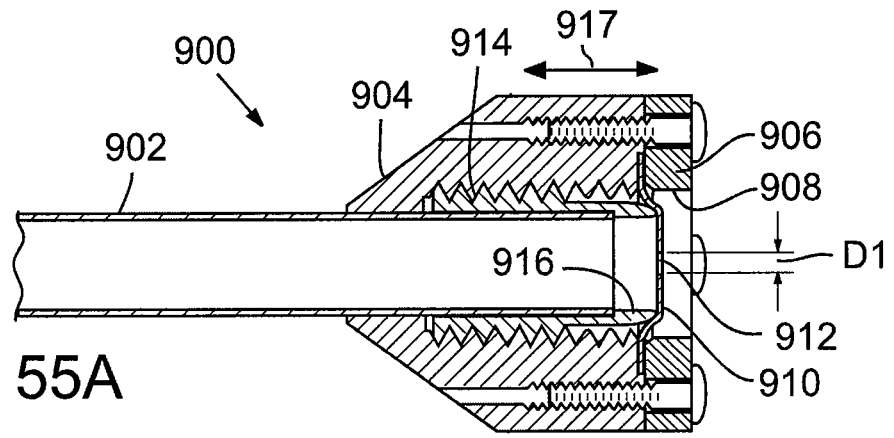
FIGS. 55A and 55B are cross-sectional views of an embodiment of a loader device that can be used with an introducer sheath for introducing a delivery apparatus into the body.
Figure 55B:
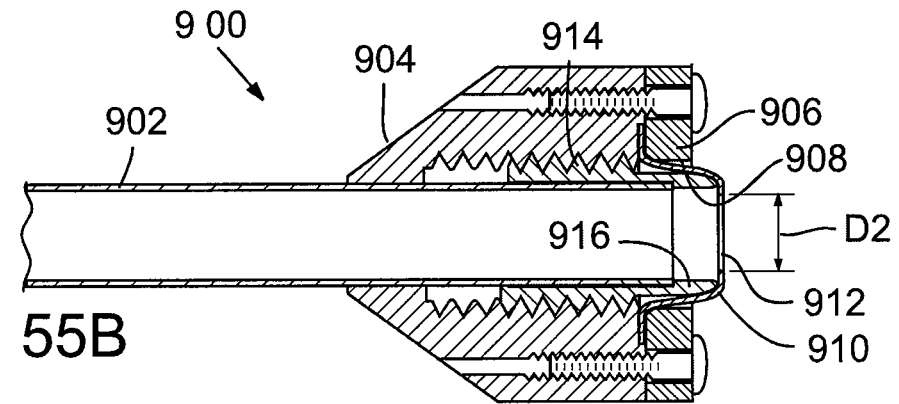

FIGS. 55A-55B show an embodiment of an introducer, indicated at 900, that can be used to introduce a catheter or similar device into the body, for example, a delivery apparatus for delivering and implanting a prosthetic heart valve. The introducer 900 includes an elongated tube, or shaft, 902 sized for insertion into a body channel (e.g., a blood vessel). The tube 902 extends from a housing 904. Mounted to the proximal end of the housing is a cap portion 906 having a central opening 908 for receiving a catheter (not shown in FIGS. 55A-55B). A seal 910 is captured between the opposing faces of the cap portion and the housing. The seal can be made from any suitable resilient material, such as silicone rubber, or any of various other suitable elastomers. The seal has a central opening 912 that is aligned with the opening 908 of the cap portion and the lumen of the tube 902. The seal 910 is sized to permit a catheter to be inserted through opening 912 while engaging the outer surface of the catheter to minimize blood loss during insertion of the catheter into the body. The proximal end portion of the tube 902 located within the housing has an externally threaded portion 914 that engages corresponding internal threads on the inner surface of the housing 904. A proximal extension portion 916 of the threaded portion 914 contacts the seal 910. The threaded portion 914 is fixedly secured to the tube 902, such as with a suitable adhesive. In alternative embodiments, the tube and threaded portion can have a unitary or one-piece construction where the threaded portion is formed directly on the tube.

The housing 904 is movable longitudinally relative to the tube 902, as indicated by double-headed arrow 917, to selectively dilate or contract the opening 912 in the seal 910. The housing 904 in the illustrated embodiment is rotatable relative to the tube 902 to effect longitudinal movement of the housing relative to the tube. As the housing is moved from a proximal position (FIG. 55A) to a distal position (FIG. 55B), the seal 910 is stretched against the extension portion 916, which dilates the seal opening 912 from a first diameter D1 to a second, larger diameter D2. As mentioned above, the introducer 900 can be used to assist in the introduction of a valve-delivery apparatus (e.g., delivery apparatus 100 described above) into the body. In use, the tube 902 is inserted into a blood vessel (e.g., the femoral artery), which can be dilated beforehand in a conventional manner. The housing 904 is then moved distally to dilate the opening in the seal to a diameter large enough to permit passage of the compressed valve (and any sheath covering the valve) into the lumen of the tube 902. After the valve (or the largest portion of the delivery apparatus) has passed through the seal, the housing is rotated in the opposite direction to move the housing proximally to allow the seal opening 912 to contract back to its pre-dilated size. In this state, the seal engages the outer surface of the delivery apparatus to prevent or at least minimize blood loss along the outer surface of the delivery apparatus.

Figure 56A:
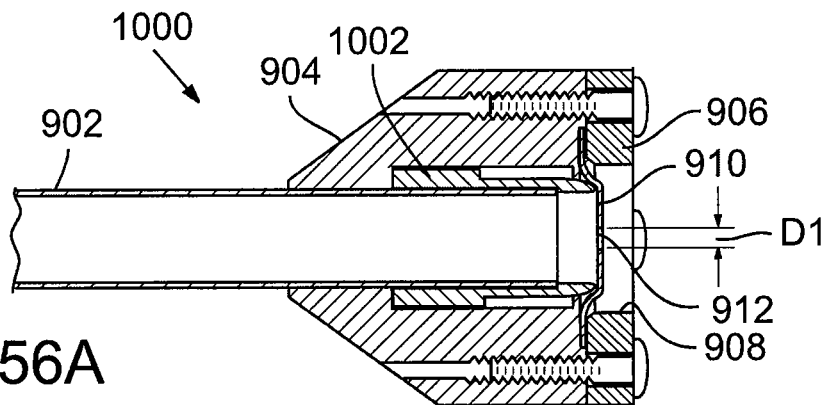
FIGS. 56A and 56B are cross-sectional views of another embodiment of a loader device.
Figure 56B:
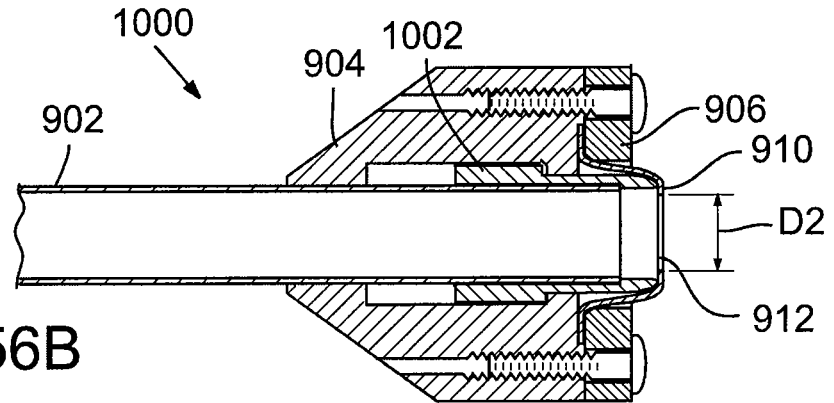

FIGS. 56A-56B show an introducer 1000, according to another embodiment. This embodiment shares many similarities with the embodiment of FIGS. 55A-55B. Hence, components in FIGS. 56A-56B that are identical to corresponding components in FIGS. 55A-55B have the same respective reference numerals and are not described further. The introducer 1000 differs from the introducer 900 in that the tube 902 of introducer 1000 includes an external portion 1002 that slidably engages an inner surface of the housing 904. Hence, rather than rotating the housing 904, the housing can simply be pushed distally relative to the tube 902 in order to dilate the seal opening 912, as depicted in FIG. 56B. Removal of manual pressure from the housing 904 allows the elasticity of the seal 910 to pull the housing back proximally for contracting the seal opening.

FIGS. 57A and 57B show an integrated introducer sheath and loader assembly, indicated at 1100, that can be used to facilitate insertion of a delivery apparatus (e.g., a valve delivery apparatus) into a body vessel. The introducer sheath is particularly suited for use with a delivery apparatus that is used to implant a prosthetic valve, such as the embodiments of delivery apparatus described herein. The introducer sheath also can be used to introduce other types of delivery apparatus for placing various types of intraluminal devices (e.g., stents, stented grafts, etc.) into many types of vascular and nonvascular body lumens (e.g., veins, arteries, esophagus, ducts of the biliary tree, intestine, urethra, fallopian tube, other endocrine or exocrine ducts, etc.).

A conventional introducer sheath typically requires a tubular loader to be inserted through the seals in the sheath housing to provide an unobstructed path for a valve mounted on a balloon catheter. The loader extends from the proximal end of the introducer sheath, thereby increasing its working length, and decreasing the available working length of a delivery apparatus that can be inserted into the body. The introducer sheath 1100 includes an integrated loader tube housed in the sheath housing to reduce the working length of the sheath and therefore increase the available working length of a delivery apparatus that can be inserted into the body. Moreover, a conventional introducer sheath includes a cap and a respective seal that typically is removed from the introducer sheath and preloaded onto the shaft of the delivery apparatus before the prosthetic valve is mounted to the distal end of the shaft, and then reattached to the sheath housing as the valve and delivery apparatus are inserted into the sheath housing. The procedure is carried out in this manner in order to prevent damage to the prosthetic valve that otherwise might occur if the valve, while mounted on the shaft in a crimped state, is pushed through the opening in the seal. In some cases, the seal can become dislodged from its intended position within the cap, which can cause damage to the seal. In such cases, the user may need to disassemble the cap and seal assembly for repair or replacement of the seal.

The illustrated assembly 1100 includes a seal housing 1102 and a tubular sleeve 1104 extending distally from the housing. The seal housing 1102 houses one or more sealing valves, such as a cross-slit valve 1106, a disc valve 1108, and a hemostatic valve 1110 as shown in the illustrated embodiment. The valves desirably are fabricated from a resilient biocompatible material, such as polyisoprene, although similar biocompatible materials also can be used. The valves 1106, 1108, 1110 are further shown and described in U.S. Pat. No. 6,379,372, which is incorporated herein by reference. A spacer 1112 can be interposed between the cross-slit valve 1106 and the proximal end of the seal housing.

Coupled to the proximal end of the seal housing is an end piece 1114 adapted to move longitudinally along the length of the seal housing. In the illustrated embodiment, the end piece has a tubular body formed with internal threads 1116 that engage an externally threaded portion 1118 on the outer surface of the seal housing 1102. Thus, rotation of the end piece 1114 moves the same inwardly and outwardly relative to the seal housing. The end piece 1114 has a cap portion 1119 at its proximal end having a central opening 1120 and an elongated loader tube 1122 fixedly secured inside the end piece. The opening 1120 and the loader tube 1122 are dimensioned to permit passage of a valve (or other prosthesis) mounted on the delivery apparatus. The end piece 1114 also houses a seal 1124 having a central opening 1126 aligned with the opening 1120. The seal 1124 sealingly engages the outer surface of the delivery apparatus when it is inserted into the introducer sheath assembly 1100.

As noted above, the end piece 1114 can be adjusted inwardly and outwardly relative to the seal housing 1102. Adjusting the end piece 1114 from the extended position shown in FIG. 57A to the retracted position shown in FIG. 57B moves the loader tube 1122 through the seals 1106, 1108, 1110 to provide an unobstructed path for the valve to pass through the introducer sheath. Because the loader tube does not extend behind the end piece, as in a conventional introducer sheath, the loader tube does not decrease the available working length of the delivery apparatus that can be inserted into the vasculature. In addition, the cap portion 1119 is slidably mounted for longitudinal movement on the end piece 1114 and has an inner tubular portion 1128 that is positioned to engage and stretch the seal 1124. When the cap portion 1119 is pushed distally relative to the end piece, the tubular portion 1128 stretches the seal 1124 and dilates the seal opening 1126 from a first diameter (FIG. 57A) to a second, larger diameter (FIG. 57B) to provide an unobstructed path for the delivery apparatus and the crimped valve into the assembly. In contrast to a conventional introducer sheath, the cap and its respective seal need not be removed from the sheath and preloaded onto the delivery apparatus prior to mounting the valve onto the delivery apparatus. As can be appreciated, the configuration of the illustrated embodiment facilitates introduction of the delivery apparatus into the sheath and avoids possible seal dislodgement during the loading process.

In use, the introducer sheath 1100 in the extended position shown in FIG. 57A can be placed on a previously inserted guide wire (not shown) and advanced thereon until the sleeve 1104 extends into a body vessel a desired distance. The cap portion can then be pushed distally to dilate the seal 1124 to permit passage of the delivery apparatus through the seal opening 1126 to position the valve in the loader tube 1122. Thereafter the cap portion can be allowed to move back to the proximal position under the elasticity of the seal (FIG. 57A), thereby allowing the seal 1124 to form a fluid tight seal around the outer shaft of the delivery apparatus. Subsequently, the end piece 1114 is rotated to slide the loader tube 1122 through the valves 1106, 1108, 1110 (FIG. 57B), thus placing the delivery apparatus in communication with the lumen of the sleeve 1104 and the body vessel in which the sleeve is inserted. Advantageously, this approach simplifies the loading process and reduces the number of steps and parts required to load the valve into the sheath.

In an alternative embodiment of the introducer sheath 1100, the seal housing 1102 can have internal threads that engage external threads on the end piece 1114. The end piece can be rotated to adjust the position of the loader tube 1122 as previously described. In addition, the pitch of the threads on the seal housing and the end piece can be varied to vary the amount of rotational movement required to extend the loader through the sealing valves. In another embodiment, the end piece 1114 can be slidingly positionable along the length of the seal housing by pushing and pulling the end piece without rotating the same. In another alternative embodiment, the cap portion can be rotatable relative to the end piece 1114 to effect longitudinal movement of the cap portion for dilating the seal, such as shown in the embodiment of FIGS. 56A and 56B.

Known introducer sheaths typically employ a sleeve made from polymeric tubing having a radial wall thickness of about 0.010 to 0.015 inch. FIG. 58A shows another embodiment of an introducer sheath, indicated at 1200, that employs a thin metallic tubular layer that has a much smaller wall thickness compared to known devices. In particular embodiments, the wall thickness of the sheath 1200 is about 0.0005 to about 0.002 inch. The introducer sheath 1200 includes a proximally located housing, or hub, 1202 and a distally extending sleeve, or cannula, 1204. The housing 1202 can house a seal or a series of seals as described in detail above to minimize blood loss. The sleeve 1204 includes a tubular layer 1206 that is formed from a metal or metal alloy, such as Nitinol or stainless steel, and desirably is formed with a series of circumferentially extending or helically extending slits or openings to impart a desired degree of flexibility to the sleeve.

As shown in FIG. 58B, for example, the tubular layer 1206 is formed (e.g., laser cut) with an "I-beam" pattern of alternating circular bands 1207 and openings 1208 with axially extending connecting portions 1210 connecting adjacent bands 1207. Two adjacent bands 1207 can be connected by a plurality of angularly spaced connecting portions 1210, such as four connecting portions 1210 spaced 90 degrees from each other around the axis of the sleeve, as shown in the illustrated embodiment. The sleeve 1204 exhibits sufficient flexibility to allow the sleeve to flex as it is pushed through a tortuous pathway without kinking or buckling. FIG. 59 shows another pattern of openings that can be laser cut or otherwise formed in the tubular layer 1206. The tubular layer in the embodiment of FIG. 59 has a pattern of alternating bands 1212 and openings 1214 with connecting portions 1216 connecting adjacent bands 1212 and arranged in a helical pattern along the length of the sleeve. In alternative embodiments, the pattern of bands and openings and/or the width of the bands and/or openings can vary along the length of the sleeve in order to vary stiffness of the sleeve along its length. For example, the width of the bands can decrease from the proximal end to the distal end of the sleeve to provide greater stiffness near the proximal end and greater flexibility near the distal end of the sleeve.

As shown in FIG. 60, the sleeve can have a thin outer layer 1218 extending over the tubular layer 1206 and made of a low friction material to reduce friction between the sleeve and the vessel wall into which the sleeve is inserted. The sleeve can also have a thin inner layer 1220 covering the inner surface of the tubular layer 1206 and made of a low friction material to reduce friction between the sleeve and the delivery apparatus that is inserted into the sleeve. The inner and outer layers can be made from a suitable polymer, such as PET, PTFE, and/or FEP.

In particular embodiments, the tubular layer 1206 has a radial wall thickness in the range of about 0.0005 inch to about 0.002 inch. As such, the sleeve can be provided with an outer diameter that is about 1-2 Fr smaller than known devices. The relatively smaller profile of the sleeve 1204 improves ease of use, lowers risk of patient injury via tearing of the arterial walls, and increases the potential use of minimally invasive procedures (e.g., heart valve replacement) for patients with highly calcified arteries, tortuous pathways or small vascular diameters.

In an alternative embodiment, a delivery apparatus can be provided with a power source to effect rotation of the torque shaft in lieu of or in addition to a knob or similar mechanism that uses manual power to rotate the torque shaft. For example, the handle portion 308 (FIG. 35) can house a small electric motor that is connected to and transfers rotational motion to the gear 348. In this way, the user can effect rotation of the torque shaft 312 (to un-sheath the valve 10) by simply activating the motor of the handle portion. The motor desirably is a two-way motor so that the torque shaft can be rotated in both directions. Alternatively, the power source can be a hydraulic power source (e.g., hydraulic pump) or pneumatic (air-operated) power source that is configured to rotate the torque shaft.

In another embodiment, a power source (e.g., an electric, hydraulic, or pneumatic power source) can be operatively connected to a shaft, which is turn is connected to a valve 10. The power source is configured to reciprocate the shaft longitudinally in the distal direction relative to a valve sheath in a precise and controlled manner in order to advance the valve from the sheath. Alternatively, the power source can be operatively connected to sheath in order to reciprocate the sheath longitudinally in the proximal direction relative to the valve to deploy the valve from the sheath.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for loading a prosthetic heart valve within a cylindrical delivery sheath of a delivery apparatus, the delivery apparatus comprising a catheter adapted to extend through a patient's vasculature, the method comprising:
   attaching the prosthetic heart valve to a valve-retaining mechanism at a distal end of the catheter; and
   causing a torque shaft of the delivery apparatus to rotate relative to the catheter, wherein the torque shaft extends within the catheter and is coupled to the delivery sheath,
   wherein rotation of the torque shaft relative to the catheter causes relative longitudinal movement between the delivery sheath and the prosthetic heart valve such that the prosthetic heart valve is covered at least partially by the delivery sheath, the delivery sheath being configured to extend over and hold the prosthetic heart valve in a radially compressed state;
   wherein a distal end portion of the torque shaft is connected to the valve-retaining mechanism.

2. The method of claim 1, wherein rotation of the torque shaft causes the delivery sheath to move longitudinally distally relative to the catheter and relative to the prosthetic valve.

3. The method of claim 1, wherein the delivery apparatus comprises a handle portion connected to a proximal end of the catheter and a proximal end of the torque shaft, the handle portion comprising a rotatable knob coupled to the torque shaft and configured to rotate the torque shaft relative to the delivery sheath upon rotation of the knob, and wherein causing the torque shaft to rotate is done by rotating the knob.

4. The method of claim 3, wherein the handle portion comprises a first gear disposed on the torque shaft and a second gear engaging the first gear and coupled to the knob to transmit rotational movement of the knob to the first gear and therefore to the torque shaft.

5. The method of claim 1, wherein the delivery apparatus comprises a handle portion connected to a proximal end of the catheter and to a proximal end of the torque shaft, the handle portion comprising a motor coupled to the torque shaft and configured to rotate the torque shaft relative to the delivery sheath upon actuation of the motor, and wherein causing the torque shaft to rotate is done by actuating the motor.

6. The method of claim 1, wherein a loading cone is used to guide the prosthetic heart valve into the delivery sheath and rotation of the torque shaft relative to the catheter causes relative longitudinal movement between the delivery sheath and the prosthetic heart valve such that the prosthetic heart valve is covered by the delivery sheath as the prosthetic heart valve exits the loading cone in the radially compressed state.

7. The method of claim 1, wherein the valve-retaining mechanism includes at least one suture and at least one slidable member, wherein the at least one suture comprises a loop and a distal end portion of the at least one slidable member can move axially such that it can pass through the loop or be removed from the loop, and wherein attaching the prosthetic heart valve to the valve-retaining mechanism includes passing the at least one suture through a frame of the prosthetic heart valve and passing the at least one slidable member through the loop.

8. The method of claim 1, wherein the prosthetic heart valve is held in the radially compressed state within the delivery sheath at a location distal to a distal end of the torque shaft.

9. A method for loading a prosthetic heart valve within a delivery apparatus, comprising:
   causing a torque shaft of the delivery apparatus to rotate, wherein the torque shaft extends within and is rotated relative to a catheter of the delivery apparatus that comprises an elongated shaft adapted to extend through a patient's vasculature and a cylindrical valve sheath, and
   wherein the act of causing the torque shaft to rotate causes relative longitudinal movement between the valve sheath and the prosthetic heart valve such that at least a portion of the prosthetic heart valve is radially compressed by a loading cone and fed into the valve sheath, the valve sheath being configured to extend over and hold the prosthetic heart valve in a radially compressed state;
   wherein a distal end portion of the elongated shaft extends into a lumen of the valve sheath.

10. The method of claim 9, wherein rotation of the torque shaft causes the valve sheath to move longitudinally distally relative to the torque shaft and relative to the prosthetic valve.

11. The method of claim 9, wherein the delivery apparatus comprises a handle portion connected to a proximal end of the catheter and a proximal end of the torque shaft, the handle portion comprising a rotatable knob coupled to the torque shaft and configured to rotate the torque shaft relative to the valve sheath upon rotation of the knob, and wherein causing the torque shaft to rotate is done by rotating the knob.

12. The method of claim 11, wherein the handle portion comprises a first gear disposed on the torque shaft and a second gear engaging the first gear and coupled to the knob to transmit rotational movement of the knob to the first gear and therefore to the torque shaft.

13. The method of claim 9, wherein the delivery apparatus comprises a handle portion connected to a proximal end of the catheter and to a proximal end of the torque shaft, the handle portion comprising a motor coupled to the torque shaft and configured to rotate the torque shaft relative to the valve sheath upon actuation of the motor, and wherein causing the torque shaft to rotate is done by actuating the motor.

14. The method of claim 9, wherein the act of causing the torque shaft to rotate causes the valve sheath to extend over and hold the prosthetic heart valve in a radially compressed state at a location distal to a distal end of the torque shaft.

15. A method for loading a prosthetic heart valve within a delivery apparatus, comprising:
   securing the prosthetic heart valve to a retaining mechanism of the delivery apparatus, wherein the prosthetic heart valve comprises an expandable frame member and a plurality of leaflets;
   pushing the prosthetic heart valve through a loading device to radially compress the prosthetic heart valve; and
   causing a torque shaft of the delivery apparatus to rotate within and relative to an elongated shaft of the delivery apparatus, such that rotation of the torque shaft relative to the elongated shaft causes a valve sheath of the delivery apparatus to move longitudinally over the prosthetic heart valve as the prosthetic heart valve exits the loading device, wherein the valve sheath is configured to hold the prosthetic heart valve in a radially compressed state, and wherein a distal end portion of the elongated shaft extends into a lumen of the valve sheath.

16. The method of claim 15, wherein the delivery apparatus comprises a handle portion connected to a proximal end of the torque shaft, the handle portion comprising a motor coupled to the torque shaft and configured to rotate the torque shaft relative to the valve sheath upon actuation of the motor, and wherein causing the torque shaft to rotate is done by actuating the motor.

* * * * *